(12) United States Patent
Kataoka et al.

(10) Patent No.: US 9,750,687 B2
(45) Date of Patent: Sep. 5, 2017

(54) SUBSTANCE-ENCAPSULATING VESICLE AND PROCESS FOR PRODUCING THE SAME

(75) Inventors: Kazunori Kataoka, Nakano-ku (JP);
Akihiro Kishimura, Arakawa-ku (JP);
Yasutaka Anraku, Bunkyo-ku (JP);
Kanjiro Miyata, Nishitokyo (JP);
Sayan Chuanoi, Bunkyo-ku (JP);
Tomoya Suma, Bunkyo-ku (JP);
Makoto Oba, Bunkyo-ku (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 574 days.

(21) Appl. No.: 13/699,238

(22) PCT Filed: May 23, 2011

(86) PCT No.: PCT/JP2011/061790
§ 371 (c)(1),
(2), (4) Date: Nov. 20, 2012

(87) PCT Pub. No.: WO2011/145745
PCT Pub. Date: Nov. 24, 2011

(65) Prior Publication Data
US 2013/0202711 A1 Aug. 8, 2013

(30) Foreign Application Priority Data

May 21, 2010 (JP) .................................. 2010-117821
May 21, 2010 (JP) .................................. 2010-117823

(51) Int. Cl.
*A61K 9/32* (2006.01)
*A61K 9/00* (2006.01)
*A61K 9/127* (2006.01)
*B01J 13/02* (2006.01)
*B01J 13/14* (2006.01)

(52) U.S. Cl.
CPC .......... *A61K 9/0087* (2013.01); *A61K 9/1273* (2013.01); *B01J 13/02* (2013.01); *B01J 13/14* (2013.01)

(58) Field of Classification Search
CPC ........ A61K 8/0294; A61K 8/14; A61K 9/127; A61K 9/1271; A61K 9/1272; A61K 9/1273; A61K 45/48815; A61K 2039/5555
USPC ................................................. 424/465–489
See application file for complete search history.

(56) References Cited

U.S. PATENT DOCUMENTS 5,100,662 A * 3/1992 Bolcsak ............... A61K 9/1271
424/208.1
7,498,045 B2 * 3/2009 Chang .................. A61K 9/5153
424/450

8,304,497 B2 * 11/2012 Kataoka et al. .............. 525/403
2002/0197210 A1 * 12/2002 Bednarski et al. .......... 424/1.29
2005/0003016 A1    1/2005 Discher et al.
2007/0003528 A1 *  1/2007 Consigny et al. .......... 424/93.7
2009/0081458 A1 *  3/2009 Kataoka ............... A61K 9/1273
428/402
2016/0051484 A1    2/2016 Kataoka et al.

FOREIGN PATENT DOCUMENTS

| CH | WO 2007008300 A2 * | 1/2007 | ........... A61L 31/048 |
|---|---|---|---|
| EP | 0 721 776 A | 7/1996 | |
| EP | 1 878 766 A1 | 1/2008 | |
| JP | H8-188541 | 7/1996 | |
| WO | 2006/118260 A | 11/2006 | |
| WO | WO 2007008300 A2 * | 1/2007 | |
| WO | 2009/057812 A1 | 5/2009 | |
| WO | 2010/068432 A1 | 6/2010 | |

OTHER PUBLICATIONS

Extended European Search Report corresponding to EP 11 78 3676 dated Oct. 28, 2013 (7 pages).
European Search Report, mailed Jul. 17, 2013, EP application No. 13166732, 6 pages.
Anraku et al., J. Am Chem. Soc., 2010, vol. 132(5), 1631-1636.
Batzri et al., Biochem. Biophys Acta, 1973, vol. 298, 1015-1019.
Kataoka, "Intracellular gene delivery by polymer micelle vectors," Japanese Journal of Clinical Medicine, Mar. 1988, vol. 56, No. 3, pp. 166-171.
Kataoka, Shin Drag Delivery System, Kabushi Kaisha CMC, Jan. 31, 2000, pp. 155-164.
Nyin et al., Soft Matter, 2006, vol. 2, 940-949.
Ranquin et al., Nano Lett., 2005, 5:2220-4.
Schlaad et al., Macromolecules, 2003, vol. 36(5), 1417-1420.
Szoka, Jr., et al., Proc. Natl. Acad. Sci. USA, 1978, vol. 75(9), 4194-4198.
Tong et al, J. Phys. Chem. B, 2005, vol. 109, 13159-13165.
U.S. Appl. No. 14/839,854, Non-Final Office Action mailed Oct. 21, 2016, 19 pages.
U.S. Appl. No. 14/839,854, Final Office Action mailed Dec. 30, 2016, 7 pages.

* cited by examiner

*Primary Examiner* — Micah-Paul Young
(74) *Attorney, Agent, or Firm* — Kilpatrick Townsend & Stockton LLP

(57) ABSTRACT

Provided is a method for easily and efficiently producing encapsulated substance vesicles wherein a substance is encapsulated in the cavity of vesicles obtained by polymer self-assembly. Empty vesicles that have membranes comprising a first polymer that is a block copolymer with uncharged hydrophilic segments and a first kind of charged segments and a second polymer with a second kind of charged segments that carry a charge that is the opposite of said first kind of charged segments as well as spaces that are enclosed by said membranes are mixed in an aqueous medium with the substance that is to be encapsulated in the spaces.

8 Claims, 20 Drawing Sheets

(a)

MIX UNDER SHEAR STRESS (b)

(a)

(b)

(a)

(b)

(a)

(b)

(c)

(a)

(b)

(a)

(b)

(a)

(b)

SIDE OF THE IMAGE: ■ 25[nm]
230[nm]

SIDE OF THE IMAGE: ■ 50[nm]
460[nm]

(c)

(d)

SIDE OF THE IMAGE: ■ 25[nm]
230[nm]

SIDE OF THE IMAGE: ■ 50[nm]
460[nm]

SIDE OF THE IMAGE:　　■ 50[nm]
460[nm]

(b)

SIDE OF THE IMAGE:　　■ 50[nm]
460[nm]

(a)

(b)

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: synthetic fire fly luciferase (GL3, Luc) siRNA
      sense strand
<220> FEATURE:
<223> OTHER INFORMATION: Description of Combined DNA/RNA Molecule:
      synthetic fire fly luciferase (GL3, Luc) siRNA sense strand

<400> SEQUENCE: 1
cuuacgcuga guacuucgat t                                              21

```
<210> SEQ ID NO 2
<211> LENGTH: 21
<212> TYPE: DNA
<213> ORGANISM: Artificial Sequence
<220> FEATURE:
<223> OTHER INFORMATION: synthetic fire fly luciferase (GL3, Luc) siRNA
      antisense strand
<220> FEATURE:
<223> OTHER INFORMATION: Description of Combined DNA/RNA Molecule:
      synthetic fire fly luciferase (GL3, Luc) siRNA antisense strand

<400> SEQUENCE: 2
ucgaaguacu cagcguaagt t                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic scramble control siRNA sense strand
<220> FEATURE:
<223> OTHER INFORMATION: Description of Combined DNA/RNA Molecule:
      synthetic scramble control siRNA sense strand

<400> SEQUENCE: 3
uucuccgaac gugucacgut t                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic scramble control siRNA antisense
      strand
<220> FEATURE:
<223> OTHER INFORMATION: Description of Combined DNA/RNA Molecule:
      synthetic scramble control siRNA antisense strand

<400> SEQUENCE: 4
acgugacacg uucggagaat t                                              21
```

SUBSTANCE-ENCAPSULATING VESICLE AND PROCESS FOR PRODUCING THE SAME

REFERENCE TO A "SEQUENCE LISTING," A TABLE, OR A COMPUTER PROGRAM LISTING APPENDIX SUBMITTED AS AN ASCII TEXT FILE

The Sequence Listing written in file 93803-858253.TXT, created on Mar. 18, 2013, 4,096 bytes, machine format IBM-PC, MS-Windows operating system, is hereby incorporated by reference in its entirety for all purposes.

TECHNICAL FIELD

The present invention relates to a vesicle having a cavity in which a substance is encapsulated, and also to a process of producing the same.

More specifically, the invention relates to a process of producing a vesicle encapsulating a substance therein (substance-encapsulating vesicle) easily and efficiently, by making the substance carried and encapsulated in the cavity of a vacant vesicle formed via self-assembly of polymers, and also to a novel substance-encapsulating vesicle prepared by the process.

BACKGROUND ART

It is known that a vesicle can be formed via self-assembly of polymers of which the primary structures have been controlled precisely. Such a vesicle is applicable to various molecular designs, and can serve a new function beyond the properties of the original polymers. Accordingly, the vesicle is being considered for use as a carrier for a drug delivery system (DDS) or as a biomaterial or functional material.

Patent Document 1 (JP-H8-188541A, of which the inventors overlap with the present inventors) discloses a drug carrier in the form of an electrostatically-united polymeric micelle formed via self-assembly of a block copolymer having an uncharged segment and a charged segment.

Non-Patent Document 1 (Schlaad H. et al., Macromolecules, 2003, 36 (5), 1417-1420) discloses a vesicle formed via self-assembly of a first block copolymer having poly(1, 2-butadiene) block and poly(cesium methacrylate) block with a second block copolymer having polystyrene block and poly(1-methyl-4-vinylpyridinium iodide) block (referred to as "polymersome").

Patent Document 2 (WO2006/118260A, of which the inventors overlap with the present inventors) discloses a vesicle formed via self-assembly of a first block copolymer having an uncharged hydrophilic segment and a cationic segment (e.g., PEG-polycation) with a second block copolymer having an uncharged hydrophilic segment and an anionic segment (e.g., PEG-polyanion).

Non-Patent Document 2 (Anraku Y. et al., J. Am. Chem. Soc., 2010, 132 (5), 1631-1636, of which the authors overlap with the present inventors) discloses a vesicle formed via self-assembly of a block copolymer having an uncharged hydrophilic segment and a charged segment (e.g., PEG-polycation) and a copolymer charged oppositely to the charged segment of the block copolymer (e.g., polyanion).

It is contemplated that such vesicles formed via self-assembly of polymers as mentioned above can encapsulate and carry various substances within their cavities for desired applications (for overview, see, e.g., Non-Patent Document 3: H. Nyin et al. Soft Matter, 2006, 2, 940-949; and Non-Patent Document 4: "liposome: New Developments in Applications", supervised by Kazunari AKIYOSHI et al., NTS Inc., 2005).

A typical process of producing a vesicle encapsulating a substance within its cavity (hereinafter also referred to as "substance-encapsulating vesicle") includes mixing a substance to be encapsulated (hereinafter also referred to as "encapsulation-target substance") with membrane component polymers or a preformed polymer membrane to cause formation of a polymer vesicle via self-assembly simultaneously with enclosure of the substance into the vesicle cavity (hereinafter also referred to as "simultaneous mixing method"). Examples include: emulsion method (see, e.g., Non-Patent Document 5: F. Szoka, Jr et al., Proc. Natl. Acad. Sci. USA, 1978 75 (9) 4194-4198); and instillation method using organic solution of lipids (see, e.g., Non-Patent Document 6: Batzri, S. et al., Biochim. Biophys Acta 1973, 298, 1015-1019).

However, the simultaneous mixing method has a drawback that presence of the encapsulation-target substance may affect vesicle formation process via self-assembly, thereby preventing formation of a vesicle or, even if not, enclosure of the substance into the vesicle cavity. Another problem involved in this method is that it often requires use of organic solvent which is detrimental to membrane formation, rendering the process complicated and causing damage to the encapsulation-target substance due to the organic solvent. This method has still another drawback that it is difficult to form vesicles having uniform particle size and structure unless carrying out an additional step, which is likely to render the process complicated. Thus, this method lacks versatility, and is not practical as a means for producing various kinds of substance-encapsulating vesicles.

On the other hand, as a general method of producing a particle encapsulating a substance, there is a method in which an encapsulation-target substance is introduced into the cavity of an existing vacant particle such that the substance is enclosed and carried by the particle (hereinafter also referred to as "post-carrying method") (see, e.g., Non-Patent Document 7: W. Tong et al. J. Phys. Chem. B, 2005, 109, 13159-13165). This method could be an option for producing substance-encapsulating vesicles.

However, application of the post-carrying method to vesicles would require any additional means to introduce an encapsulation-target substance beyond the membrane of a vacant vesicle into the vesicle cavity. A conceivable method includes: making the vacant vesicle swell to relax the membrane; penetrating the encapsulation-target substance into the cavity through cleavage which has occurred on the relaxed membrane; and contracting the membrane to prevent release of the encapsulation-target substance. Another conceivable method includes: opening pores on the membrane of the vacant vesicle; introducing the encapsulation-target substance into the cavity through the pores; and closing the pores to prevent release of the encapsulation-target substance. However, these methods are cumbersome and complicated, too disadvantageous to be put into practical use. In addition, the particle size and the structure of the existing vacant vesicle would probably be disturbed during the process of enclosure and carriage of the encapsulation-target substance. Accordingly, these methods have been considered as being far from practical.

Another published method for lipid bilayer membrane vesicles such as liposomes includes integrating a channel protein into the lipid bilayer membrane (see, e.g., Non-Patent Document 8: Ranquin A, Versees W, Miere W, Steyaert J, Gelder P V., "Therapeutic Nanoreactors: Combining Chemistry and Biology in a Novel Triblock Copolymer", Drug Delivery System, Nano Lett., 2005, 5:2220-4). However, this method is not practical either, since the process is cumbersome and complicated and lacks versatility.

Thus, there is a demand for a process of easily and efficiently producing a substance-encapsulating vesicle, in which a substance is encapsulated in the cavity of a vesicle formed via self-assembly of polymers.

With regard to vacant vesicles for encapsulating and carrying an active ingredient in the vesicle cavity, there is still room for improvement in the stability of carriage. In addition, it is still difficult to make two or more active ingredients carried by such a vesicle.

Thus, there is a demand for developing a new vesicle which can carry an active ingredient with improved stability, and can also carry two or more ingredients with improved controllability.

PRIOR ART REFERENCES

Patent Documents

Patent Document 1: JP-H8-188541A
Patent Document 2: WO2006/118260A

Non-Patent Documents

Non-Patent Document 1: Schlaad H. et al., Macromolecules, 2003, 36 (5), 1417-1420
Non-Patent Document 2: Anraku Y. et al., J. Am. Chem. Soc., 2010, 132 (5), 1631-1636
Non-Patent Document 3: H. Nyin et al. Soft Matter, 2006, 2, 940-949
Non-Patent Document 4: "liposome: New Developments in Applications", supervised by Kazunari AKIYOSHI et al., NTS Inc., 2005
Non-Patent Document 5: F. Szoka, Jr. et al., Proc. Natl. Acad. Sci. USA, 1978 75 (9) 4194-4198
Non-Patent Document 6: Batzri, S. et al., Biochim. Biophys Acta 1973, 298, 1015-1019
Non-Patent Document 7: W. Tong et al., J. Phys. Chem. B, 2005, 109, 13159-13165
Non-Patent Document 8: Ranquin A et al., Nano Lett. 2005; 5:2220-4

DISCLOSURE OF THE INVENTION

Problems to be Solved by the Invention

A problem to be addressed by the present invention is to provide a process of producing a substance-encapsulating vesicle easily and efficiently, in which vesicle a substance is encapsulated in the cavity of a vesicle formed via self-assembly of polymers.

Another problem to be addressed by the present invention is to provide a new vesicle which can carry an active ingredient with improved stability, and can also carry two or more ingredients with improved controllability.

Means to Solve the Problems

After intensive investigations in view of the aforementioned problems, the present inventors have finally found that a substance-encapsulating vesicle having a substance encapsulated in the vesicle cavity can be produced by preparing a vacant vesicle having a certain structure, and mixing the vacant vesicle with the encapsulation-target substance in an aqueous medium. This finding is very surprising, since although very simple, this process enables efficient introduction of an encapsulation-target substance into a vacant vesicle using the post-carrying method, without substantially impairing the structure of the vesicle.

In addition, in the course of developing the process, the present inventors have found a novel vesicle of which the membrane contains a nucleic acid.

Thus, an aspect of the present invention relates to a process of producing a substance-encapsulating vesicle, which encapsulates a substance in a cavity thereof, comprising: providing a vacant vesicle having a membrane containing a first polymer, which is a block copolymer having an uncharged hydrophilic segment and a first charged segment, and a second polymer, which has a second charged segment charged oppositely to the first charged segment, said membrane defining a cavity surrounded thereby; and mixing the vacant vesicle and the substance in an aqueous medium.

Another aspect of the present invention relates to a vesicle comprising: a membrane containing a first polymer, which is a block copolymer having an uncharged hydrophilic segment and a first charged segment, and a second polymer, which has a second charged segment charged oppositely to the first charged segment, said membrane defining a cavity surrounded thereby; and a substance encapsulated in the cavity.

Still another aspect of the present invention relates to a vesicle comprising a membrane containing: a block copolymer having an uncharged hydrophilic segment and a cationic segment; and a nucleic acid; said membrane defining a cavity surrounded thereby.

Effects of the Invention

The present invention provides a method which can produces a substance-encapsulating vesicle easily and efficiently, in which vesicle a substance is encapsulated in the cavity of a vesicle formed via self-assembly of polymers. This method also provides a novel substance-encapsulating vesicle having high usefulness.

The present invention also provides a vesicle with a novel structure, having a cavity surrounded by a membrane containing a certain block copolymer and a nucleic acid.

BRIEF EXPLANATION OF THE DRAWINGS

FIGS. 21(a) and (b) are the phase-contrast cryo-transmission electron micrographs of the substance-encapsulating vesicle of Example VII.

MODE FOR CARRYING OUT THE INVENTION

[I: Definition]

Figure 1:
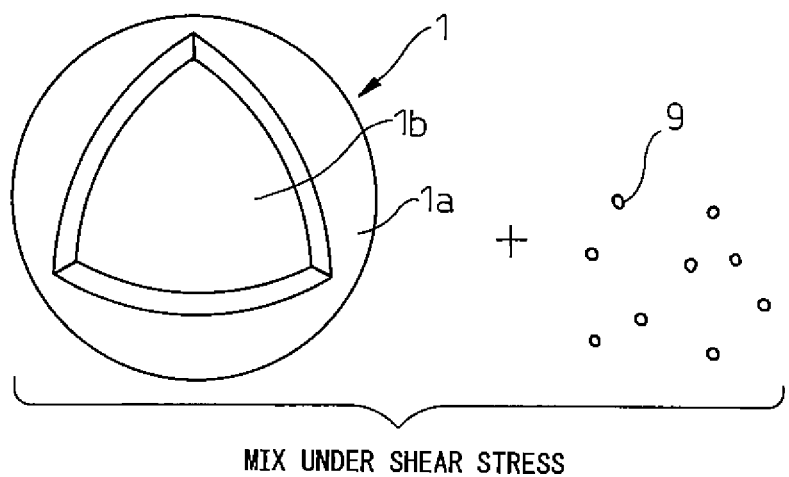
FIGS. 1(a) and (b) are drawings for explaining the method of the present invention.
Figure 1:
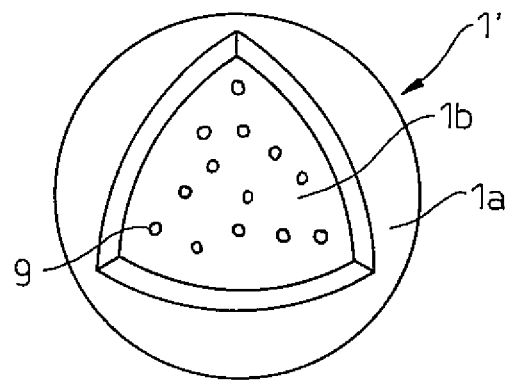

As used herein the term "vesicle" means a basic structure having a membrane of a unilamellar structure and a cavity (internal water phase) surrounded by the membrane.

As used herein the term "alkyl" represents a monovalent aliphatic saturated hydrocarbon group. Unless otherwise specified, alkyl may be a linear or cyclic form, or a form in which a linear and a cyclic form are bound. Linear alkyl may be a straight- or branched-chain. Cyclic alkyl may be monocyclic or polycyclic, and in the case of polycyclic alkyl, it may be a linked or fused ring, or a spiro ring.

As used herein the term "alkoxy" as a name of a group or part thereof represents a group in which the above alkyl is bound to one valence arm of a divalent oxygen atom.

As used herein the term "aryl" as a name of a group or part thereof represents a monovalent aromatic hydrocarbon group. Unless otherwise specified, aryl may be monocyclic or polycyclic, and in the case of polycyclic alkyl, it may be a linked or fused ring or a spiro ring.

As used herein, the number of carbons of a group is expressed as in "$C_{1-12}$ alkyl." "$C_{1-12}$ alkyl" means that the number of carbons of the alkyl is 1 to 12.

As used herein the term "halogen atom" means a fluorine atom, a chlorine atom, a bromine atom, or an iodine atom.

As used herein, that a certain group is "optionally substituted" means that one or more hydrogen atoms contained in the group may be substituted with one or more substituents (in the case of two or more substituents, they may be the same or different). The maximum number of substituents can be easily determined by a person skilled in the art according to the structure and the number of hydrogen atoms contained in the group.

As used herein the "substituent" is selected, unless otherwise specified, from the group consisting of a halogen atom, an aryl group, a hydroxy group, an amino group, a carboxyl group, a cyano group, a formyl group, a dimethylacetal formyl group, a diethylacetal formyl group, a $C_{1-6}$ alkoxycarbonyl group, a $C_{2-7}$ acylamide group, a siloxy group, a tri($C_{1-6}$ alkyl)siloxy group ($C_{1-6}$ alkyl may be the same or different) and a sillylamino group.

As used herein the term "shear stress" means a stress component for which the direction of a normal line of a force acting surface is different from the force acting direction. The description "mixing under shear stress" means mixing so that shear stress is acted on an object to be mixed. When an external force is applied on a fluid (e.g., an aqueous medium) containing an object, "shear stress" usually acts on the object present in the fluid. Thus, when an external force is applied to mix a subject solution described below (a liquid containing a vesicle and an encapsulation-target substance in an aqueous medium), for example, "shear stress" acts on the vesicle contained therein, and thus such mixing corresponds to "mixing under shear stress".

As used herein the term "RNAi" means RNA interference.

As used herein the term "siRNA (small interfering RNA)" means a low molecular weight (usually 19-27 base pairs, preferably 21-23 base pairs) double-stranded RNA involved in RNAi.

Now the embodiments of the present invention will be explained below. The following embodiments are only illustrative examples and the present invention may be carried out in any form.

[II: Method for Producing a Substance-encapsulating Vesicle]

(II-1: Summary)

As described above, in the simultaneous mixing method, which is a representative method for producing a substance-encapsulating vesicle, in addition to being uncertain about the success of encapsulation, it was difficult to secure the stability of an encapsulation-target substance or the uniformity of particle size and structure, and furthermore the process was complicated. Thus, the method had many problems for it to be used as a universal method for producing a variety of substance-encapsulating vesicles. On the other hand, there can be conceived to use a later supporting method which is mainly used for vacant particles. In this case, however, since a substance is introduced into a cavity of a vacant vesicle by transcending the membrane of the vesicle, the method requires complicated procedures such as membrane relaxation by swelling of the vacant vesicle, pore formation in the membrane of the vacant vesicle, and the embedding of channel proteins into lipid bilayers, rendering the process very complicated. Besides it is difficult to control the particle size and structure of the vesicle, the method was considered to be hardly practical.

In contrast, in the method of producing a substance-encapsulating vesicle of the present invention (hereinafter referred to as "the production method of the present invention"), a vacant vesicle of a predetermined structure is provided, which is mixed with an encapsulation-target substance in an aqueous medium to produce a substance-encapsulating vesicle having encapsulated a substance in a cavity thereof. Despite being such a simple method, it can efficiently introduce an encapsulation-target substance into a vacant vesicle even with a later supporting method, and besides vesicle structure is hardly impaired. This is a surprising finding.

The outline of the production method of the present invention will be explained below with reference to FIG. 1. As used herein, FIG. 1 is a schematic diagram, and the present invention is not limited to FIG. 1 in any way.

As shown in FIG. 1($a$), a vacant vesicle 1 with a predetermined structure having a cavity $1b$ surrounded by a membrane $1a$ is provided, which, together with an encapsulation-target substance 9, is mixed in an aqueous medium. Thus, as shown in FIG. 1($b$), the encapsulation-target substance 9 is introduced into the cavity $1b$ by transcending the membrane $1a$ of the vacant vesicle 1, and thereby a substance-encapsulating vesicle 1' encapsulating the encapsulation-target substance 9 in the cavity $1b$ can be obtained.

It is a highly surprising finding that for the vesicle 1 obtained by polymer self-assembly, which requires a highly sophisticated control of the structure, such a simple method can introduce and encapsulate the substance 9 into the cavity $1b$ of the membrane $1a$. The production method of the present invention is based on such a finding.

Now, the production method of the present invention will be explained in detail below, but the details of the vacant vesicle and the encapsulation-target substance will be described in different sections, and here other conditions and procedures will be explained.

(II-2: Mixing of a Vacant Vesicle and an Encapsulation-target Substance)

The production method of the present invention includes a step of mixing a vacant vesicle and an encapsulation-target substance in an aqueous medium (the liquid, a subject to be mixed, containing the vacant vesicle and the encapsulation-target substance may hereinafter be referred to as "a subject solution to be mixed").

The method of mixing may not be specifically limited, and may be carried out by a method of applying an external force to an aqueous medium. Thus, a method in which a vacant vesicle and an encapsulation-target substance are added into an aqueous medium and allowed to stand so as to disperse them spontaneously (hereinafter referred to as "standing/dispersion mixing") is excluded. As an example of mixing by applying an external force to an aqueous medium, there can be mentioned agitation, shaking, impaction etc.

As an exemplary method that employs agitation, there can be mentioned a method of agitating by rotating a container containing a subject solution to be mixed with a vortex mixer etc., and a method of directly agitating the solution with an agitation blade, and the like.

As an exemplary method that employs shaking, there can be mentioned a method of shaking a container containing a subject solution to be mixed with a shaker etc.

As an exemplary method that employs impaction, there can be mentioned a method of applying vibration by ultrasonic irradiation and various other impacts to a subject solution to be mixed, and the like.

By the above mixing, a substance is encapsulated in the cavity of a vesicle and thus a substance-encapsulating vesicle can be produced.

The reason why a substance-encapsulating vesicle can be formed by mixing is not clear, but by applying an external force to an aqueous medium, shear stress is acted on the vacant vesicle (thereby, mixing by an external force application to an aqueous medium may be rephrased as mixing under shear stress). With such shear stress, it is believed, the structure of the vacant vesicle may be disturbed and decomposed to roughly uniform small aggregates, which self-assemble again to uniformly regenerate the vesicle, and at the same time an encapsulation-target substance present in the aqueous medium may be encapsulated into the vesicle during vesicle regeneration (such a mechanism can also be estimated since vesicle decomposition into small aggregates by mixing was also confirmed in a reference experiment described below). This phenomenon can hardly occur for a vesicle at a normal state, and therefore the production method of the present invention that employs such a phenomenon can be considered extremely innovative.

Considering the above mechanism, though the mixing condition is not limited, it is preferred to select an appropriate condition that permits the sufficient disturbance of the vacant vesicle structure in an aqueous medium and permits, after disturbance, the regeneration of the vesicle structure. Usually, mixing may be carried out to the extent that a force may be applied to the entire subject solution to be mixed, and preferably mixing may be carried out to the extent that the entire subject solution to be mixed becomes roughly uniform.

A specific condition for mixing may vary with the mixing method, and in the case of agitating, it may be usually carried out at a rotating speed of 500 rpm or higher, preferably 1000 rpm or higher, and usually 10000 rpm or lower, preferably 5000 rpm or lower. When the rotating speed is too low, a uniform substance-encapsulating vesicle can be hardly formed, whereas when it is too high, a vesicle may be impaired and destroyed.

The agitating time with a vortex mixer may vary with the rotating speed, and may usually be 60 seconds or more, preferably 120 seconds or more, and usually 10 minutes or less, preferably 5 minutes or less. When the agitating time is too short, a uniform substance-encapsulating vesicle can be hardly formed, whereas when it is too long, a vesicle may be impaired and destroyed.

A specific condition for using another mixing method (agitation with an agitation blade, shaking with a shaker, impacting with ultrasonic irradiation etc.) may be adjusted as appropriate so that a force may be applied to a subject solution to be mixed, said force having a similar degree of strength to that obtained when agitation with a vortex mixer is carried out at the above rotating speed and agitation time.

When the above mechanism is taken into account, it is preferred to secure a certain period of time, after mixing, during which the subject solution to be mixed is allowed to stand and the vesicle is uniformly regenerated. Such a standing time is not limited, but may be one minute or more, preferably 3 minutes or more.

The fact that a substance was encapsulated into the cavity of a vesicle can be confirmed by such methods as the detection of changes in diffusion coefficient by fluorescence correlation spectroscopy (FCS), separation by size exclusion chromatography, direct examination by transmission electron microscope, etc. In measurement of diffusion coefficient by fluorescence correlation spectroscopy, the uneven distribution of the encapsulation-target substance in the vesicle (thus the obtainment of a substance-encapsulating vesicle) can be confirmed by measuring changes in diffusion coefficient of a fluorescent sample using a fluorescent sample as the encapsulation-target substance.

(II-3: Other Conditions Related to Mixing)

Usually, a solution (a subject solution to be mixed) containing a vacant vesicle and an encapsulation-target substance in an aqueous medium may be prepared and subjected to the above mixing.

The type of the aqueous solvent is not limited. Preferably it may be water, but a solvent (such as physiological saline, an aqueous buffer solution, and a mixed solvent of water and a water-soluble organic solvent etc.) in which another ingredient was mixed with water can also be used as long as it does not badly affect the structure of a vacant vesicle or does not prevent the introduction of an encapsulation-target substance into the vesicle. As an aqueous buffer solution, a 10 mM HEPES buffer etc. may be used.

While a subject solution to be mixed may be prepared by any procedure, it is preferred that, since a vacant vesicle is prepared in an aqueous medium as described below, an encapsulation-target substance may be added to a prepared vacant vesicle-containing solution, which is then subjected to mixing. The encapsulation-target substance may be added as it is to the vacant vesicle-containing solution, or may be added in the form of a solution in an aqueous medium or of a suspension etc.

The respective concentration of a vacant vesicle and an encapsulation-target substance in the subject solution to be mixed may not be specifically limited, and may be decided considering the structure of the vacant vesicle, the type of the encapsulation-target substance, the desired encapsulation ratio of the encapsulation-target substance to the vacant vesicle, etc.

However, from the viewpoint of enhancing the encapsulation efficiency of an encapsulation-target substance into the vacant vesicle, the concentration of the vacant vesicle in an aqueous medium may usually be 0.1 mg/ml or more, especially 1 mg/ml or more, and usually 100 mg/ml or less, especially 10 mg/ml or less. When the concentration of the vacant vesicle is too low, the substance-encapsulating vesicle may not be formed. Since the particle size of the substance-encapsulating vesicle obtained is believed to depend on the concentration of the vacant vesicle, the concentration of the vacant vesicle should be decided according to the desired particle size of the substance-encapsulating vesicle.

Also, the concentration of the encapsulation-target substance in the aqueous medium, which varies with the property of the encapsulation-target substance, may usually be 0.1 mg/ml or more, especially 1 mg/ml or more, and usually 100 mg/ml or less, especially 50 mg/ml or less. When the concentration of the encapsulation-target substance is too low, the substance-encapsulating vesicle may not be formed.

While the pH of a mixture solution may not be specifically limited, and may be adjusted as appropriate considering the conditions such as the structure of the vacant vesicle, the type of the encapsulation-target substance, and the respective concentration of the vacant vesicle and the encapsulation-target substance in the mixture solution, it may preferably be 5 or higher, more preferably 6.5 or higher, and preferably 9 or lower, more preferably 7.5 or lower. pH may be easily adjusted by using a buffer solution as a solvent. To adjust the pH of the mixture solution and use it may be advantageous in retaining the structure of the vacant vesicle and allowing the vacant vesicle to efficiently encapsulate the encapsulation-target substance.

While the ionic strength of a mixture solution can be adjusted as appropriate as long as it does not destroy the structure of a vacant vesicle or inhibit the encapsulation of an encapsulation-target substance into the vacant vesicle, it may preferably be 0 mM or more, more preferably 10 mM or more, and preferably 200 mM or less, more preferably 50 mM or less.

While the temperature during mixing of a mixture solution may not be limited as long as it does not destroy the structure of a vacant vesicle or inhibit the encapsulation of an encapsulation-target substance into the vacant vesicle, it may preferably be 10° C. or higher, more preferably 20° C. or higher, and preferably 80° C. or lower, more preferably 50° C. or lower.

After mixing, the formed substance-encapsulating vesicle may immediately be subjected to the desired use, or in order to equilibrate the system, time for allowing the mixed liquid to stand may be secured. While the time for allowing the mixture solution to stand may vary depending on the conditions such as the efficiency of forming a substance-encapsulating vesicle, it may preferably be 50 hours or less, more preferably 30 hours or less. When a cross-linker may not be used as described below, it may sometimes be preferred not to allow time longer than is required for uniform regeneration of the vesicle, since the size of the formed substance-encapsulating vesicle may tend to increase with time.

When a cross-linker is used, it may be added to a mixture solution containing the formed substance-encapsulating vesicle, and the cross-linker may be added and mixed. While the cross-linker may be added as it is, an aqueous solution containing the cross-linker may be prepared and this solution may be added. The conditions for preparing an aqueous solvent, pH, temperature, ionic strength etc. in the preparation of an aqueous solution of a cross-linker may be similar to those described above for the mixture solution.

[III: A Vacant Vesicle]

(III-1: Structure of a Vacant Vesicle)

In the production method of the present invention, a vesicle comprising a membrane containing a first polymer, which is a block copolymer having an uncharged hydrophilic segment and a first charged segment, and a second polymer, which has a second charged segment charged oppositely to the first charged segment, said membrane defining a cavity surrounded thereby is used as a vacant vesicle.

An example of the structure of a vacant vesicle will be explained with reference to FIGS. 2-4. Any of FIGS. 2-4 are a schematic diagram, and the present invention is not limited to these drawings in any way.

Figure 2:
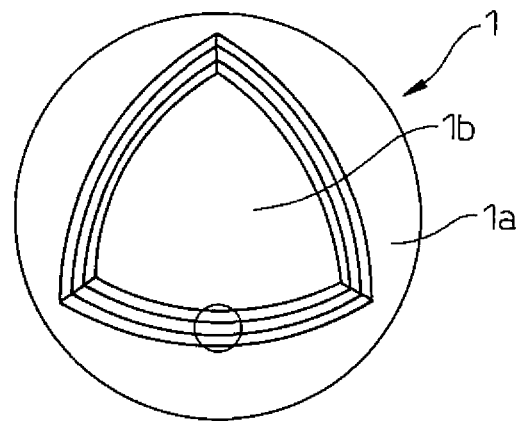
FIG. 2 is a drawing for explaining the structure of a vacant vesicle.

FIG. 2 is a partially broken view of a vesicle 1. As shown in FIG. 2, the vesicle 1 has a membrane 1a and a cavity 1b surrounded by the membrane 1a.

Figure 3:
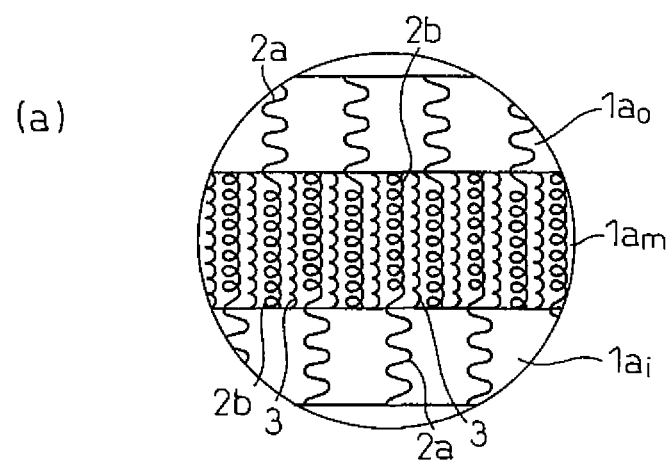
FIGS. 3(a) and (b) are drawings for explaining an embodiment of the membrane structure of a vacant vesicle.
Figure 3:
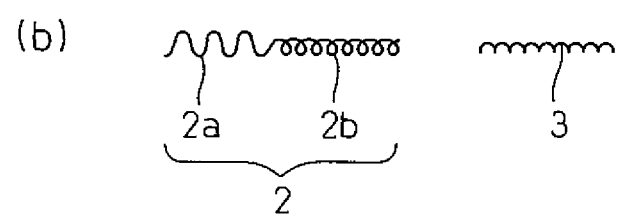
Figure 4:
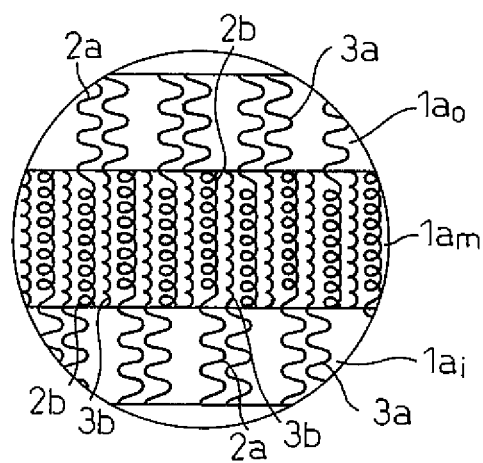
FIGS. 4(a) and (b) are drawings for explaining another embodiment of the membrane structure of a vacant vesicle.
Figure 4:
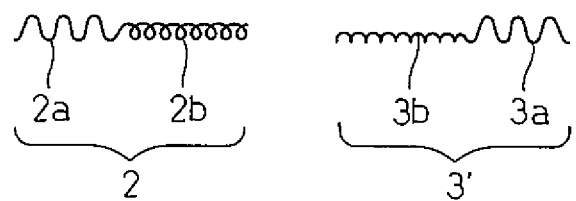

FIG. 3(*a*) is a partially enlarged sectional view of the membrane 1a of the vesicle 1 according to an embodiment of the present invention. The membrane 1a shown in FIG. 3(*a*) has a trilaminar structure comprising an outer layer $1a_o$, an intermediate layer $1a_m$, and an inner layer $1a_i$, and mainly formed by a first polymer 2 and a second polymer 3.

FIG. 3(*b*) is an enlarged view of the first polymer 2 and the second polymer 3 shown in FIG. 3(*a*). As shown in FIG. 3(*b*), the first polymer 2 is a block copolymer having an uncharged hydrophilic segment 2a and a first charged segment 2b, and the second polymer 3 is a polymer that has a second charged segment 3 charged oppositely to the first charged segment 2b. Preferably, as shown in FIG. 3(*a*), the uncharged hydrophilic segment 2a may form the outer layer $1a_o$ of the membrane 1a, and the first charged segment 2b and the second charged segment 3 may be electrostatically bound to form the intermediate layer $1a_m$. And preferably, the uncharged hydrophilic segment $2a$ may mainly form the inner layer $1a_i$ of the membrane $1a$.

FIG. 4(a) is a partially enlarged sectional view of the membrane $1a$ of the vesicle 1 according to an embodiment of the present invention. The membrane $1a$ shown in FIG. 4(a) also has a trilaminar structure comprising the outer layer $1a_o$, the intermediate layer $1a_m$, and the inner layer $1a_i$, and mainly formed by the first polymer 2 and a second polymer 3'.

FIG. 4(b) is an enlarged view of the first polymer 2 and the second polymer 3' shown in FIG. 4(a). As shown in FIG. 4(b), the first polymer 2 is a block copolymer having the uncharged hydrophilic segment $2a$ and the first charged segment $2b$, and the second polymer 3' is a polymer that has the uncharged hydrophilic segment $3a$ and the second charged segment $3b$ charged oppositely to the first charged segment $2b$. Preferably, as shown in FIG. 4(a), one or both of the uncharged hydrophilic segment $2a$ and $3a$ may form the outer layer $1a_o$ of the membrane $1a$, and the first charged segment $2b$ and the second charged segment $3b$ may be electrostatically bound to form the intermediate layer $1a_m$. And preferably, one or both of the uncharged hydrophilic segments $2a$ and $3a$ may form the inner layer $1a_i$ of the membrane $1a$.

It is believed, but not intended to be bound by a theory, that the mechanism in which the vesicle 1 is formed from the first polymer 2 and the second polymer 3 or 3' is as follows. Thus, the first polymer 2 and the second polymer 3 or 3' shown in FIG. 3(b) and FIG. 4(b), when disposed in a system (for example, in an aqueous medium) that can generate the interaction of electric charges, self-assemble, and, as shown in FIG. 3(a) and FIG. 4(a), the first charged segment $2b$ and the second charged segments 3 and $3b$, charged oppositely to each another, are electrostatically bound to form the intermediate layer $1a_m$ and simultaneously the uncharged hydrophilic segments $2a$ and $3a$ are disposed outside thereof forming the outer layer $1a_o$. Preferably, inside the intermediate layer $1a_i$ as well, the uncharged hydrophilic segments $2a$ and $3a$ may be mainly disposed to form the inner layer $1a_i$. Thus, it is believed, the membrane $1a$ of a trilaminar structure shown in FIG. 3(a) and FIG. 4(a) may be formed resulting in the formation of the vesicle 1 shown in FIG. 2.

While the membrane $1a$ of the vesicle 1 may only be formed of the first polymer 2 and the second polymer 3 or 3', it may contain an additional component as long as the above structure may largely be maintained. The additional component may be not limited and may include, for example, a cross-linker, a charged polymer, a charged molecule, etc. The cross-linker will be explained in detail below.

Also, as described below, since the vesicle 1 may usually be prepared in an aqueous medium, and since the inner layer $1a_i$ of the membrane $1a$ may be mainly composed of the uncharged hydrophilic segments $2a$ and $3a$, an aqueous medium may usually be present in the cavity $1b$ of the vesicle 1 (therefore, herein the cavity $1b$ may sometimes be expressed as "internal water phase"). However, another substance may be present in the cavity $1b$.

While the shape of the vesicle 1 may not be limited, it may usually be spherical or roughly spherical.

While the particle size of the vesicle 1 may vary with the type and the mass ratio of the first polymer 2 and the second polymers 3 and 3', the presence or absence of a cross-linker, the environment (the type of the aqueous medium) surrounding the vesicle 1, etc., it may preferably be 10 nm or more, more preferably 50 nm or more, and preferably 1000 nm or less, more preferably 400 nm or less, and even more preferably 200 nm or less.

While the thickness of the membrane $1a$ of the vesicle 1 may vary with the type and the mass ratio of the first polymer 2 and the second polymers 3 and 3', the presence or absence of a cross-linker, the environment (the type of the aqueous medium) surrounding the vesicle 1, etc., it may preferably be 5 nm or more, more preferably 10 nm or more, and preferably 30 nm or less, more preferably 15 nm or less.

(III-2: First and Second Polymers)

A vacant vesicle for use in the production method of the present invention may have a membrane composed of a first polymer and a second polymer.

The first polymer is a block copolymer having an uncharged hydrophilic segment and a first charged segment. The first polymer may be of only one type or two or more types that are used together in any combination or any ratio.

The second polymer is a polymer having a second charged segment charged oppositely to the first charged segment. It may be a polymer composed only of the second charged segment, or may be a block copolymer having an uncharged hydrophilic segment in addition to the second charged segment. The second polymer may be of only one type or two or more types that are used together in any combination or any ratio. When two or more types are used, a second polymer composed only of the second charged segment and a second polymer having an uncharged hydrophilic segment in addition to the second charged segment may be used together.

The first polymer and the second polymer each may have another segment in addition to the above-mentioned segment, respectively.

(III-2a: Uncharged Hydrophilic Segment)

The first polymer has an uncharged hydrophilic segment. The second polymer also has an uncharged hydrophilic segment.

The uncharged hydrophilic segment is a polymer segment having uncharged and hydrophilic properties. As used herein the term "uncharged" indicates that the segment as a whole is neutral. For example, a segment having no positive or negative charge may be mentioned. Also, even if the segment has a positive or negative charge in the molecule, it still corresponds to "uncharged" when the local effective charge density is not high and the electric charge of the segment as a whole has been neutralized to the extent being unable to prevent vesicle formation by self-assembly. "Hydrophilicity" indicates that it exhibits solubility in a sequence medium.

The type of the uncharged hydrophilic segment may not be limited. It may be a segment comprising repeating single units, or a segment containing repeating units of two or more types in any combination or any ratio. As a specific example of the uncharged hydrophilic segment, there can be mentioned polyalkylene glycol, poly(2-oxazoline), polysaccharide, polyvinyl alcohol, polyvinyl pyrrolidone, polyacrylamide, polymethacrylamide, polyacrylate, polymethacrylate, poly(2-methacryloiloxyethyl phosphorylcholine), a peptide or protein or a derivative thereof having an isoelectric point of about 7, and the like. Among them, polyalkylene glycol, poly(2-oxazoline) etc. may be preferred, with polyalkylene glycol being most preferred. As polyalkylene glycol, polyethylene glycol and polypropylene glycol may be mentioned with polyethylene glycol being preferred.

While the molecular weight of the uncharged hydrophilic segment may not be limited, it may preferably have a molecular weight within a predetermined range from the viewpoint of promoting the self-assembly of a first polymer and a second polymer and efficiently producing a uniform vesicle. While the specific range of molecular weight may vary with the type of the uncharged hydrophilic segment or combination with a charged segment, the molecular weight (Mw) may preferably be 500 or more, more preferably 1000 or more, and preferably 15000 or less, more preferably 5000 or less when polyethylene glycol is used as the uncharged hydrophilic segment. While the number of repeating units of the uncharged hydrophilic segment may not be limited, it may usually be decided according to the type of the repeating units so that the molecular weight of the uncharged hydrophilic segment may satisfy the above range of molecular weight.

By using an uncharged hydrophilic segment that satisfies the above condition, it becomes possible to prevent aggregation and precipitation of the first polymer and the second polymer in an aqueous solution, leading to stabilization of the polymers, and to efficiently construct a vesicle.

(III-2b: Charged Segment)

The first charged segment contained in the first polymer and the second charged segment contained in the second polymer are charged segments charged oppositely to each other. Thus, when the first charged segment is a cationic segment, then the second charged segment will be an anionic segment, and when the first charged segment is an anionic segment, then the second charged segment will be a cationic segment.

(III-2b-1: Cationic Segment)

A cationic segment is a polymer segment that has a cationic group and that exhibits a cationic property. However, the cationic segment may have a few anionic groups unless it prevents vesicle formation by the self-assembly of the first polymer and the second polymer.

The type of the cationic segment may not be limited. It may be a segment comprising repeating single units, or a segment containing repeating units of two or more types in any combination or any ratio. As a cationic segment, polyamine etc may be preferred, and a polyamino acid or a derivative thereof having an amino group at the side chain thereof may be specifically preferred. As a polyamino acid or a derivative thereof having an amino group at the side chain thereof, polyaspartamide, polyglutamide, polylysine, polyarginine, polyhistidine, and derivatives thereof may be mentioned, with a polyaspartamide derivative and polyglutamide derivative being most preferred.

While the molecular weight of a cationic segment may not be limited, it may preferably have a molecular weight within a predetermined range from the viewpoint of promoting the self-assembly of a first polymer and a second polymer and efficiently producing a uniform vesicle. While the number of repeating units of the cationic segment may not be limited, it may usually be decided according to the type of the repeating units so that the molecular weight of the cationic segment may satisfy the above range of molecular weight. Specifically when a polyaspartic acid derivative is used as a cationic segment, the number of repeating units thereof may preferably be 10 or more, more preferably 50 or more, and preferably 200 or less, more preferably 100 or less.

By using a cationic segment that satisfies the above condition, it becomes possible to prevent aggregation and precipitation of the first polymer and the second polymer in an aqueous solution leading to the stabilization of the polymers, and to efficiently construct a vesicle.

(III-2b-2: Anionic Segment)

An anionic segment is a polymer segment that has an anionic group and that exhibits an anionic property. However, the anionic segment may have a few anionic groups unless it prevents vesicle formation by the self-assembly of the first polymer and the second polymer.

The type of the anionic segment may not be limited, either. It may be a segment comprising repeating single units, or a segment containing repeating units of two or more types in any combination or any ratio. As an anionic segment, polycarboxylic acid, polysulfonic acid, and polyphosphoric acid (nucleic acid etc.) may be preferred, and a polyamino acid or a derivative thereof having a carboxyl group at the side chain thereof or a derivative thereof may be preferred with nucleic acid being specifically preferred.

As a polyamino acid or a derivative thereof having a carboxyl group at the side chain thereof, polyaspartic acid, polyglutamic acid, polycarboxylic acid obtained by allowing an appropriate amount of aconitic acid anhydride or citraconic acid anhydride to act on the amino group of a polyamino acid, which is the above polycation, or a derivative thereof having an amino group at the side chain, and derivatives thereof may be mentioned, with polyaspartic acid and polyglutamic acid being most preferred.

As a nucleic acid, a single-stranded or double-stranded DNA or RNA may be mentioned. A nucleic acid may be a functional nucleic acid appropriate for use in a vesicle. As a functional nucleic acid, siRNA, miRNA (micro RNA), antisense RNA, antisense DNA, ribozyme, DNA enzyme etc. may be mentioned. They may be selected according to the use of a vesicle. For example, when a vesicle is used as a DDS for RNAi, siRNA may be used as a nucleic acid. A nucleic acid may be modified. As examples of a modified nucleic acid, a nucleic acid to which a hydrophobic functional group such as cholesterol and vitamin E is bound may be mentioned.

While the molecular weight of an anionic segment may not be limited, it may preferably have a molecular weight within a predetermined range from the viewpoint of promoting the self-assembly of a first polymer and a second polymer and efficiently producing a uniform vesicle. While the number of repeating units of the cationic segment may not be limited, it may usually be decided according to the type of the repeating units so that the molecular weight of the anionic segment may satisfy the above range of molecular weight. Specifically when a polycarboxylic acid, polysulfonic acid or nucleic acid is used as an anionic segment, the number of repeating units thereof may preferably be 10 or more, more preferably 50 or more, and preferably 200 or less, more preferably 100 or less.

By using an anionic segment that satisfies the above condition, it becomes possible to prevent aggregation and precipitation of the first polymer and the second polymer in an aqueous solution leading to stabilization of the polymers, and to efficiently construct a vesicle.

(III-2c: Combination of an Uncharged Hydrophilic Segment and a Charged Segment)

The combination of an uncharged hydrophilic segment and a first charged segment contained in the first polymer, and the combination of an uncharged hydrophilic segment and a second charged segment in a case in which the second polymer has an uncharged hydrophilic segment in addition to a second charged segment are both not limited, and any uncharged hydrophilic segment and any charged segment can be combined (in the following description, the first charged segment and the second charged segment may be collectively expressed as "charged segment").

The number of the uncharged hydrophilic segments and that of the charged segments are also arbitrary, and may be one or more. In the case of two or more, they may be the same or different.

While the binding form of an uncharged hydrophilic segment and a charged segment may not be limited, they may be directly bound or may be bound via a linking group.

As an example of a linking group, there can be mentioned a hydrocarbon group having a valency corresponding to the total number of the uncharged hydrophilic segments and the charged segments. The hydrocarbon group as a linking group may be an aliphatic or an aromatic group, or a group in which they are linked, and in the case of an aliphatic group, it may be saturated or unsaturated, and may be straight, branched or circular. While the molecular weight of the hydrocarbon group as a linking group may not be specifically limited, it may usually be 5000 or less, preferably 1000 or less. As an example of a hydrocarbon group as a linking group, a gallic acid derivative, a 3,5-dihydroxy benzoic acid derivative, a glycerin derivative, a cyclohexane derivative, L-lysine etc. may be mentioned, with a 3,5-dihydroxy benzoic acid derivative being preferred.

As an example of a linking group, a disulfide group can be mentioned. A disulfide group may be used to link one uncharged hydrophilic segment and one charged segment. By linking an uncharged hydrophilic segment and a charged segment via a disulfide group, it becomes possible to cleave the disulfide group by the environment surrounding the vesicle or an external action and to alter the form and properties of the vesicle. By using this, it is believed, when a drug is encapsulated in the vesicle and the substance-encapsulating vesicle is used as a DDS for drug delivery, it becomes possible to cleave the disulfide group in vivo and thereby to promote the release of the substance encapsulated in the vesicle.

While the ratio of a first charged segment and a second charged segment (the ratio of a cationic segment and an anionic segment) and the ratio of an uncharged hydrophilic segment and a charged segment are also arbitrary, they may preferably be selected based on the following criteria, from the viewpoint of promoting the self-assembly of a first polymer and a second polymer and efficiently producing a uniform vesicle.

First, the ratio of a cationic segment and an anionic segment may preferably be adjusted so that the C/A ratio defined in the following equation (i) is usually 0.3, preferably 0.5 or more, more preferably 0.6 or more, and usually less than 3.0, preferably 2.0 or less, more preferably 1.7 or less.

[Mathematical 1]

$$\text{C/A ratio (mole ratio)} = \frac{\begin{bmatrix}\text{moles of cationic}\\ \text{groups in the first and}\\ \text{second polymers}\end{bmatrix}}{\begin{bmatrix}\text{moles of anionic groups in}\\ \text{the first and second polymers}\end{bmatrix}} \quad \text{Equation (i)}$$

wherein, the moles of cationic groups and anionic groups in the first and second polymers depend on the structure of the cationic segment and the anionic segment, and can be determined by a common potentiometric (acid/base) titration.

The ratio of the uncharged hydrophilic segment and the charged segment in the first and second polymers may preferably be decided considering the ratio of the cationic segment and the anionic segment that satisfies the above range of the C/A ratio. Specifically, the molecular weight ratio X of the uncharged hydrophilic segment defined by the following equation (ii) may preferably be kept in the range of usually 0.01 or more, preferably 0.05 or more, and usually 0.35 or less, preferably 0.1 or less.

In a case where one each of the cationic segment (assumed to have one positive electric charge per monomer) and the anionic segment (assumed to have one negative electric charge per monomer) is used, and an uncharged hydrophilic segment is introduced into at least one of them (i.e., a case where the first polymer is a block copolymer having a cationic or an anionic segment and an uncharged hydrophilic segment, and the second polymer is a single polymer of an anionic or a cationic segment or a block copolymer having an uncharged hydrophilic segment in addition to it), its X is defined by the following equation:

[Mathematical 2]

$$X = \frac{M_{NA} + M_{NC} * \frac{(C/A\text{比}) * P_A}{P_C}}{M_{NA} + M_A + (M_C + M_{NC}) * \frac{(C/A\text{比}) * P_A}{P_C}} \quad \text{Equation (ii)}$$

$M_M$ represents the molecular weight of the uncharged hydrophilic segment linked to the anionic segment, $M_{NC}$ represents the molecular weight of the uncharged hydrophilic segment linked to the cationic segment, $M_C$ represents the molecular weight of the cationic segment, $M_A$ represents the molecular weight of the anionic segment, $P_C$ represents the degree of polymerization of the cationic segment, and $P_A$ represents the degree of polymerization of the anionic segment.

(III-2d: Specific Examples of the First and Second Polymers)

As specific examples of the first and second polymers, the following [Example 1] and [Example 2] may be mentioned.

EXAMPLE 1

The following (A1) is used as the first polymer and the following (B1) is used as the second polymer.

(A1) A block copolymer having an uncharged hydrophilic segment and an anionic segment.

(B1) A block copolymer of the following (i) and/or a polymer of the following (ii):
(i) A block copolymer having an uncharged hydrophilic segment and a cationic segment.
(ii) A polymer having a cationic segment (but, having no uncharged hydrophilic segment).

EXAMPLE 2

The following (A2) is used as the first polymer and the following (B2) is used as the second polymer.
(A2) A block copolymer having an uncharged hydrophilic segment and an anionic segment.
(B2) A block copolymer of the following (III) and/or a polymer of the following (iv):
(III) A block copolymer having an uncharged hydrophilic segment and an anionic segment.
(iv) A polymer having an anionic segment (but, having no uncharged hydrophilic segment).
As used herein, polymers having no uncharged hydrophilic segment, as in the above (B1) (i) and (ii) and (B2) (iv) polymers, may be called homopolymers for convenience.
While cationic segments in each of the above (B1) (i) and (ii) and (A2) polymers may not be specifically limited, there may preferably be mentioned, for example, those derived from polypeptides having a cationic group at the side chain thereof.
Similarly, while anionic segments in each of the above (A1) and (B2) (III) and (iv) polymers may not be specifically limited, there may preferably be mentioned, for example, those derived from polypeptides or nucleic acids having an anionic group at the side chain thereof.
More specifically, as each block copolymer of the above (A1) and (B2) (III), there can be preferably mentioned, for example, those represented by the following general formula (I) and/or (II):

[Chemical 1]

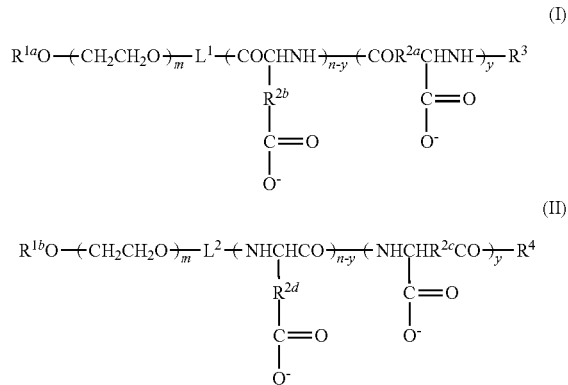

wherein, in the structural formula of the general formulas (I) and (II), the segments having a number (degree of polymerization) of repeating units of "m" are uncharged hydrophilic segments derived from PEG (hereinafter referred to as "PEG segments"), and the segments that combine sections having a number of repeating units of "n-y" and sections having a number of repeating units of "y" are anionic segments derived from polyanions (hereinafter referred to as "polyanionic segments").

In the general formulas (I) and (II), $R^{1a}$ and $R^{1b}$ represent, independently from each other, a hydrogen atom or an unsubstituted or substituted straight or branched $C_{1-12}$ alkyl group. As a straight or branched $C_{1-12}$, there can be mentioned methyl, ethyl, n-propyl, iso-propyl, n-butyl, sec-butyl, tert-butyl, n-pentyl, n-hexyl, decyl, undecyl and the like. As a substituent when they are substituted, there can be mentioned an acetalized formyl group, a cyano group, a formyl group, a carboxyl group, an amino group, a $C_{1-6}$ alkoxycarbonyl group, a $C_{2-7}$ acylamido group, the same or different tri-$C_{1-6}$ alkylsiloxy group, a siloxy group, and a sillylamino group. As used herein acetalization means the formation of an acetal section by the reaction of formyl carbonyl with 2 molecules of alkanol having 1-6 carbons or an optionally branched alkylenediol having 2-6 carbons, and thus is also a method for protecting the carbonyl group. For example, when the substituent is an acetalized formyl group, it can be hydrolyzed under an acidic mild condition to be converted to another substituent, a formyl group (—CHO) (or an aldehyde group).

In the general formulas (I) and (II), $L^1$ and $L^2$ represent a linking group. Specifically, $L^1$ may preferably be —$(CH_2)_b$—NH— (b is an integer of 1-5), and $L_2$ may preferably be —$(CH_2)_c$—CO— (c is an integer of 1-5).

In the general formulas (I) and (II), $R^{2a}$, $R^{2b}$, $R^{2c}$ and $R^{2d}$ represent, independently from each other, a methylene group or an ethylene group. When both of $R^{2a}$ and $R^{2b}$ are a methylene group, they correspond to a poly(aspartic acid derivative), and when they are an ethylene group, they correspond to a poly(glutamic acid derivative), and when both of $R^{2c}$ and $R^{2d}$ are a methylene group, they correspond to a poly(aspartic acid derivative), and when they are an ethylene group, they correspond to a poly(glutamic acid derivative). In these general formulas, when $R^{2a}$ and $R^{2b}$ ($R^{2b}$ and $R^{2a}$) represent both of a methylene group and an ethylene group, and when $R^{2c}$ and $R^{2d}$ ($R^{2d}$ and $R^{2c}$) represent both of a methylene group and an ethylene group, repeating units of the aspartic acid derivative and the glutamic acid derivative can be present by forming a block or can be present at random.

In the general formulas (I) and (II), $R^3$ represents a hydrogen atom, a protecting group, a hydrophobic group or a polymerizable group. Specifically, $R^3$ may preferably be an acetyl group, an acryloyl group, or a mthacryloyl group.

In the general formulas (I) and (II), $R^4$ represents a hydroxyl group, an oxybenzyl group, a —NH—$(CH_2)_a$—X group, or an initiator residue. Herein, a represents an integer of 1-5, and X may preferably be the residue of an amine compound comprising one or more of a primary, secondary, and tertiary amine, a quaternary ammonium salt, and a guanidino group, or may preferably be the residue of a compound other than amine. Furthermore, optionally $R^4$ may preferably be —NH—$R^9$ ($R^9$ represents an unsubstituted or a substituted straight or branched $C_{1-20}$ alkyl group).

In the general formulas (I) and (II), m may be an integer of 5-2,000, preferably an integer of 5-270, and more preferably an integer of 10-100. Also, n represents an integer of 2-5,000, y represents an integer of 0-5,000, and preferably n and y may represent an integer of 5-300, more preferably an integer of 10-100. Provided that y is not greater than n.

While each of the repeating units in the general formulas (I) and (II) is represented according to the order of being specified for the sake of convenience of description, each of the repeating units may be present at a random order. Specifically, it is preferred that each repeating unit in the polyanionic segment can only be present at a random order as described above.

While the molecular weight (Mw) of the block copolymers represented by the general formulas (I) and (II) may not be specifically limited, it may preferably be 3,000-30,000, more preferably 5,000-20,000. For individual segments, the molecular weight (Mw) of the PEG segment may preferably be 500-15,000, more preferably 1,000-5,000, and the molecular weight (Mw) of the polyanionic segment may preferably be 500-50,000, more preferably 1,000-20,000.

While the method for producing the block copolymers represented by the general formulas (I) and (II) may not be specifically limited, there can be mentioned a method, for example, in which a segment (PEG segment) that contains method for producing the PEG segment part of the block copolymer described in, for example, WO96/32434, WO96/33233, WO97/06202, and the like.

As a more specific method for producing the block copolymers represented by the general formula (I) and (II), there can be preferably mentioned a method in which, for example, to the amino terminal of a PEG segment derivative having an amino group at the end, a N-carboxylic acid anhydride (NCA) of a protective amino acid such as β-benzyl-L-aspartate (BLA) and Nε-Z-L-lysine is polymerized to synthesize a block copolymer, and then the side chain of each segment is substituted or converted to become a side chain having the above-mentioned anionic group.

As a specific example of block copolymers represented by the general formulas (I) and (II), there may preferably be mentioned an anionic block copolymer (hereinafter referred to as "PEG-P(Asp)" of the following formula, comprising polyethylene glycol (hereinafter referred to as "PEG"), which is an uncharged hydrophilic segment, and polyaspartic acid (hereinafter referred to as "P(Asp)", which is an anionic segment (in the formulas hereinbelow, Na+ may be indicated as an example of a counter ion, but the counter ion may not be limited to it).

[Chemical 2]

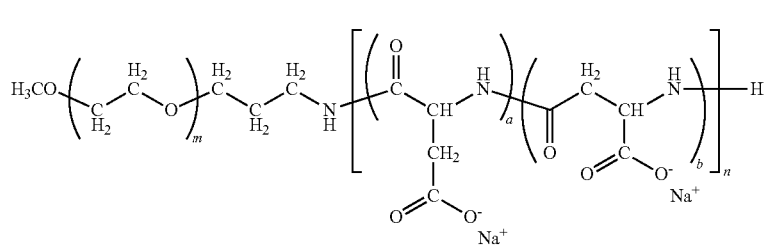

the block part of $R^{1a}o$- or $R^{1b}o$- and a PEG chain is synthesized in advance, to one end (the end opposite to $R^{1a}o$- or $R^{1b}o$-) of the PEG segment, a predetermined monomer is polymerized in order, and then the side chain is substituted or converted, as needed, so as to envelope the anionic group, or a method in which the above PEG segment and a block part having a side chain containing an anionic group are synthesized in advance, and then they are linked to each other. The procedure and condition of various reactions in the above production methods may be selected or designed as appropriate considering the conventional methods. The above PEG segment may be prepared using a wherein, m represents an integer that indicates the degree of polymerization of PEG, n represents an integer that indicates the degree of polymerization of P(Asp), and any of a and b is greater than 0 and less than 1, provided that a+b=1.

As PEG-P(Asp), one that has a molecular weight (Mw) of the PEG segment of 2,000 and a number (n in the above formula) of P(Asp) units of 70 or 75 may be specifically preferred, P(Asp) being a polyanionic segment.

As each block copolymer of the above (A2) and (B1), for example, the one represented by the following general formula (III) and/or (IV) may preferably be mentioned.

[Chemical 3]

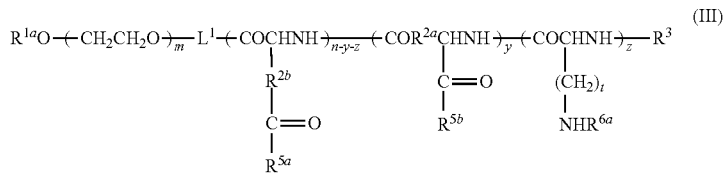

-continued

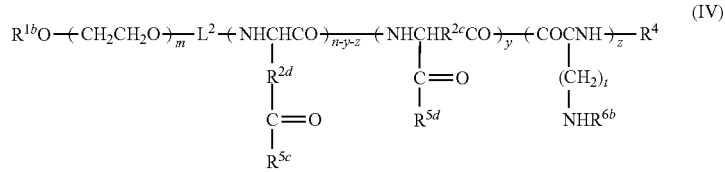

(IV)

Wherein, in the structural formula of the general formulas (III) and (IV), the segments having a number (degree of polymerization) of repeating units of "m" are uncharged hydrophilic segments derived from PEG ("PEG segments"), and the segments that combine the sections having a number of repeating units of "n-y-z" and sections having a number of repeating units of "y" are cationic segments derived from polycations (hereinafter referred to as "polycationic segments").

In the general formulas (III) and (IV), $R^{1a}$ and $R^{1b}$ represent, independently from each other, a hydrogen atom or an unsubstituted or substituted straight or branched $C_{1-12}$ alkyl group. As a straight or branched $C_{1-12}$, there can be mentioned methyl, ethyl, n-propyl, iso-propyl, n-butyl, sec-butyl, tert-butyl, n-pentyl, n-hexyl, decyl, undecyl and the like. As a substituent when they are substituted, there can be mentioned an acetalized formyl group, a cyano group, a formyl group, a carboxyl group, an amino group, a $C_{1-6}$ alkoxycarbonyl group, a $C_{2-7}$ acylamido group, the same or different tri-$C_{1-6}$ alkylsiloxy group, a siloxy group, and a sillylamino group. As used herein acetalization means the formation of an acetal section by the reaction of formyl carbonyl with 2 molecules of alkanol having 1-6 carbons or an optionally branched alkylenediol having 2-6 carbons, and thus is also a method for protecting the carbonyl group. For example, when the substituent is an acetalized formyl group, it can be hydrolyzed under an acidic mild condition to be converted to another substituent, a formyl group (—CHO) (or an aldehyde group).

In the general formulas (III) and (IV), $L^1$ and $L^2$ represent a linking group. Specifically, $L^1$ may preferably be —(CH$_2$)$_b$—NH— (b is an integer of 1-5), and $L^2$ may preferably be —(CH$_2$)$_c$—CO— (c is an integer of 1-5).

In the general formulas (III) and (IV), $R^{2a}$, $R^{2b}$, $R^{2c}$ and $R^{2d}$ represent, independently from each other, a methylene group or an ethylene group. When both of $R^{2a}$ and $R^{2b}$ are a methylene group, they correspond to a poly(aspartic acid derivative), and when they are an ethylene group, they correspond to a poly(glutamic acid derivative), and when both of $R^{2c}$ and $R^{2d}$ are a methylene group, they correspond to a poly(aspartic acid derivative), and when they are an ethylene group, they correspond to a poly(glutamic acid derivative). In these general formulas, when $R^{2a}$ and $R^{2b}$ ($R^{2b}$ and $R^{2a}$) represent both of a methylene group and an ethylene group, and when $R^{2c}$ and $R^{2d}$ ($R^{2d}$ and $R^{2c}$) represent both of a methylene group and an ethylene group, repeating units of the aspartic acid derivative and the glutamic acid derivative can be present by forming a block or can be present at random.

In the general formulas (III) and (IV), $R^3$ represents a hydrogen atom, a protecting group, a hydrophobic group or a polymerizable group. Specifically, $R^3$ may preferably be an acetyl group, an acryloyl group, or a mthacryloyl group.

In the general formulas (III) and (IV), $R^4$ represents a hydroxyl group, an oxybenzyl group, a —NH—(CH$_2$)$_a$—X group, or an initiator residue. Herein, a represents an integer of 1-5, and X may preferably be the residue of an amine compound comprising one or more of a primary, secondary, and tertiary amine, a quaternary ammonium salt, and a guanidino group, or may preferably be the residue of a compound other than amine. Furthermore, optionally $R^4$ may preferably be —NH—$R^9$ ($R^9$ represents an unsubstituted or a substituted straight or branched $C_{1-20}$ alkyl group).

In the general formulas (III) and (IV), $R^{5a}$, $R^{5b}$, $R^{5c}$, and $R^{5d}$ represent, independently from each other, a hydroxyl group, an oxybenzyl group, or a —NH—(CH$_2$)$_a$—X group. Herein, a represents an integer of 1-5, and X may preferably be the residue of an amine compound comprising one or more of a primary, secondary, and tertiary amine, a quaternary ammonium salt, and a guanidino group, or may preferably be the residue of a compound other than amine.

Among the total number of $R^{5a}$ and $R^{5b}$ and the total number of $R^{5c}$ and $R^{5d}$, the presence of at least two —NH—(CH$_2$)$_a$—X groups (X represents (NH(CH$_2$)$_2$)$_e$—NH$_2$ (e is an integer of 0-5)) may be preferred, the presence of 50% or more of the above total number may be more preferred, and the presence of 85% or more of the above total number may be even more preferred.

Also, all or part of $R^{5a}$, $R^{5b}$, $R^{5c}$, and $R^{5d}$ may preferably be —NH—(CH$_2$)$_a$—X group (wherein a represents 2 and X represents (NH(CH$_2$)$_2$)$_e$—NH$_2$ (provided e is 1)).

Furthermore, in the —NH—(CH$_2$)$_a$—X group illustrated as $R^4$, $R^{5a}$, $R^{5b}$, $R^{5c}$, and $R^{5d}$, X selected from the groups represented by each of the following formulas may be most preferred.

[Chemical 4]

[Structures shown: pyridyl, morpholinyl, imidazolyl, piperazinyl, pyrrolidinyl; N-methylanilino, piperidinyl, diisopropylamino with X$^2$;]

—(CH$_2$)$_f$—NH$_2$,  —(NR$^{7a}$(CH$_2$)$_{d1}$)$_{e1}$—NHR$^{8a}$,  —N(CH$_3$)$_2$,

—N(CH$_2$CH$_3$)$_2$,  —(NR$^{7b}$(CH$_2$)$_{d2}$)$_{e2}$—(NR$^{7c}$(CH$_2$)$_{d3}$)$_{e3}$—NHR$^{8b}$,

—(CH$_2$)$_3$CH$_3$,  [phenyl],  or  —NHC(=NH)NH$_2$

In each of the above formulas, X$^2$ represents a hydrogen atom, a $C_{1-6}$ alkyl group or an amino $C_{1-6}$ alkyl group, $R^{7a}$, $R^{7b}$, and $R^{7c}$, independently from each other, represents a hydrogen atom or a methyl group, d1, d2, and d3, independently from each other, represent an integer of 1-5, e1, e2, and e3, independently from each other, represent an integer of 1-5, f represents an integer of 0-15, g represents an integer of 0-15, and $R^{8a}$ and $R^{8b}$, independently from each other, represent a hydrogen atom or a protecting group. Herein, the protecting group may preferably be selected from the group consisting of a Z group, a Boc group, an acetyl group, and a trifluoroacetyl group that are usually used as a protecting group for an amino group.

In the general formulas (III) and (IV), $R^{6a}$ and $R^{6b}$, independently from each other, represent a hydrogen atom, —C(=NH)NH$_2$, or a protecting group, wherein the protecting group may preferably be selected from the group consisting of a Z group, a Boc group, an acetyl group, and a trifluoroacetyl group that are usually used a protecting group for an amino group. Also in the general formulas (III) and (IV), t may preferably represent an integer of 2-6, more preferably 3 or 4.

In the general formulas (III) and (IV), m represents an integer of 5-2,000, preferably an integer of 5-270, and more preferably an integer of 10-100. n represents an integer of 2-5,000, y represents an integer of 0-5,000, and z represents an integer of 0-5,000. n may preferably represent an integer of 5-300, more preferably represent 0 or an integer of 10-100. y and z may preferably represent 0 or an integer of 5-300, more preferably 0 or an integer of 10-100. Provided that the sum of y and z (Y+z) is not greater than n.

While each of the repeating units in the general formulas (III) and (IV) is represented according to the order of being specified for the sake of convenience of description, each of the repeating units may be present at a random order. Specifically, it is preferred that each repeating unit in the polycationic segment can only be present at a random order as described above.

monomer is polymerized in order, and then the side chain is substituted or converted, as needed, so as to envelope the cationic group, or a method in which the above PEG segment and a block part having a side chain containing a cationic group are synthesized in advance, and then they are linked to each other. The procedure and condition of various reactions in the above production methods may be selected or designed as appropriate considering the conventional methods. The above PEG segment may be prepared using a method for producing the PEG segment part of the block copolymer described in, for example, WO96/32434, WO96/33233, WO97/06202, and the like.

As a more specific method for producing the block copolymers represented by the general formulas (III) and (IV), there can be preferably mentioned a method in which, for example, to the amino terminal of a PEG segment derivative having an amino group at the end, a N-carboxylic acid anhydride (NCA) of a protective amino acid such as β-benzyl-L-aspartate (BLA) and Nε-Z-L-lysine is polymerized to synthesize a block copolymer, and then the side chain of each segment is substituted with diethylene triamine (DET) etc. or converted to become a side chain having the above-mentioned cationic group.

As a specific example of block copolymers represented by the general formulas (III) and (IV), there may preferably be mentioned a cationic block copolymer (hereinafter referred to as "PEG-P(Asp-AP)" of the following formula comprising polyethylene glycol (hereinafter referred to as "PEG"), which is an uncharged hydrophilic segment, and poly(diaminopentane structure-containing aspartic acid derivative) (hereinafter referred to as "P(Asp-AP)"), which is a cationic segment (in the formula hereinbelow, Cl$^-$ may be indicated as an example of a counter ion, but the counter ion may not be limited to it).

[Chemical 5]

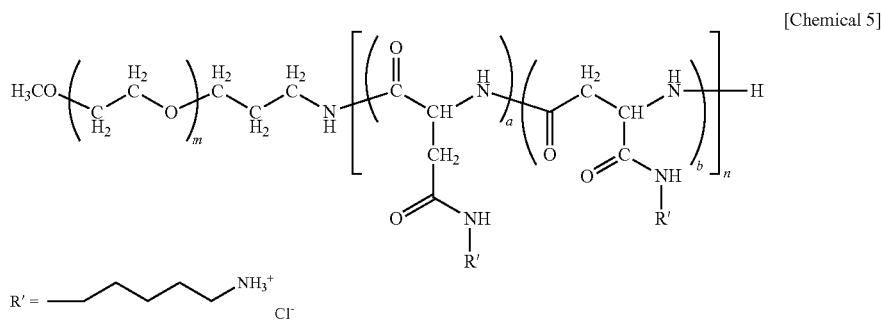

While the molecular weight (Mw) of the block copolymers represented by the general formulas (III) and (IV) may not be specifically limited, it may preferably be 23,000-45,000, more preferably 28,000-34,000. For individual segments, the molecular weight (Mw) of the PEG segment may preferably be 500-15,000, more preferably 1,000-5,000, and the molecular weight (Mw) of the polycationic segment may preferably be altogether 500-50,000, more preferably 1,000-30,000.

While the method for producing the block copolymers represented by the general formulas (III) and (IV) may not be specifically limited, there can be mentioned a method, for example, in which a segment (PEG segment) that contains the block part of $R^{1a}$o- or $R^{1b}$o- and a PEG chain is synthesized in advance, to one end (the end opposite to $R^{1a}$o- or $R^{1b}$o-) of the PEG segment, a predetermined wherein, m represents an integer that indicates the degree of polymerization of PEG, n represents an integer that indicates the degree of polymerization of P(Asp-AP), and any of a and b is greater than 0 and less than 1, provided that a+b=1.

As PEG-P(Asp-AP), one that has a molecular weight (Mw) of the PEG segment of 2,000 and a number (n in the above formula) of P(Asp-AP) units of 70 or 75 may be specifically preferred, P(Asp-AP) being a polycationic segment.

As the polymer of the above (B2) (iv), for example, the one represented by the following general formulas (V) and (VI) may preferably be mentioned. On the explanation of the following general formulas (V) and (VI), the explanation on the above-mentioned general formulas (I) and (II) (excluding the explanation on the PEG segment) may be similarly applied as appropriate.

[Chemical 6]

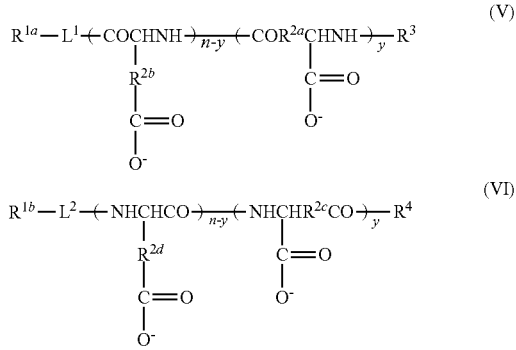

(V)

(VI)

As used herein, as a specific example of polymers represented by the general formulas (V) and (VI), there may preferably be mentioned an anionic homopolymer (hereinafter referred to as "Homo-P(Asp)" of the following formula, comprising polyaspartic acid (P(Asp)), which is an anionic segment.

[Chemical 7]

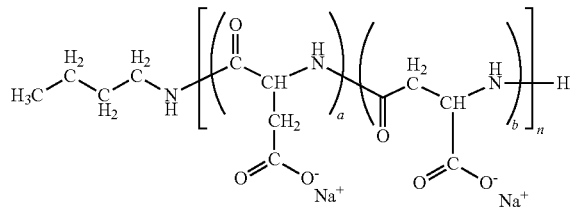

wherein, n represents an integer that indicates the degree of polymerization of P(Asp), and any of a and b is greater than 0 and less than 1, provided that a+b=1.

As Homo-P(Asp), one that has a number (n in the above formula) of P(Asp) units of 70 or 82 may specifically be preferred, P(Asp) being a polyanionic segment.

As each block copolymer of the above (B1) (ii), for example, the one represented by the following general formula (VII) and/or (VIII) may preferably be mentioned. On the explanation of the general formulas (VII) and (VIII), the explanation on the above-mentioned general formulas (III) and (IV) may be similarly applied as appropriate.

[Chemical 8]

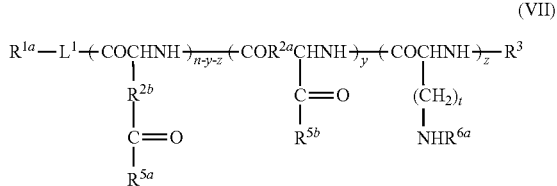

(VII)

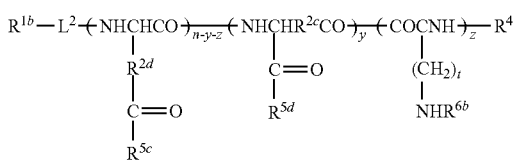

(VIII)

As used herein, as a specific example of polymers represented by the general formulas (VII) and (VIII), there may preferably be mentioned a cationic homopolymer (hereinafter referred to as "Homo-P(Asp-AP)") of the following formula, comprising poly(diaminopentane structure-containing aspartic acid derivative) (P(Asp-AP)), which is a cationic segment.

[Chemical 9]

$R' = $ ───────NH$_3^+$ Cl$^-$ wherein, n represents an integer that indicates the degree of polymerization of P(Asp-AP), and any of a and b is greater than 0 and less than 1, provided that a+b=1.

As Homo-P(Asp-AP), one that has a number (n in the above formula) of P(Asp-AP) units of 70 or 82 may specifically be preferred, P(Asp-AP) being a polycationic segment.

(III-3: Additional Membrane Component)

During the formation of a vacant vesicle, an additional membrane component can be added unless it prevents vesicle formation or reduces stability, in addition to the first polymer and the second polymer. The other membrane component may not be specifically limited, and specific examples thereof may include a charged polymer, a charged nanoparticle and the like.

As the charged polymer, there can be mentioned any charged polymer that has one or more charged segment (a cationic segment or an anionic segment) mentioned above and that does not correspond to the first polymer or the second polymer.

As the charged nanoparticle, a metal-based nanoparticle having an electric charge on the surface etc. may be mentioned.

As the other membrane component mentioned above, a single component may be used alone, or two or more components may be used in any combination or ratio.

Also while the amount used of the other membrane component mentioned above may not be limited, the amount may preferably be kept roughly to a level that does not prevent vesicle formation by the self-assembly of the first polymer and the second polymer. Specifically, relative to the total weight of the vesicle, the amount may usually be 30% or less, preferably 20% or less, and more preferably 10% or less.

(III-4: Method for Producing a Vacant Vesicle)

Since the vacant vesicle for use in the production method of the present invention may be formed using an electrostatic interaction between the first polymer and the second polymer, it can be easily produced by mixing the first polymer and the second polymer in an aqueous solution. Such a production method can produce the vesicle even without using an organic solvent, and thus is advantageous in the field of DDS, biomaterials and the like.

Specifically, a first aqueous solution containing the first polymer and a second aqueous solution containing the second polymer are provided. The first and the second aqueous solutions may be purified by filtration as desired.

The concentration of the first polymer in the first aqueous solution and the concentration of the second polymer in the second aqueous solution may not be limited, and may be determined, as appropriate, by considering the ratio of the total charges of the first polymer and the second polymer, the solubility of the first polymer and the second polymer into the aqueous solutions, conditions such as the efficiency of vesicle formation etc.

The type of the solvent for the first and the second aqueous solutions may not be limited, as long as it is an aqueous solvent. It may preferably be water, but, as long as it does not prevent vesicle formation, there can be used a solvent having another component mixed in water, such as physiological saline, an aqueous buffer, a mixed solvent of water and a water soluble organic solvent etc. As an aqueous buffer, a 10 mM HEPES buffer etc. may be mentioned.

While the pH of the first and the second aqueous solutions may be adjusted as appropriate as long as it does not prevent vesicle formation, it may preferably be pH 5 or higher, more preferably pH 6.5 or higher, and preferably pH 9 or lower, more preferably pH 7.5 or lower. pH can be easily adjusted by using a buffer solution as a solvent. The pH adjustment of the first and second aqueous solutions is advantageous in maintaining the charged state of the first polymer and the second polymer and efficiently forming a vesicle.

While the temperature of the first and second aqueous solutions can be determined as appropriate depending on the solubility in the solvent of the first polymer and the second polymer, it may preferably be 10° C. or higher, more preferably 20° C. or higher, and preferably 80° C. or lower, more preferably 50° C. or lower.

While the ionic strength of the first and second aqueous solutions can be adjusted as appropriate as long as it does not prevent vesicle formation, it may preferably be 0 mM or more, more preferably 10 mM or more, and preferably 200 mM or less, more preferably 50 mM or less.

The above first and second aqueous solutions may be mixed to form a vesicle. The mixing method is not limited, and the second aqueous solution may be added to the first aqueous solution or the first aqueous solution may be added to the second aqueous solution. Also, the first and second aqueous solutions may be simultaneously placed in a vessel for mixing. The mixture of the first and second aqueous solutions may be agitated as appropriate.

While the temperature at the time of mixing of the first and second aqueous solutions is not limited as long as it does not prevent vesicle formation, it can be preferably determined by considering the solubility depending on the temperature of the first polymer and the second polymer. Specifically, it may preferably be 10° C. or higher, more preferably 20° C. or higher, and preferably 60° C. or lower, more preferably 50° C. or lower.

While, after mixing, the vacant vesicle formed may be immediately subjected to the production method of the present invention, time for leaving the mixture to stand may be allowed for in order to equalize the system. However, since the diameter of the vesicle formed may tend to increase over time, it may usually be preferred to subject the vacant vesicle formed to the production method of the present invention without allowing for the standing time.

When another membrane component is used, said membrane component may be mixed with the first and second aqueous solutions. At this time, while this membrane component may be added to the first and second aqueous solutions before mixing, there may preferably be no aggregation or interaction that prevents vesicle formation between the membrane component and the first and second aqueous solutions. Also, the membrane component may be added simultaneously with the mixing of the first and second aqueous solutions, or the mixing of the first and second aqueous solutions may be followed by the addition and further mixing of the membrane component. Another membrane component may be mixed as it is, or an aqueous solution containing the membrane component may be prepared and may be used in mixing. The conditions for preparing an aqueous solution of the membrane component such as an aqueous solvent, pH, temperature, and ionic strength etc. are as described for the first and second aqueous solutions.

Furthermore, a procedure such as dialysis, dilution, concentration, and agitation may be added as appropriate.

[IV: Encapsulation-target Substance]

The encapsulation-target substance for use in the production method of the present invention may not be specifically limited, and any substance-encapsulating vesicles can be selected as appropriate depending on the uses and properties of the substance-encapsulating vesicle.

Specifically, according to a simultaneous mixing method which is one of the conventional production method, there was a problem that when a charged substance was used as an encapsulation-target substance, vesicle formation by the self-assembly of polymers that are a membrane component is prevented by the electric charge of the encapsulation-target substance, and thus an appropriate substance-encapsulating vesicle could not be obtained. According to the production method of the present invention, however, there is no such limitation on the electric properties of the encapsulation-target substance, and thus even when a charged substance was used as the encapsulation-target substance, a substance-encapsulating vesicle can be efficiently formed.

Specifically, as the type of the encapsulation-target substance, there can be mentioned a biomaterial, an organic compound, an inorganic substance and the like.

As the biomaterial, there can be mentioned protein, polypeptide, amino acid, nucleic acid (DNA, RNA), lipid (fatty acid, glyceride, steroid etc.), carbohydrate (monosaccharide, polysaccharide), and a derivative thereof, as well as two or more of them bound together (glycoprotein, glycolipid, etc.). Among them, protein, carbohydrate etc. may be preferred.

As the organic compound, there can be mentioned a light-emitting (fluorescent, phosphorescen) molecule, a water soluble drug, a water soluble polymer, a water soluble molecular self-assembly (micelle, vesicle, nanogel, etc.) with a mean particle size of 100 nm or less, an emulsion with a mean particle size of 100 nm or less, and the like. Among them, a polymer micelle with a mean particle size of 50 nm or less and a water soluble polymer with a molecular weight of 100,000 or less may be preferred.

As the inorganic substance, there can be mentioned a water-dispersible metal nanoparticle, an oxide nanoparticle (a silica nanoparticle, a titania nanoparticle, an iron oxide nanoparticle etc.), a semiconductor nanoparticle (a quantum dot etc.), a water soluble carbon cluster, a boron cluster, a metal complex and the like. Among them, a quantum dot with a mean particle size of 20 nm or less may be preferred.

As the encapsulation-target substance, by classifying by use, there can be mentioned an anti-cancer agent (for example, a hydrophobic anti-cancer agent such as doxorubicin and paclitaxel, a metal complex anti-cancer agent such as cisplatin etc., and a polymer micelle thereof), a gadolinium and iron compound used in diagnostic MRI etc., an organic light-emitting (fluorescent, phosphorescen) dye, a quantum dot and the like.

While the molecular weight or particle size of the encapsulation-target substance is not limited, the molecular weight of the encapsulation-target substance may usually be 200,000 or less, especially 100,000 or less, and the particle size of the encapsulation-target substance may usually be 100 nm or less, most preferably 50 nm or less, from the viewpoint of efficiently introducing an encapsulation-target substance into the vacant vesicle.

The ratio of the encapsulation-target substance used relative to the vacant vesicle may be adjusted according to the desired amount of the encapsulation-target substance as long as it does not destroy the vacant vesicle structure or prevent the encapsulation of the encapsulation-target substance into the vacant vesicle.

Only one type of the encapsulation-target substance may be used alone, or two or more types may be used in any ratio and combination.

[V: Additional Step]

While the production method of the present invention may only require a step of providing a vacant vesicle having a predetermined structure and mixing the vacant vesicle with an encapsulation-target substance in an aqueous medium, it may further have an additional step. Examples include treatment with a cross-linker, filtration, dialysis, lyophilization etc.

Among them, when the substance-encapsulating vesicle is used in a physiological environment or in the presence of a salt such as physiological saline (for example, when used as a DDS), the formed substance-encapsulating vesicle may preferably be subjected to treatment with a cross-linker as a post-treatment, from the viewpoint of preventing an increase in particle size with time. Thus, in a physiological environment or in the presence of a salt such as physiological saline, the particle size of the vesicle having no cross-linker may tend to increase with time, but treatment with a cross-linker can prevent the increase in particle size.

While the type of the cross-linker is not limited, and may be selected, as appropriate, according to the use of the vesicle, the type of the first polymer and the second polymer, the type of another membrane component and the like, the cross-linker may preferably react with charged groups (for example, a cationic group such as an amino group and an anionic group such as a carboxyl group) contained in the charged segment of the first polymer and the second polymer but not with the encapsulation-target substance, from the viewpoint of efficiently conducting crosslinking and enhancing the stability of the substance-encapsulating vesicle. As a specific example of the cross-linker, there can be mentioned a cross-linker having an amino group (for example, glutaraldehyde, dimethyl suberimidate dihydrochloride (DMS), dimethyl 3,3'-dithiobispropionimidate (DTBP)), a cross-linker (for example, 1-ethyl-3-(3-dimethylaminopropy)carbodiimide (EDC)) that conducts crosslinking by fusing an amino group and a carboxyl group, with glutaraldehyde and EDC etc. being preferred and EDC being most preferred.

While a single cross-linker may be used alone, two or more types of crosslinking agent may be used in any combination or ratio.

The amount used of a cross-linker is not limited, and may be selected, as appropriate, by considering the type of the cross-linker, the number of crosslinking points, the amount of the component to be crosslinked, and the like. In the case of a cross-linker, for example, that crosslinks an amino group and a carboxyl group, the amount used may preferably be selected so that the CL ratio defined by the following equation (iii) can satisfy the conditions described below:

[Mathematical 3]

$$CL \text{ ratio (mole ratio)} = \frac{[\text{moles of a cross-linker}]}{\begin{bmatrix} \text{moles of carboxyl groups} \\ \text{contained in the first polymer} \\ \text{and the second polymer} \end{bmatrix}} \quad \text{Equation (iii)}$$

From the viewpoint of efficiently conducting crosslinking and enhancing the stability of the substance-encapsulating vesicle, the mass ratio of the cross-linker and the first and the second polymers may preferably be adjusted so as to give a CL ratio of usually 0.1 or more, preferably 0.5 or more. On the other hand, when a substance-encapsulating vesicle is used as a DDS in drug delivery (for example, when used), the amount used of the cross-linker may preferably be not too much, from the viewpoint of allowing a drug to be efficiently released at the target site, and specifically the mass ratio of the cross-linker and the first and the second polymers may preferably be adjusted so as to give a CL ratio of usually 10 or less, preferably 5 or lower. However, the above range of the CL ratio is a rough measure, and in reality the CL ratio may preferably be adjusted as appropriate according to the use of the vesicle, the type of the first polymer and the second polymer, the type of the other membrane component and the like.

[VI: Substance-encapsulating Vesicle]

In accordance with the production method of the present invention, a substance-encapsulating vesicle that encapsulates an encapsulation-target substance in the cavity of the above vacant vesicle can be obtained.

The substance-encapsulating vesicle produced by the production method of the present invention (hereinafter referred to as the substance-encapsulating vesicle of the present invention) comprises a membrane formed from a first polymer, which is a block copolymer having an uncharged hydrophilic segment and a first charged segment, and a second polymer, which has a second charged segment charged oppositely to the first charged segment, a cavity surrounded by the above membrane, and a substance encapsulated in the cavity.

The structure of the membrane of the substance-encapsulating vesicle of the present invention is essentially equal to the structure of the membrane of the above-mentioned vacant vesicle. Thus, the substance-encapsulating vesicle of the present invention may preferably have a trilaminar structure similar to the structural membrane of the vacant vesicle explained using FIGS. 2-4, and the shape thereof may usually be spherical or roughly spherical.

The particle size of the substance-encapsulating vesicle of the present invention may vary with the conditions such as the structure of the vacant vesicle, the type of the encapsulation-target substance, the environment surrounding the vesicle (the type of an aqueous medium), mixing etc., usually it may roughly be the same as the particle size of the vacant vesicle. Specifically the particle size of the substance-encapsulating vesicle of the present invention may preferably be 10 nm or more, more preferably 50 nm or more, and preferably 1000 nm or less, more preferably 400 nm or less, and even more preferably 200 nm or less.

The membrane thickness of the substance-encapsulating vesicle of the present invention may also vary with the conditions such as the structure of the vacant vesicle, the type of the encapsulation-target substance, the environment surrounding the vesicle (the type of the aqueous medium), mixing etc., usually it may roughly be the same the particle size and the membrane thickness of the vacant vesicle. Specifically the membrane thickness of the substance-encapsulating vesicle of the present invention may preferably be 5 nm or more, more preferably 10 nm or more, and preferably 30 nm or less, more preferably 15 nm or less.

While, in the conventional methods, it was partly possible to encapsulate a substance in an electrostatically interacting vesicle (PICsome), though there was limitation in the range of application. Also, it was difficult or impossible to allow the substance to be encapsulated into the vesicle at a later time. In accordance with the production method of the present invention, it may become possible to produce a substance-encapsulating and electrostatically interacting vesicle (PICsome) that was allowed to encapsulate a wide range of substances in an electrostatically interacting vesicle (PICsome).

Since the substance-encapsulating vesicle of the present invention stably retains various substances in the cavity of the vesicle formed by polymer self-assembly, it can be effectively used as a DDS or in various uses of functional materials having an active ingredient. For example, by using siRNA (small interfering RNA) as a constituent of an encapsulation-target substance or of the vesicle membrane, the substance-encapsulating vesicle obtained can be used as a DDS etc. for RNAi (RNA interference). It is also possible to allow a plurality of drugs to be encapsulated as an encapsulation-target substance, or to use the vesicle in a combined drug therapy by using together as an encapsulation-target substance and a membrane material.

Since the substance-encapsulating vesicle of the present invention is novel, and expands the range of application of PICsome with a mean particle size of 100-200 nm exhibiting excellent blood retention and tumor accumulation, it is highly useful.

[VII: Intra-membrane Nucleic Acid-containing Vesicle]

In a vacant vesicle used in the production method of the present invention, the vesicle in which the first polymer is a block copolymer having an uncharged hydrophilic segment and a cationic segment (thus, the first charged segment is a cationic segment) and the second polymer is a polymer having nucleic acid as an anionic segment (thus, the second charged segment has nucleic acid as an anionic segment) is a vesicle having a novel structure in which the cavity is surrounded by a membrane comprising a predetermined block copolymer and nucleic acid. Such a vesicle (hereinafter referred to as an "intra-membrane nucleic acid-containing vesicle") per se is useful as a DDS for delivering nucleic acid or as a biomaterial or functional material having nucleic acid as an active ingredient. Also, by using such an intra-membrane nucleic acid-containing vesicle as a vacant vesicle in the above production method of the present invention, it can be made into a substance-encapsulating vesicle that contains nucleic acid in the membrane and encapsulates another drug in the cavity, and thus may also be useful as a DDS for delivering nucleic acid and another drug in combination.

Now, such an intra-membrane nucleic acid-containing vesicle will be explained below.

[VII-1: Structure of an Intra-membrane Nucleic Acid-containing Vesicle]

The structure of an intra-membrane nucleic acid-containing vesicle 10 will be explained with reference to FIG. 5(a)-(c). Any of FIG. 5(a)-(c) is a schematic diagram and the present invention is not limited to these figures in any way.

Figure 5:
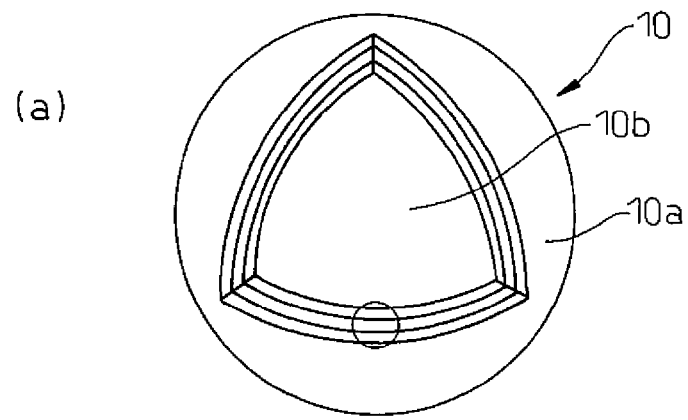
FIGS. 5(a) to (c) are drawings for explaining an embodiment of the membrane structure of an intra-membrane nucleic acid-containing vesicle.
Figure 5:
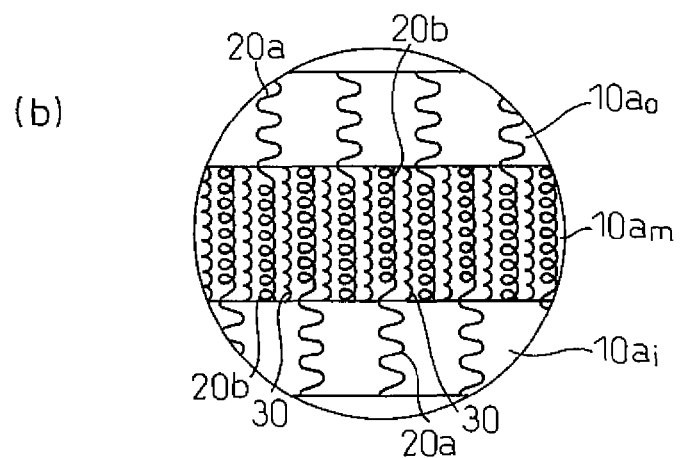
Figure 5:
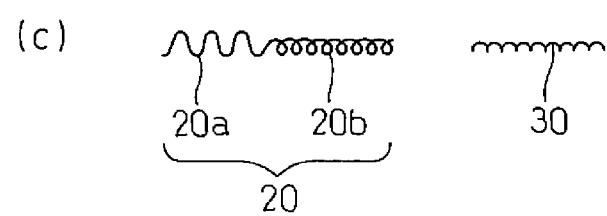

FIG. 5(a) is a partially broken view of a intra-membrane nucleic acid-containing vesicle 10. As shown in FIG. 5(a), the intra-membrane nucleic acid-containing vesicle 10 has a membrane 10a and a cavity 10b surrounded by the membrane 10a.

FIG. 5(b) is a partially broken enlarged view of the membrane 10a of the intra-membrane nucleic acid-containing vesicle 10. As shown in FIG. 5(b), the membrane 10a has a trilaminar structure comprising an outer layer $10a_o$, an intermediate layer $10a_m$, and an inner layer $10a_i$, and mainly formed by a block copolymer 20 and nucleic acid 30.

FIG. 5(c) is an enlarged view of a block copolymer 20 and a nucleic acid 30. As shown in FIG. 5(c), the block copolymer 20 has an uncharged hydrophilic segment 20a and a cationic segment 20b.

It is believed, but not intended to be bound by a theory, that the mechanism in which an intra-membrane nucleic acid-containing vesicle 10 is formed from a block copolymer 20 and a nucleic acid 30 is as follows. Thus, when the block copolymer 20 and the nucleic acid 30 shown in FIG. 5(c) are disposed in a system (for example, in an aqueous medium) that can generate the interaction of electric charges, they self-assemble, and, as shown in FIG. 5(b), the positively charged segment 20b and the negatively charged nucleic acid 30 are electrostatically bound to form an intermediate layer $10a_m$, and simultaneously an uncharged hydrophilic segment 20a may be disposed outside thereof forming an outer layer $10a_o$. Preferably, inside the intermediate layer $10a_m$ as well, the uncharged hydrophilic segment 20a is disposed to form an inner layer $10a_i$. Thus, it is believed, the membrane 10a of a trilaminar structure shown in FIG. 5(a) is thus formed, resulting in the formation of the intra-membrane nucleic acid-containing vesicle 10 shown in FIG. 5(a).

Thus, according to a preferred embodiment, as shown in FIG. 5(b), the uncharged hydrophilic segment 20a forms the outer layer $10a_o$ of the membrane 10a, and the cationic segment 20b and the nucleic acid 30 electrostatically bind to form the intermediate layer $10a_m$. More preferably, the uncharged hydrophilic segment 20a mainly forms the inner layer $10a_i$ of the membrane 10a.

While the membrane 10a of the intra-membrane nucleic acid-containing vesicle 10 may only comprise the block copolymer 20 and the nucleic acid 30, it may contain another component in addition to the block copolymer 20 and the nucleic acid 30, as long as the following structure may be mostly retained. The other component is not limited, and, for example, a cross-linker, a charged polymer, and a charged molecule etc. may be mentioned. The cross-linker will be explained in detail below.

Also, since the intra-membrane nucleic acid-containing vesicle 10 may usually be prepared in an aqueous medium as described below, and the inner layer $10a_i$ of the membrane 10a may preferably be composed mainly of the uncharged hydrophilic segment 20a, as described below, an aqueous medium may usually be present in the cavity 10b of the intra-membrane nucleic acid-containing vesicle 10 (thus, as used herein the cavity 10b may sometimes be expressed as "internal water phase"). However, another substance may be present in the cavity 10b. Specifically, when the intra-membrane nucleic acid-containing vesicle 10 is used as a DDS etc., a drug may be contained in the cavity 10b. The embodiment of encapsulating a drug will be explained in detail below.

While the shape of the intra-membrane nucleic acid-containing vesicle 10 may not be limited, it may be spherical or roughly spherical.

While the particle size of the intra-membrane nucleic acid-containing vesicle 10 may vary with the type and mass ratio of the block copolymer 20 and the nucleic acid 30, the presence of a cross-linker, the environment (the type of an aqueous medium) surrounding the intra-membrane nucleic acid-containing vesicle 10 etc., it may preferably be 10 nm or more, more preferably 50 nm or more, and preferably 200 nm or less, more preferably 150 nm or less. In a physiological environment or in the presence of a salt such as physiological saline, as exemplified in the Example, the particle size of the intra-membrane nucleic acid-containing vesicle 10 having no cross-linker may tend to increase with time, but by introducing a cross-linker, an increase in particle size can be prevented.

While the membrane thickness of the intra-membrane nucleic acid-containing vesicle 10a may vary with the type and mass ratio of the block copolymer 20 and the nucleic acid 30, the presence of a cross-linker, the environment (the type of the aqueous medium) surrounding the intra-membrane nucleic acid-containing vesicle 10 etc., it may preferably be 5 nm or more, more preferably 10 nm or more, and preferably 30 nm or less, more preferably 20 nm or less.

[VII-2: Block Copolymer]

A block copolymer used in an intra-membrane nucleic acid-containing vesicle has an uncharged hydrophilic segment and a cationic segment.

(VII-2a: Uncharged Hydrophilic Segment)

Details of an uncharged hydrophilic segment used in the intra-membrane nucleic acid-containing vesicle are identical to the details on the uncharged hydrophilic segment used in the vacant vesicle explained in the above section (III-2a: Uncharged hydrophilic segment).

(VII-2b: Cationic Segment)

Details of a cationic segment used in the intra-membrane nucleic acid-containing vesicle are identical to the details on the cationic segment used in the vacant vesicle explained in the above section (III-2b-1: Cationic segment).

(VII-2c: Combination of an Uncharged Hydrophilic Segment and a Cationic Segment)

The combination of an uncharged hydrophilic segment and a cationic segment used in the intra-membrane nucleic acid-containing vesicle is not limited, and any uncharged hydrophilic segment and any cationic segment can be combined.

The numbers of the uncharged hydrophilic segment and the cationic segment are also arbitrary, and may each be one or more, and in the case of more than one, they may be the same or different. Usually, one cationic segment may preferably be bound relative to one uncharged hydrophilic segment. However, from the viewpoint of retaining a large amount of nucleic acid in the vesicle, an embodiment in which more than one cationic segment is bound to one uncharged hydrophilic segment may also be preferred.

The binding form of an uncharged hydrophilic segment and a cationic segment is not limited, and they may be directly bound or may be bound via a linking group.

As an example of a linking group, a hydrocarbon group having a valency corresponding to the total number of the uncharged hydrophilic segments and the cationic segments may be mentioned. The hydrocarbon group as a linking group may be aliphatic or aromatic, or a linked body thereof. When it is aliphatic, it may be saturated or unsaturated, and may be straight or branched or circular. While the molecular weight of a hydrocarbon group as a linking group is not limited, it may usually be 5000 or less, preferably 1000 or less. As an example of a hydrocarbon group as a linking group, a gallic acid derivative, a 3,5-dihydroxy benzoic acid derivative, a glycerin derivative, a cyclohexane derivative, a L-lysine etc. may be mentioned with a 3,5-dihydroxy benzoic acid derivative being preferred.

As another example of a linking group, a disulfide group may be mentioned. The disulfide group is used to link one uncharged hydrophilic segment and one cationic segment. By linking an uncharged hydrophilic segment and a cationic segment via a disulfide group, it becomes possible to break up the disulfide group by the environment in which the vesicles were placed or by an external action to change the shape and property of the vesicle. By using this, for example when a vesicle is used as a DDS for delivering nucleic acid, it is thought to become possible to break up the disulfide group in vivo, thereby promoting the release of nucleic acid constituting the vesicle membrane or a drug (the embodiment will be explained below) encapsulated in the vesicle.

While the ratio of the uncharged hydrophilic segment and the cationic segment is also arbitrary, it is preferred that the molecular weight ratio of the uncharged hydrophilic segment contained in the vesicle may be brought into a predetermined range, from the viewpoint of promoting the self-assembly of a block copolymer and nucleic acids and efficiently producing a uniform vesicle. A specific ratio will be explained below in the section of (VII-3: Nucleic acid) since it may be preferred to determine considering the amount of nucleic acid.

(VII-2d: Specific Example of a Block Copolymer)

As a preferred specific example of a block copolymer used in the intra-membrane nucleic acid-containing vesicle, one represented by the following formula (IX) may be mentioned:

[Chemical 10]

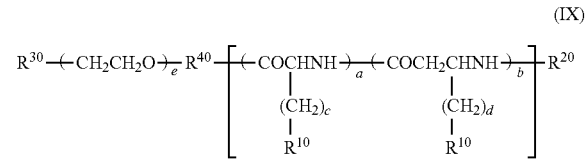

(IX)

In the formula (IX), $R^{10}$ represents $-(CH_2)_3NH_2$, $-(CH_2)_2NHC(=NH)NH_2$, or $-CONH(CH_2)_s-X$,

[wherein, s represents an integer of 0-20,

X is selected from the group consisting of $-NH_2$, a pyridyl group, a morpholyl group, a piperazinyl group, a 1-imidazolyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group, a piperidinyl group, a diisopropylamino group, a dimethylamino group, a diethylamino group, $-(CH_2)_tNHR^{60}$, and $-(NR^{50}(CH_2)_o)_pNHR^{60}$ (wherein, $R^{50}$ represents a hydrogen atom or a methyl group, $R^{60}$ represents a hydrogen atom, an acetyl group, a trifluoroacetyl group, a benzyloxycarbonyl group, or a tert-butoxycarbonyl group, or a guanidino group, o represents an integer of 1-5, p represents an integer of 1-5, and t represents an integer of 0-15)], $R^{20}$ represents a hydrogen atom, an acetyl group, a trifluoroacetyl group, an acryloyl group or a methacryloyl group, a cholesterol derivative group, an acyl group having 3-13 carbons, or a guanidino group (—C(=NH)NH$_2$), $R^{30}$ represents a hydrogen atom, or an optionally substituted $C_{1-12}$ alkyl group, $R^{40}$ represents —(CH$_2$)$_g$R$^{70}$NH— (g represents an integer of 0-12) wherein $R^{70}$ represents a straight or branched $C_{1-12}$ alkyl, a is an integer of 0-5,000 b is an integer of 0-5,000, provided that a+b is 2-5,000, c is an integer of 0-20, d is 0 or an integer satisfying c-1, and e is an integer of 5-2,500.

In the formula (IX), when $R^{10}$ represents —CONH(CH$_2$)$_s$—X, X may be the same functional group for each repeating unit of the block copolymer or may be a different functional group.

Among them, as the block copolymer of the present invention, one in which, in the formula (IX), $R^{10}$ represents a —CONH(CH$_2$)$_s$—NH$_2$ group, s represents an integer of 2-5, $R^{20}$ represents a hydrogen atom, $R^{30}$ represents a methyl group, a represents an integer of 0-200, b represents an integer of 0-200 provided that a+b represents 10-200, and e represents an integer of 10-300 may be specifically preferred.

(VII-3: Nucleic Acid)

A nucleic acid used in an intra-membrane nucleic acid-containing vesicle is not limited and may be selected, as appropriate, according to the use and property of the intra-membrane nucleic acid-containing vesicle.

Thus, the nucleic acid may be single-stranded or double-stranded, and may be DNA or RNA. The presence or absence of protein coding or other functions is not limited, either. Considering the use of the vesicle, however, it may preferably be a functional nucleic acid. As a functional nucleic acid, siRNA, miRNA (micro RNA), antisense RNA, antisense DNA, ribozyme, DNA enzyme etc. can be mentioned. They are selected according to the use of the vesicle. For example, when the vesicle is used as a DDS for RNAi, siRNA is used as the nucleic acid.

The nucleic acid may be modified. As examples of a modified nucleic acid, a nucleic acid to which a hydrophobic functional group such as cholesterol or vitamin E has been bound may be mentioned for use in vesicle stabilization etc.

The number of bases of the nucleic acid may not be specifically limited, and the range of usually 9 or more, preferably 12 or more, and more preferably 19 or more, and usually 100 or less, preferably 40 or less, and more preferably 27 or less may be preferred. Specifically when siRNA is used as the nucleic acid, the number of bases is as described above, and usually 19-27, preferably 21-23.

One type of the nucleic acid may be used alone, or two or more may be used in any combination or ratio.

The amount used of the nucleic acid is not limited, and, from the viewpoint of promoting the self-assembly of a block copolymer and a nucleic acid to efficiently produce a uniform vesicle, the amount used may preferably be selected so that the N$^+$/P ratio defined in the following equation (iv) may satisfy the condition explained below.

[Mathematical 4]

$$N^+/P \text{ ratio (mole ratio)} = \frac{\begin{bmatrix} \text{moles of protonated} \\ \text{amino groups in the block} \\ \text{copolymer} \end{bmatrix}}{\begin{bmatrix} \text{moles of phosphate} \\ \text{groups in} \\ \text{the nucleic acid} \end{bmatrix}} \quad \text{Equation (iv)}$$

wherein, while the moles of protonated amino groups in the block copolymer represents a value dependent on the structure of the cationic segment of the block copolymer, it can be determined by a common potentiometric (acid/base) titration.

The value of N$^+$/P ratio may be usually in the range of greater than 1.0, preferably 1.05 or more, more preferably 1.1 or more, and usually less than 3.0, preferably 2.8 or less, more preferably 2.5 or less. Thus the mass ratio of the nucleic acid and the block copolymer may preferably be adjusted so that the value of the N$^+$/P ratio may satisfy the above range.

However, the preferred value of the N$^+$/P ratio may differ depending on various conditions. For example, when an unmodified nucleic acid is used as the nucleic acid, the value of the N$^+$/P ratio may be in the range of usually greater than 1.0, preferably 1.05 or more, more preferably 1.1 or more, and usually less than 1.5, preferably 1.4 or lower. On the other hand, when a modified nucleic acid (for example a cholesterol-modified nucleic acid) is used as the nucleic acid, a preferred value of the N$^+$/P ratio may be in a relatively high range. Thus the mass ratio of the nucleic acid and the block copolymer may preferably be adjusted considering the above conditions.

The molecular weight of an uncharged hydrophilic segment may preferably be decided considering the molecular weight of a cationic segment and nucleic acid that satisfy the above range of the N$^+$/P ratio. Specifically, it is preferred that the molecular weight ratio X of the uncharged hydrophilic segment defined by the following equation (v) may be set in the range of usually 0.01 or more, preferably 0.05 or more, and usually layer 0.35 or less, preferably 0.1 or less.

[Mathematical 5]

$$X = \frac{M_N}{M_N + M_C + M_A * \frac{P_C}{(N^+/P) * P_A}} \quad \text{Equation (v)}$$

In the equation (ii), $M_N$ represents the molecular weight of the uncharged hydrophilic segment, $M_C$ represents the molecular weight of the cationic segment, $M_A$ represents the molecular weight of the nucleic acid, $P_C$ represents the number of the cationized amino groups in the cationic segment, and $P_A$ represents the number of the phosphate groups in the nucleic acid.

(VII-4: Cross-linker)

A cross-linker is not indispensable for an intra-membrane nucleic acid-containing vesicle, but when the intra-membrane nucleic acid-containing vesicle is used in a physiological environment or in the presence of a salt such as physiological saline (for example, when used as a DDS), a cross-linker may preferably be used as a membrane component, from the viewpoint of preventing an increase in particle size with time.

While the type of the cross-linker is not limited, and may be selected as appropriate according to the use of the intra-membrane nucleic acid-containing vesicle and the type of the block copolymer and nucleic acid, the cross-linker may preferably react with the cationic group (for example an amino group) contained in the cationic segment of the block copolymer and may not react with the nucleic acid, from the viewpoint of efficiently conducting crosslinking and of enhancing the stability of the intra-membrane nucleic acid-containing vesicle obtained. As a specific example of the cross-linker, there can be mentioned a cross-linker having an amino group (for example, glutaraldehyde, dimethyl suberimidate dihydrochloride (DMS), dimethyl 3,3'-dithiobispropionimidate (DTBP), 1-ethyl-3-(3-dimethylaminopropyl) carbodiimide (EDC)), and a cross-linker that crosslinks phosphate groups (for example, a metal ion such as a calcium ion), with glutaraldehyde, DMS, DTBP etc. being preferred and glutaraldehyde being most preferred. While a single cross-linker may be used alone, two or more cross-linkers may be used in any combination or ratio.

The amount used of a cross-linker is not limited, and may be selected, as appropriate, by considering the type of the cross-linker, the number of crosslinking points, the amount of the component to be crosslinked, and the like. For example, in the case of a cross-linker that crosslinks amino groups, the amount used may preferably be selected so that the CL/N ratio defined by the following equation (vi) can satisfy the condition described below:

[Mathematical 6]

$$CL/N \text{ ratio (mole ratio)} = \frac{[\text{moles of the cross-linker}] \times \begin{bmatrix} \text{number of crosslinking} \\ \text{points per molecule of the} \\ \text{cross-linker} \end{bmatrix}}{\begin{bmatrix} \text{moles of amino groups of} \\ \text{the block copolymer} \end{bmatrix}} \quad \text{Equation (vi)}$$

From the viewpoint of efficiently conducting crosslinking and enhancing the stability of the intra-membrane nucleic acid-containing vesicle obtained, the mass ratio of the cross-linker and the block copolymer may preferably be adjusted so as to give a CL/N ratio of usually 0.1 or more, preferably 0.1 or more. On the other hand, when the intra-membrane nucleic acid-containing vesicle is used in nucleic acid delivery (for example, when used as a DDS for RNAi), the amount used of the cross-linker may preferably be not too much, from the viewpoint of allowing the nucleic acid to be efficiently released at the target site, and specifically the mass ratio of the cross-linker and the block copolymer may preferably be adjusted so as to give a CL/N ratio of usually 10 or less, preferably 7 or lower, and more preferably 5 or less.

(VII-5: Another Membrane Component)

While in producing an intra-membrane nucleic acid-containing vesicle, the addition of another membrane component different from the block copolymer or the nucleic acid to the membrane is not indispensable, the other membrane component can be added unless it prevents the formation of the intra-membrane nucleic acid-containing vesicle or reduces stability. The other membrane component may not be specifically limited, and specific examples thereof may include a charged polymer, a charged nanoparticle and the like.

As the charged polymer, a charged polyamino acid or a derivative thereof may be preferred, and a cationic polyamino acid or a derivative thereof may be most preferred. As the cationic polyamino acid or a derivative thereof, there can be mentioned polyaspartamide, polyglutamide, polylysine, polyarginine, polyhistidine, and a derivative thereof, with a polyaspartamide derivative and a polyglutamide derivative being preferred. While the number of the cationic polyamino acid or a derivative thereof is not limited, it may preferably be in the range of 5 or more, more preferably 30 or more, and preferably 200 or less, more preferably 100 or less.

As the charged nanoparticle, a metal-based nanoparticle etc. having an electric charge on the surface can be mentioned.

One type of the above other membrane component may be used alone, or two or more thereof may be used in any combination or ratio.

While the amount used of another membrane component is not limited, it may preferably be kept to a degree that does not prevent vesicle formation by the self-assembly of the block copolymer and the nucleic acid. Specifically, relative to the total weight of the vesicle, it may be usually 30% or less, preferably 20% or less, and more preferably 10% or less.

(VII-6: Method for Producing an Intra-membrane Nucleic Acid-containing Vesicle)

Since an intra-membrane nucleic acid-containing vesicle is formed using an electrostatic interaction between a block copolymer and a nucleic acid, it can be easily produced by mixing a block copolymer and a nucleic acid in an aqueous medium. According to such a production method, the intra-membrane nucleic acid-containing vesicle can be produced without using an organic solvent, and thus is advantageous in the fields of DDS, biomaterials and the like.

Specifically, a first aqueous solution containing a block copolymer and a second aqueous solution containing a nucleic acid are provided. The first and second aqueous solutions may be purified by filtration etc. as desired.

The concentration of the block copolymer in the first aqueous solution and the concentration of the nucleic acid in the second aqueous solution may not be limited, and may be determined, as appropriate, by considering the ratio of the total charged numbers of the block copolymer and the nucleic acid, the solubility of the block copolymer and the nucleic acid into the aqueous solutions, conditions such as the efficiency of forming a intra-membrane nucleic acid-containing vesicle etc.

The type of the solvent for the first and the second aqueous solutions may not be specifically limited as long as it is an aqueous solvent. It may preferably be water, but, a solvent having another component mixed in water, such as physiological saline, an aqueous buffer, and a mixed solvent of water and a water soluble organic solvent etc. can also be used, as long as it does not prevent the formation of the intra-membrane nucleic acid-containing vesicle. As an aqueous buffer, a 10 mM HEPES buffer etc. may be mentioned.

While the pH of the first and the second aqueous solutions may be adjusted as appropriate as long as it does not prevent the formation of a intra-membrane nucleic acid-containing vesicle, it may preferably be pH 5 or higher, more preferably pH 6.5 or higher, and preferably pH 9 or lower, more preferably pH 7.5 or lower. pH can be easily adjusted by using a buffer solution as a solvent. The pH adjustment of the first and second aqueous solutions to be used is advantageous in maintaining the charged state of the block copolymer and the nucleic acid and efficiently forming a vesicle.

While the temperature of the first and second aqueous solutions can be determined as appropriate depending on the solubility of the block copolymer and the nucleic acid in the solvent, it may preferably be 10° C. or higher, more preferably 20° C. or higher, and preferably 80° C. or lower, more preferably 60° C. or lower.

While the ionic strength of the first and second aqueous solutions can be adjusted as appropriate as long as it does not prevent the formation of a intra-membrane nucleic acid-containing vesicle, it may preferably be 5 mM or more, more preferably 10 mM or more, and preferably 300 mM or less, more preferably 150 mM or less.

The above first and second aqueous solutions may be mixed to form an intra-membrane nucleic acid-containing vesicle. The mixing method is not limited, and the second aqueous solution may be added to the first aqueous solution or the first aqueous solution may be added to the second aqueous solution. Also, the first and second aqueous solutions may be simultaneously placed in a vessel for mixing. The mixture obtained of the first and second aqueous solutions may be agitated as appropriate.

While the temperature of the first and second aqueous solutions is not limited as long as it does not prevent the formation of the intra-membrane nucleic acid-containing vesicle, it can be preferably determined by considering the solubility of the block copolymer and the nucleic acid corresponding to their temperature. Specifically, it may preferably be 10° C. or higher, more preferably 20° C. or higher, and preferably 60° C. or lower, more preferably 50° C. or lower.

While, after mixing, the intra-membrane nucleic acid-containing vesicle formed may be immediately subjected to the desired use, time for leaving the mixture to stand may be allowed for in order to equalize the system. While the time for leaving the mixture to stand may vary with the condition such as the efficiency of forming the intra-membrane nucleic acid-containing vesicle, it may preferably be 50 hours or less, more preferably 30 hours or less. However, since the diameter of the intra-membrane nucleic acid-containing vesicle formed may tend to increase with time, it may usually be preferred not to allow the leaving time.

When a cross-linker is used, the cross-linker may be added to and mixed with the mixture of the above first and second aqueous solutions. The cross-linker may be mixed as it is, or an aqueous solution containing the cross-linker may be prepared and this may be used in mixing. The conditions for preparing an aqueous solution of the cross-linker such as an aqueous solvent, pH, temperature, and ionic strength are the same as described for the first and second aqueous solutions.

When another membrane component other than the cross-linker is used, the membrane component may be added to and mixed with the above first and second aqueous solutions. At this time, while the membrane component may be added to the first and second aqueous solutions before mixing, there may preferably be no aggregation or interaction that prevents the formation of the intra-membrane nucleic acid-containing vesicle between the membrane component and the first and second aqueous solutions. Also, the membrane component may be added simultaneously with the mixing of the first and second aqueous solutions, or the mixing of the first and second aqueous solutions may be followed by the addition and further mixing of the membrane component. The other membrane component may be mixed as it is, or an aqueous solution containing the membrane component may be prepared and may be used in mixing. The conditions for preparing an aqueous solution of the membrane component such as an aqueous solvent, pH, temperature, and ionic strength are the same as described for the first and second aqueous solutions.

Furthermore, a procedure such as dialysis, dilution, concentration, and agitation may be added as appropriate.

(VII-7: Use of an Intra-membrane Nucleic Acid-containing Vesicle)

Since the nucleic acid has been stably retained in the membrane in the intra-membrane nucleic acid-containing vesicle, the nucleic acid can be effectively used as it is as a DDS for nucleic acid delivery or as a functional material having the nucleic acid as an active ingredient. For example, by using siRNA as the nucleic acid, the intra-membrane nucleic acid-containing vesicle obtained can be used as a DDS for RNAi.

Also, a substance other than the nucleic acid, such as a drug, can be encapsulated in the cavity (internal water phase) of the intra-membrane nucleic acid-containing vesicle. By so doing, the vesicle can be effectively used as a DDS for delivering the combination of the nucleic acid and the drug. While the other drug is not limited, and may be selected as appropriate according to the use and property of the vesicle, there can be mentioned a protein, a peptide, an amino acid or a derivative thereof, a fat, a monosaccharide, an oligosaccharide, a polysaccharide, a glycoprotein, another drug etc. In classification by use, there can be mentioned an cancer agent (for example, a hydrophobic anti-cancer agent such as doxorubicin and paclitaxel, a metal complex anti-cancer agent such as cisplatin), gadolinium and an iron compound used in diagnostic MRI etc., an organic light-emitting (fluorescent, phosphorescen) dye, a quantum dot and the like.

When another drug is encapsulated in the cavity (internal water phase) of the intra-membrane nucleic acid-containing vesicle, the following methods may be mentioned:

(i) A method of adding the drug to the first and second aqueous solutions and mixing before the formation of the intra-membrane nucleic acid-containing vesicle;

(ii) A method of adding the drug to the first and second aqueous solutions and mixing during the formation the intra-membrane nucleic acid-containing vesicle; and (iii) A method of, after mixing the first and second aqueous solutions, adding the drug to the aqueous solution containing the intra-membrane nucleic acid-containing vesicle formed and mixing.

The methods of (i) and (ii) are useful when the drug is an uncharged (neutral) substance. However, the methods of (i) and (ii) are used for a charged (cationic or anionic) drug, the charged drug may inhibit the formation of the intra-membrane nucleic acid-containing vesicle, with a result that no drug-encapsulating vesicle can be obtained.

On the other hand, the method of (iii) corresponds to the case of using the intra-membrane nucleic acid-containing vesicle as a vacant vesicle in the above method for producing a substance-encapsulating vesicle of the present invention. In accordance with the present method, as described above, the drug can be used irrespective of whether it is an uncharged (neutral) substance or a charged (cationoic or anionic) substance. Though the reason for it is not clear, it is believed that the obtained intra-membrane nucleic acid-containing vesicle that once dissociated has reassembled.

In the case of method (iii), the conditions are as described in the above [II: Method for producing a substance-encapsulating vesicle], [IV: Encapsulation-target substance] and [V: Other steps].

While in any of the above methods of (i)-(iii), the drug to be encapsulated may be used as it is, an aqueous solution containing the drug may be prepared and used in mixing. The conditions for preparing the aqueous solution of the drug such as an aqueous solvent, pH, temperature, and ionic strength are the same as described above for the first and second aqueous solutions.

When another membrane component such as a cross-linker is used in combination, the order of mixing the drug and the membrane component is arbitrary. When a cross-linker is used, however, it may be preferred, from the viewpoint of efficiently encapsulating the drug into the cavity of the vesicle, that the encapsulation of the drug in the vesicle may be followed by the addition and mixing of the cross-linker.

Furthermore, a procedure such as dialysis, dilution, concentration, and agitation may be added as appropriate.

(VII-8: Others)

While the intra-membrane nucleic acid-containing vesicle was explained with reference to specific embodiments as above, a person skilled in the art will be able to work the invention, based on the description of the present invention, by modifying the above embodiments as appropriate.

For example, in stead of the intra-membrane nucleic acid-containing vesicle explained in the embodiment, which is composed of a block copolymer having an uncharged hydrophilic segment and a cationic segment and a nucleic acid, a copolymer having an uncharged hydrophilic segment and a nucleic acid bound therein and a polymer comprising a cationic segment may be substituted to form a similar intra-membrane nucleic acid-containing vesicle.

In this case as well, usually the cationic segment and the nucleic acid are electrostatically bound to form an intermediate layer, and an uncharged hydrophilic segment forms an outer layer and an inner layer, with a result that an intra-membrane nucleic acid-containing vesicle of a structure comprising a membrane of a trilaminar structure and a cavity surrounded thereby can be formed.

In such an embodiment, details of each component of the intra-membrane nucleic acid-containing vesicle and details of the method for producing the intra-membrane nucleic acid-containing vesicle are essentially the same as the descriptions above. A person skilled in the art will be able to work such an embodiment based on the description of the present invention by making necessary modifications as appropriate. Therefore, the method of producing an intra-membrane nucleic acid-containing vesicle having such a structure is also encompassed in the scope of the present invention.

EXAMPLES

Then, the present invention will be explained more specifically with reference to examples. The examples that follow are only for illustrative purposes and do not limit the present invention in any way.

In the following description, the term "solution" refers to a solution, unless otherwise specified, having a 10 mM phosphate buffer (pH 7.4) as a solvent.

Also in the following description, as the "vortex mixer", Vortex-Genie 2 manufactured by Scientific Industries Inc. was used unless otherwise specified.

The mean particle size, the polydispersity index (PDI) and the zeta potential in the following description were measured with Zetasizer Nano-ZS manufactured by Malvern unless otherwise specified.

Example Group I

Production and Evaluation of an Intra-membrane Nucleic Acid-containing Vesicle (I-a) Preparation of a Block Copolymer:

A block copolymer (hereinafter referred to as "PEG-PAsp (DAP)") represented by the following formula having polyethylene glycol (molecular weight: about 2000) (hereinafter referred to as "PEG") as an uncharged hydrophilic segment and a poly(diaminopentane structure-containing aspartic acid derivative) (the degree of polymerization: 70) (hereinafter referred to as "PAsp(DAP)") as a cationic segment was synthesized.

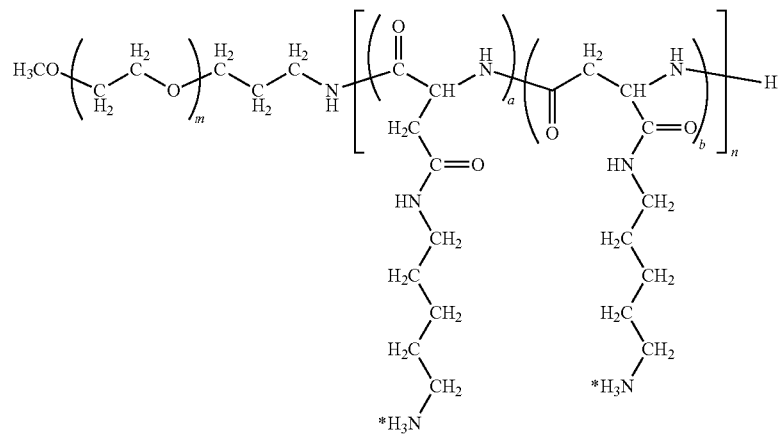

[Chemical 11]

wherein, m represents the degree of polymerization of PEG, and is about 44, n represents the degree of polymerization of PAsp(DAP), and is about 70, and any of a and b is greater than 0 and less than 1, provided that a+b=1.

(I-b) Preparation of an Intra-membrane Nucleic Acid-containing Vesicle:

As siRNA, GL3 (the sense strand: 5'-CUU ACG CUG AGU ACU UCG AdTdT-3' (SEQ ID NO: 1), the antisense strand: 5'-UCG AAG UAC UCA GCG UAA GdTdT-3' (SEQ ID NO: 2): the number of bases: 21) was used. To 50 µl of a 1 mg/ml siRNA solution, a 1 mg/ml PEG-PAsp(DAP) aqueous solution obtained in the above (I-a) was added at a volume that enables to obtain a value of the $N^+/P$ ratio defined in following Table 1, and agitated and mixed with a vortex mixer for 2 minutes to prepare the mixtures of Examples I-1 to I-4 and Comparative Examples I-1 to I-4.

TABLE 1

|  | $N^+/P$ ratio |
| --- | --- |
| Example I-1 | 1.1 |
| Example I-2 | 1.15 |
| Example I-3 | 1.2 |
| Example I-4 | 1.4 |
| Comparative Example I-1 | 0 |
| Comparative Example I-2 | 1.0 |
| Comparative Example I-3 | 1.5 |
| Comparative Example I-4 | 2.0 |

(I-c) Evaluation of an Intra-membrane Nucleic Acid-containing Vesicle:

(I-c1) Measurement by Dynamic Light Scattering:

In order to investigate the physical properties of particles present in the mixtures of Examples I-1 to I-4 and Comparative Examples I-1 to I-4, measurement by the dynamic light scattering method was conducted to determine the mean particle size and the polydispersity index (PDI).

Figure 6:
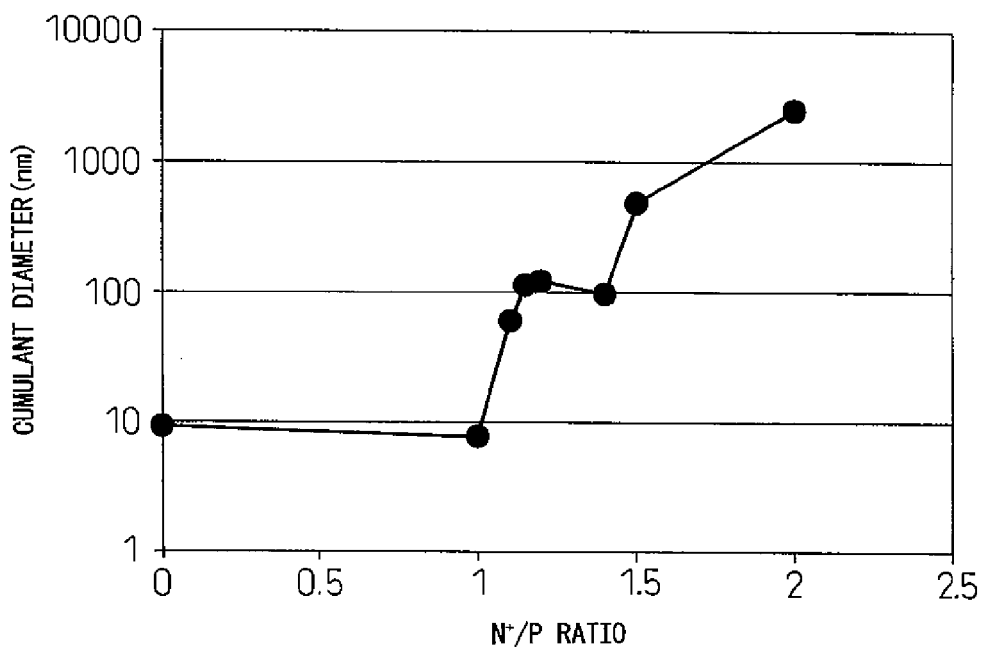
FIGS. 6(a) and (b) are graphs showing a relationship between the $N^+/P$ ratio and the mean particle diameter and the polydisperse index.
Figure 6:
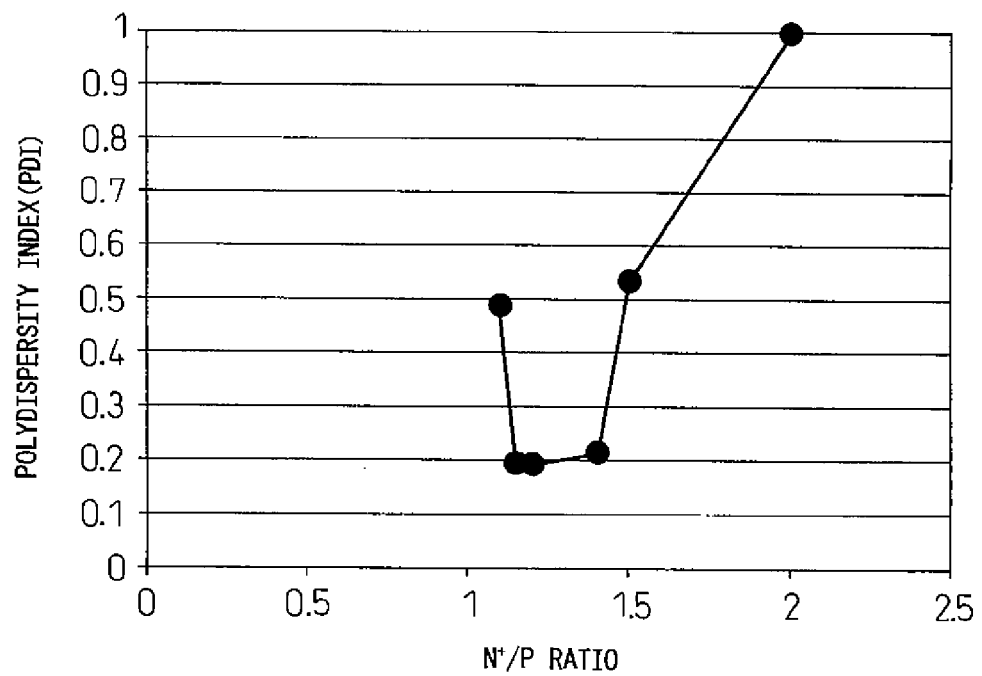

The measurement results of the mean particle size and the polydispersity index are shown in FIG. 6(a) and (b), respectively. It can be seen from FIG. 6(a) that in the range of $N^+/P$ ratio of greater than 1.0 and less than 1.5 (Examples I-1 to I-4), the mean particle size remains constant at about 100 nm, whereas at a $N^+/P$ ratio of 1.0 or less (Comparative Examples I-1, I-2), the mean particle size becomes remarkably small, and at a $N^+/P$ ratio of 1.5 or more (Comparative Examples I-3, I-4), conversely, the mean particle size becomes remarkably large. Also, it can be seen from FIG. 6(b) that in the range of $N^+/P$ ratio of greater than 1.0 and less than 1.5 (Examples I-1 to I-4), the polydispersity index becomes small and uniform spherical particles are present. By taking these results together, it can be seen that in the range of $N^+/P$ ratio of greater than 1.0 and less than 1.5 (Examples I-1 to I-4), PEG-PAsp(DAP) and siRNA self-assemble and therefore uniform spherical particles with a mean particle size of about 100 nm are formed in the mixture.

(I-c2) Examination with a Transmission Electron Microscope:

The particles in the mixtures of Examples I-1 to I-4 and Comparative Examples I-1 to I-4 that were obtained in the above (I-b) were examined by a transmission electron microscope according to the following procedure.

Onto a Cu grid (Nisshin EM Corporation) that was carbon-coated after attaching a collodion supporting membrane thereto, the mixture of the above (I-b) was added dropwise, and furthermore a trace amount of uranium acetate was added dropwise. Then excess water was blotted off with a filter paper, and dried to prepare a specimen grid in which the particles in the mixture of the above (I-b) were fixed. The specimen grid obtained was examined with a transmission electron microscope.

Figure 7:
FIG. 7(a) is a transmission electron micrograph of a sample ($N^+/P$ ratio=1.2) in which an intra-membrane nucleic acid-containing vesicle was formed.
FIG. 7(b) is a transmission electron micrograph of a sample ($N^+/P$ ratio=2.0) in which no intra-membrane nucleic acid-containing vesicle was formed.
Figure 7:
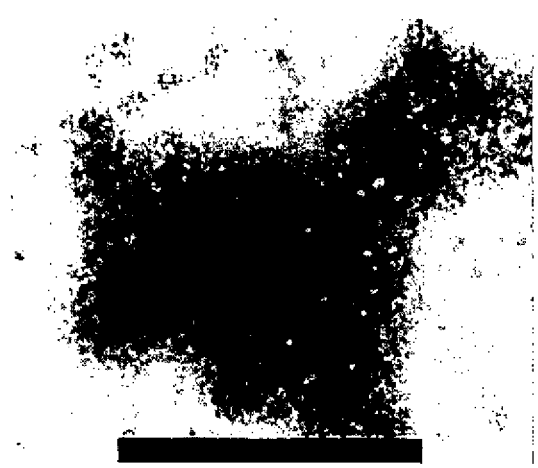
Figure 8:
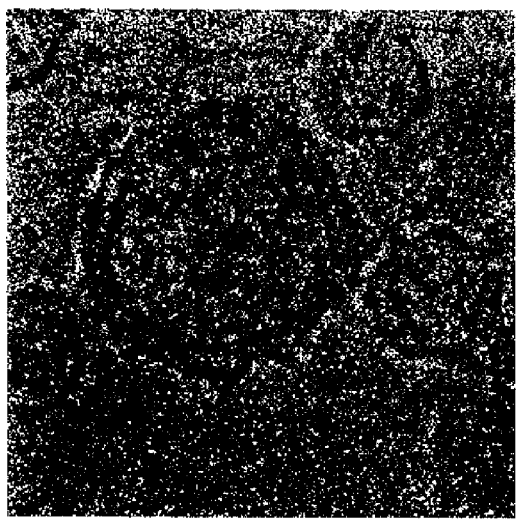
FIGS. 8(a) to (d) are the phase-contrast cryo-transmission electron micrographs of a crosslinked intra-membrane nucleic acid-containing vesicle.

Examples of electron photomicrographs obtained for Example I-3 ($N^+/P$ ratio=1.2) and Comparative Example I-4 ($N^+/P$ ratio=2.0) are shown in FIGS. 7(a) and (b), respectively. Since a multitude of concentric particles with a mean particle size of about 100 nm were observed in the electron photomicrographs of Example I-2 (see FIG. 7(a)), it can be seen that uniform spherical vesicles with a mean particle size of about 100 nm having cavities were formed. On the other hand, in the electron photomicrograph (see FIG. 7(b)) of Comparative Example I-4, no such concentric uniform particles were observed, and instead large particles of irregular shape were only present.

For electron photomicrographs of the other $N^+/P$ ratios, in the range of a $N^+/P$ ratio of greater than 1.0 and less than 1.5, a multitude of concentiric particles with a mean particle size of about 100 nm were observed as in FIG. 7(a), whereas at a $N^+/P$ ratio of 1.0 or less or 1.5 or more, such particles were not observed.

When these results are taken together with the measurement results of the above dynamic light scattering method, it can be seen that in the range of a $N^+/P$ ratio of greater than 1.0 and less than 1.5 (Examples I-1 to I-4), novel vesicles (intra-membrane nucleic acid-containing vesicles) having a membrane formed by PEG-PAsp(DAP) and siRNA was formed.

Example Group II

Production and Evaluation of a Crosslinked Intra-membrane Nucleic Acid-containing Vesicle (II-a) Preparation of a Crosslinked Intra-membrane Nucleic Acid-containing Vesicle Vesicles were formed in a procedure similar to that described in "(I-b) Preparation of an intra-membrane nucleic acid-containing vesicle" of Example group I except that the $N^+/P$ ratio was fixed at 1.4. Two hours after preparation, to 30 µl of the vesicle solution obtained, 10 µl of a glutaraldehyde solution with a concentration defined in the following Table 2 was added as a cross-linker, and then agitated and mixed with a vortex mixer for 2 minutes to prepare the vesicle-containing mixtures of Reference Example II and Examples II-1 to II-6. Each glutaraldehyde solution was prepared by diluting a 70% by weight glutaraldehyde (manufactured by Wako Pure Chemical Industries, Ltd.) with a buffer solution (HEPES buffer). The CL/N ratios of the vesicle-containing mixtures obtained finally are shown together in the following Table 2.

TABLE 2

|  | Glutaraldehyde solution (% by weight) | CL/N ratio |
| --- | --- | --- |
| Reference Example II | 0 | 0 |
| Example II-1 | 0.00875 | 1.0 |
| Example II-2 | 0.0175 | 2.0 |
| Example II-3 | 0.0875 | 10 |
| Example II-4 | 0.175 | 20 |
| Example II-5 | 0.875 | 100 |
| Example II-6 | 1.75 | 200 |

(II-b) Evaluation of a Crosslinked Intra-membrane Nucleic Acid-containing Vesicle:

The vesicle-containing mixture of Example II-1 obtained in the above (II-a) was examined by a phase-contrast cryo-transmission electron microscope. Specifically, a sample solution was developed onto a microgrid, excess water was blotted off with a filter paper, and then was quick-frozen in a liquified ethane using EM CPC cryo-station (Leica Microsystems, Vienna, Austria) to prepare a specimen for examination. Images were photographed using a transmission electron microscope JEM2011 (manufactured by JEOL Ltd.) equipped with a Zernike phase plate. The phase-contrast cryo-transmission electron micrographs are shown in FIGS. 8(a)-(d). All the vacant vesicles (crosslinked intra-membrane nucleic acid-containing vesicles) obtained had a similar structure and were spherical vesicles each comprising one dividing wall with a thickness of about 10 nm, and particle size was about 100 nm.

Also, to mixtures containing the intra-membrane nucleic acid-containing vesicles of Reference Example II and Examples II-1 to II-6 obtained in the above (II-a), sodium chloride or a sodium chloride-containing buffer solution was added to a concentration equal to physiological saline (a 150 mM sodium chloride solution) and mixed, and then after a predetermined time elapsed, they were measured by the dynamic light scattering method to investigate changes with time in the mean particle size and the polydispersity index (PDI).

Figure 9:
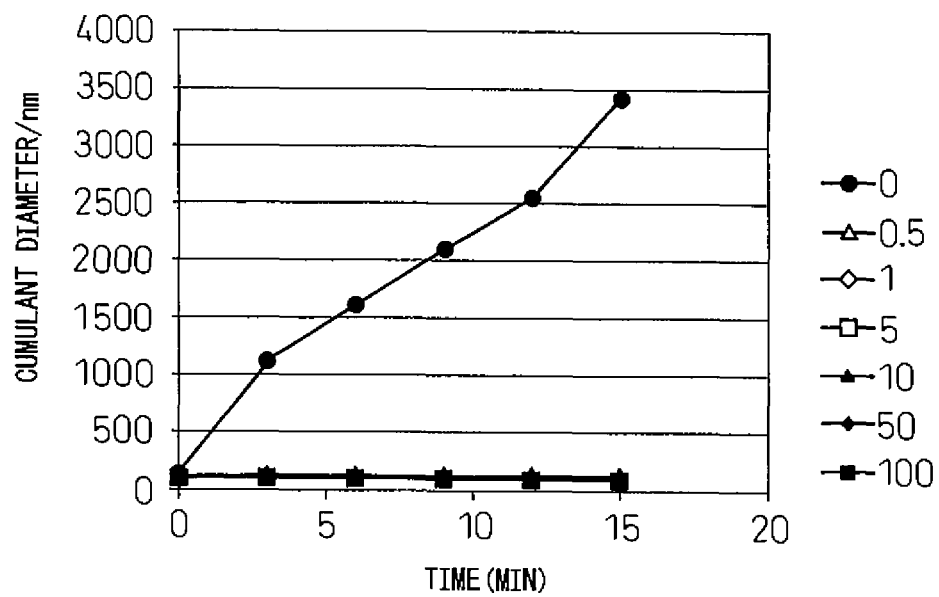
FIGS. 9(a) and (b) are graphs showing changes with time in the particle size and shape of an intra-membrane nucleic acid-containing vesicle.
Figure 9:
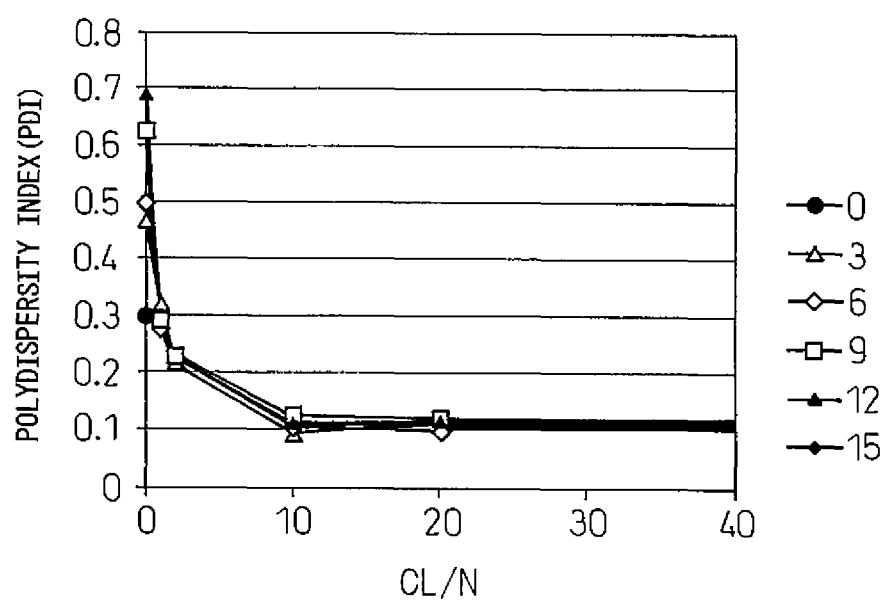

Relationship between the mean particle size and the CL/N ratio and the elapsed time is shown in the graph of FIG. 9(a), and the relationship between the polydispersity index (PDI) and the CL/N ratio and the elapsed time is shown in the graph of FIG. 9(b), respectively. From FIGS. 9(a) and (b), it can be seen that in the vacant vesicles (the intra-membrane nucleic acid-containing vesicles that are not crosslinked) of Reference Example II (the CL/N ratio=0, i.e. no crosslinker) the particle size increased with time under a physiological condition, whereas all the vacant vesicles (the crosslinked intra-membrane nucleic acid-containing vesicles) of Examples II-1 to II-6 (the CL/N ratio≥1, i.e. with a cross-linker) the particles remained uniform and spherical particles with almost no changes with time in particle size even under a physiological condition.

Example Group III

Evaluation of Efficiency of siRNA Introduction into the Intra-membrane Nucleic Acid-containing Vesicle (III-a) Evaluation of RNAi Activity:
(III-a1) Preparation of an Intra-membrane Nucleic Acid-containing Vesicle The vesicle-containing mixtures of Examples III-1 to III-3 and References Example III-1 and III-2 were prepared in a procedure similar to that described in "(II-a) Preparation of the intra-membrane nucleic acid-containing vesicle" of Example group II, except that glutaraldehyde solutions with concentrations defined in the following Table 3 were used as the cross-linker and the CL/N ratios of the vesicle-containing mixtures obtained finally were adjusted to give values defined in the following Table 3.

TABLE 3

| | Glutaraldehyde solution (% by weight) | CL/N ratio |
|---|---|---|
| Example III-1 | 0 | 0 |
| Example III-2 | 0.00875 | 1.0 |
| Example III-3 | 0.0175 | 2.0 |
| Reference Example III-1 | 0.0875 | 10 |
| Reference Example III-2 | 0.175 | 20 |

Also, the control mixtures corresponding to Examples III-1 to III-3 and Reference Examples III-1 and III-2 were prepared in a procedure similar to the above procedure, except that a scramble (the sense strand: 5'T-UUC UCC GAA CGU GUC ACG UdTdT-3' (SEQ ID NO: 3), the antisense strand: 5'-ACG UGA CAC GUU CGG AGA AdTdT-3' (SEQ ID NO: 4): the number of bases: 21) was used as the control siRNA.

(III-a2) Measurement of RNAi Activity:
Using mixtures containing the intra-membrane nucleic acid-containing vesicles of Examples III-1 to III-3 and Reference Examples III-1 and III-2 obtained in the above (III-a1), the mouse melanoma cell B16F10-Luc was treated in the following procedure to investigate the efficiency of siRNA introduction.

Thus, to the mouse melanoma cell B16F10-Luc in a DMEM medium containing 400 µl of 10% bovine fetal serum, each of the mixtures (containing GL3 as siRNA) of Examples III-1 to III-3 and Reference Examples III-1 and III-2 was added to a siRNA-converted concentration of 500 nM, cultured for 48 hours in an incubator, the culture medium was removed, and the cell lysate was added. To 20 µl of the supernatant, 100 µl of a luciferase assay solution (manufactured by Promega) was added, and the amount of light emitted was measured by a luminometer to determine the amount expressed of the luciferase gene.

Also, using the control mixtures (containing the scramble as siRNA) corresponding to Examples III-1 to III-3 and Reference Examples III-1 and III-2, a similar procedure was conducted to determine the amount expressed of the luciferase gene.

Furthermore, the cell group to which no siRNA was added was subjected to a similar procedure to determine the amount expressed of the luciferase gene.

For each of Examples III-1 to III-3 and Reference Examples III-1 and III-2, using the amount expressed a and the reference amount expressed b determined in the above procedure, the relative amount expressed c was determined from the following equation (vii):

[Mathematical 7]

$$\text{Relative amount expressed } (c) \ (\%) = \frac{\text{Amount expressed } (a)}{\text{Reference amount expressed } (b)} \times 100 \quad \text{Equation (vii)}$$

Figure 10:
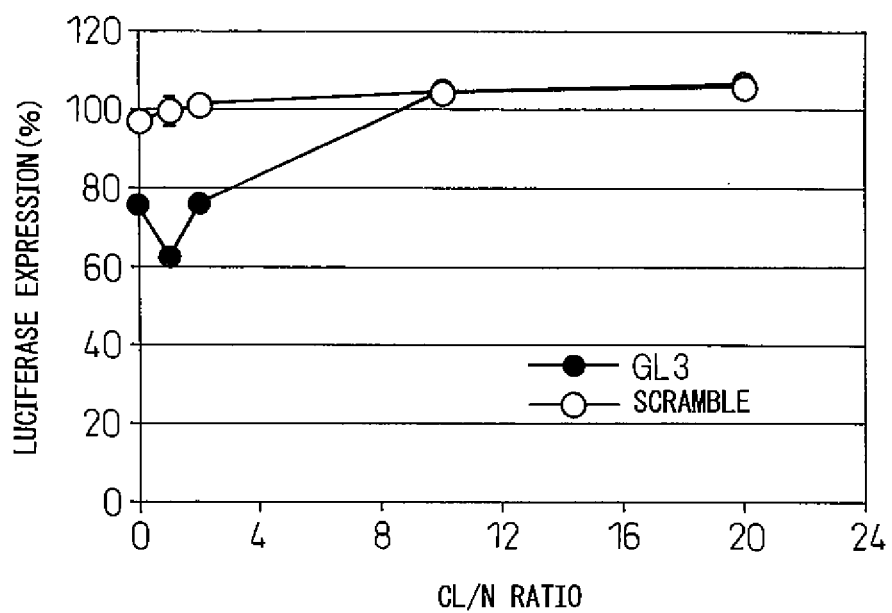
FIG. 10 is a graph showing the RNAi activity of an intra-membrane nucleic acid-containing vesicle.

The measurement results of the relative amount expressed of the luciferase gene in each of Examples III-1 to III-3 and Reference Examples III-1 and III-2 are shown in FIG. 10. As shown in FIG. 10, the expression of the luciferase gene was significantly suppressed by the intra-membrane nucleic acid-containing vesicles of Examples III-1 to III-3 (the CL/N ratio is 0-2), RNAi activity was noted. Therefore, from the intra-membrane nucleic acid-containing vesicles of Examples III-1 to III-3 (the CL/N ratio is 0-2), it can be seen that siRNA was efficiently introduced into the cell.

(III-b) Evaluation of Cell Uptake by Confocal Microscope (III-b1) Preparation of an Intra-membrane Nucleic Acid-containing Vesicle The vesicle-containing mixtures of Examples III'-1 to III'-3 and Reference Examples III'-1 to III'-4 were prepared in a manner similar to that of the above (III-a1), except that Cy5-labelled Gl3 in which Cy5 was attached to the 5'-end of the antisense strand and the sense strand of the above GL3 was used as siRNA, and a glutaraldehyde solution of the concentration defined in the following Table 4 was used as a cross-linker, and the CL/N ratio of the vesicle-containing mixture obtained finally was adjusted to give values defined in the following Table 4.

TABLE 4

|  | Glutaraldehyde solution (% by weight) | CL/N ratio |
|---|---|---|
| Example III'-1 | 0 | 0 |
| Example III'-2 | 0.00875 | 1.0 |
| Example III'-3 | 0.0175 | 2.0 |
| Reference Example III'-1 | 0.0875 | 10 |
| Reference Example III'-2 | 0.175 | 20 |
| Reference Example III'-3 | 0.875 | 100 |
| Reference Example III'-4 | 1.75 | 200 |

(III-b2) Examination with a Confocal Microscope

Cell uptake by siRNA after cell treatment with the intra-membrane nucleic acid-containing vesicle obtained was examined with a confocal microscope.

Thus, to mouse melanoma cell B16F19-Luc in a DMEM medium containing 1 ml of 10% fetal bovine serum, each of the mixtures (siRNA-converted concentration of 500 nM) of Examples III'-1 to III'-3 and Reference Examples III'-1 to III'-4 was added, and 24 hours later, examined with a confocal microscope (LSM 510 META NLO manufactured by Carl Zeiss).

Figure 11:
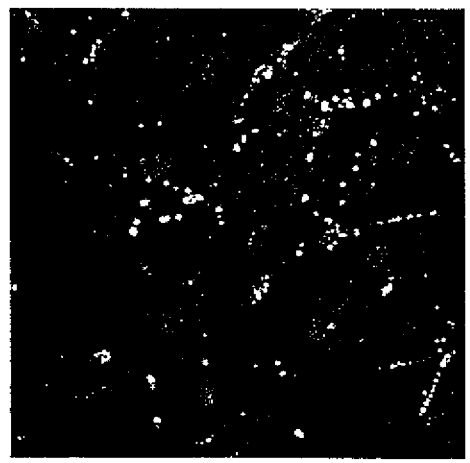
FIGS. 11(a) and (b) are drawings showing the intracellular uptake of siRNA by an intra-membrane nucleic acid-containing vesicle.
Figure 11:
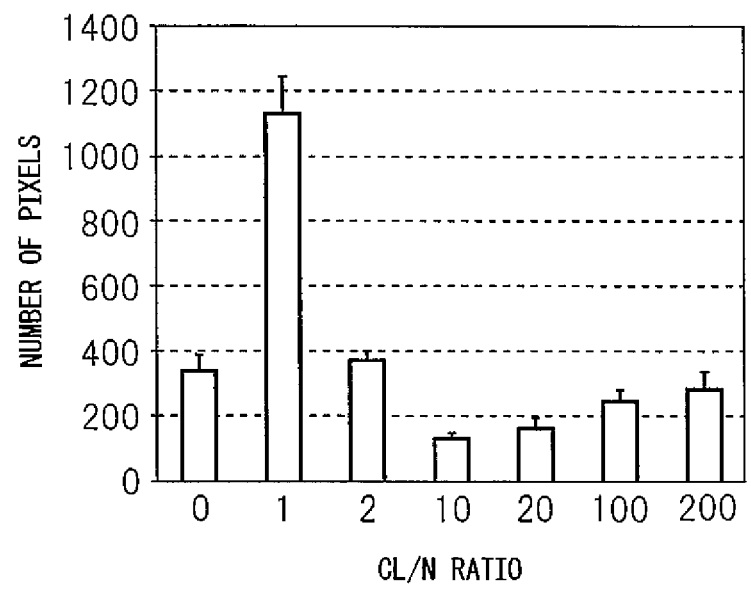

The confocal micrograph of Example III'-2 (the CL/N ratio=1.0) is shown in FIG. 11(a). In FIG. 11(a), the white regions indicate siRNA. From FIG. 11(a), it can be seen that siRNA has been markedly taken up into the cell.

Similarly, in Example III'-1 (the CL/N ratio=0) and Example III'-3 (the CL/N ratio=2.0) as well, the remarkable uptake of siRNA into the cell was observed.

The confocal micrographs obtained for Examples III'-1 to III'-3 and Reference Examples III'-1 to III'-4 were subjected to image analysis. Specifically, by counting the number of white pixels derived from Cy5-labelled siRNA, the amount of siRNA taken up into the cell was estimated.

The result obtained is shown in the graph of FIG. 11(b), It can be seen from FIG. 11(b) that the amount of siRNA taken up into the cell was significantly large in the intra-membrane nucleic acid-containing vesicle having a CL/N ratio of 0-2 and specifically in the intra-membrane nucleic acid-containing vesicle having a CL/N ratio of 1.0.

The above results indicate that by the intra-membrane nucleic acid-containing vesicles of Examples III'-1 to III'-3 (the CL/N ratio is 0-2), siRNA was efficiently taken up into the cell.

Example Group IV

Production and Evaluation of the Uncharged Substance-encapsulating Intra-membrane Nucleic Acid-containing Vesicle (IV-a) Production of an Uncharged Substance-encapsulating Intra-membrane Nucleic Acid-containing Vesicle In the procedure described in "(III-b1) Preparation of a vesicle" of the Example group III, in addition to 47.8 µl of a 1 mg/ml aqueous solution of PEG-PAsp(DAP) and 50 µl of a 1 mg/ml aqueous solution of siRNA (or Cy3-labelled siRNA) ($N^+/P$ ratio: 1.4), 10 µl of a 10 mg/ml aqueous solution of fluorescent dextran (manufactured by Aldrich, molecular weight 10000), which is an uncharged substance, was used as an encapsulation-target substance, and agitated and mixed with a vortex mixer in the order of "agitation/mixing A"→"agitation/mixing B" in the following table to prepare the vesicles. Two hours after the preparation, a 0.1875% by weight aqueous solution of glutaraldehyde was added as a cross-linker and further mixed (the CL/N ratio: 100) and purified by an ultrafiltration membrane with a molecular weight cutoff of about 300,000 to prepare the vesicle-containing mixtures of Examples IV-1 to IV-3. Also, a similar procedure was conducted without using fluorescent dextran to prepare a vesicle-containing mixture of Reference Example VI. Each of agitation/mixing A and B was conducted with a vortex mixer at about 3300 rpm for 2 minutes. Between agitation/mixing A and agitation/mixing B, and after agitation/mixing B, the leaving time of 3 minutes or more was allowed, respectively.

TABLE 5

| | Mixing procedure | | |
|---|---|---|---|
| | Agitation/mixing A | → | Agitation/mixing B |
| Example IV-1 | PEG-PAsp(DAP) and fluorescent dextran were agitated/mixed | → | siRNA was added and further mixed |
| Example IV-2 | siRNA and fluorescent dextran were agitated/mixed | → | PEG-PAsp(DAP) was added and further mixed |
| Example IV-3 | PEG-PAsp(DAP) and siRNA were agitated/mixed (vacant vesicle formation) | → | Fluorescent dextran was added and further mixed |
| Reference Example IV | PEG-PAsp(DAP) and fluorescent siRNA were mixed (vacant vesicle formation, without using fluorescent dextran) | | |

(IV-b) Evaluation of an Uncharged Substance-encapsulating Intra-membrane Nucleic Acid-containing Vesicle The vesicle-containing mixtures of Example IV-1 to IV-3 obtained in the above (IV-a) were subjected to measurement by fluorescence correlation spectroscopy (FCS) to calculate the speed of motion of fluorescent particles in a micro volume, i.e. the translational diffusion coefficient. From changes in the translational diffusion coefficient obtained of the fluorescent dextran, it becomes possible to determine whether the fluorescent dextran has been encapsulated into the vesicle or not.

Specifically, using an ultrafiltration membrane with a molecular weight cutoff of 300,000, each vesicle solution was ultrafiltrated for 5 times at a condition of 2000 G, 8 minutes to remove the released fluorescent dextran. After the ultrafiltration procedure, each vesicle solution was adjusted to a concentration of 100 µg/ml siRNA, and subjected to FCS measurement using a confocal fluorescent microscope (LSM510) manufactured by Carl Zeiss. The fluorescent dextran was excited by an argon laser (488 nm), the object lens used was a water immersion lens with a 40-fold magnification, and analysis was performed by the Confocor 3 software.

Also, as a control example, a 0.5 μg/ml solution of fluorescent dextran was subjected to similar measurement to calculate a diffusion constant.

Figure 12:
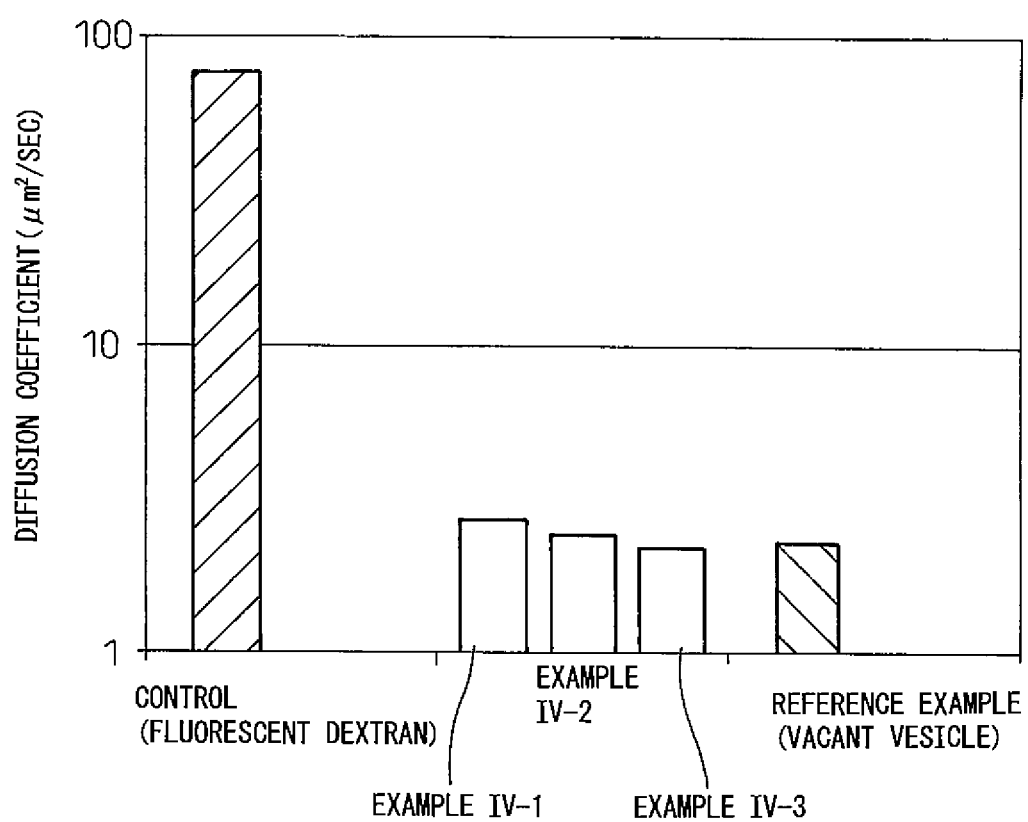
FIG. 12 is a graph showing substance encapsulation into an intra-membrane nucleic acid-containing vesicle.

The result of the diffusion constant obtained is shown in FIG. 12. As shown in FIG. 12, the diffusion constant of the vesicles of Examples IV-1 to IV-3 obtained by mixing PEG-PAsp(DAP), siRNA, and fluorescent dextran was much smaller than the diffusion constant of the control example of the fluorescent dextran, and was about the same level as the diffusion constant of the vesicle of Reference Example IV formed from PEG-PAsp(DAP) and fluorescent siRNA.

The above results revealed that in Examples IV-1 to IV-3, irrespective of the order of mixing PEG-PAsp(DAP), siRNA, and fluorescent dextran, the intra-membrane nucleic acid-containing vesicle (a vacant vesicle) comprising PEG-PAsp(DAP) and siRNA was formed as in Reference Example VI, and the substance-encapsulating intra-membrane nucleic acid-containing vesicle containing fluorescent dextran (an encapsulation-target substance) in the cavity (internal water phase) was obtained.

It can be seen, specifically, that by the procedure of forming an intra-membrane nucleic acid-containing vesicle (a vacant vesicle) comprising PEG-PAsp(DAP) and siRNA beforehand, then adding fluorescent dextran (an encapsulation-target substance) followed by agitating and mixing in Example IV-3, a substance-encapsulating intra-membrane nucleic acid-containing vesicle encapsulating the fluorescent dextran (an encapsulation-target substance) in the cavity (internal water phase) thereof was obtained. This is a surprising finding.

In Example IV-1 (after PEG-PAsp(DAP) and fluorescent dextran were agitated and mixed, siRNA was added and further mixed) and Example IV-2 (after siRNA and fluorescent dextran were agitated and mixed, PEG-PAsp(DAP) was added and further mixed) as well, similar substance-encapsulating intra-membrane nucleic acid-containing vesicles have been obtained. That this was due to the use of fluorescent dextran which is an uncharged substance as an encapsulation-target substance is clear from the comparison with the following Example group V.

Example Group V

Production and Evaluation of a Negatively Charged Substance-encapsulating Vesicle Example V-1

Production of a QD (a Negatively Charged Substance)-encapsulating Vesicle

As the first polymer, an anionic block copolymer PEG-P(Asp) (zeta potential: −30.6 mV) comprising polyethylene glycol (PEG) (molecular weight: about 2000), which is an uncharged hydrophilic segment, and polyaspartic acid (P(Asp)) (the degree of polymerization: 75), which is an anionic segment, was used.

As the second polymer, a cationic homopolymer Homo-P(Asp-AP) (zeta potential: +16.3 mV) comprising poly(diaminopentane structure-containing aspartic acid derivative) (P(Asp-AP)) (the degree of polymerization: 82), which is a cationic segment, was used.

As the encapsulation-target substance, CdTe quantum dot (hereinafter referred to as "QD") (mean particle size: 4.2 nm; zeta potential: −64.1 mV; reference: A. Zintchenko, et al. Molecular Therapy (2009) 17, 11, 1849-1856) was used.

Each of the first polymer and the second polymer was dissolved in a 10 mM phosphate buffer (pH 7.4) (aqueous medium) to a polymer concentration of 2.0 mg/ml. The first polymer solution and the second polymer solution obtained were placed in an Eppendorf tube so that the charge ratio becomes equal (i.e. the C/A ratio=1.0) and mixed, and then agitated with a vortex mixer at about 3300 rpm for 2 minutes to obtain a solution containing the vesicles (vacant vesicles) formed by the self-assembly of the first polymer and the second polymer.

The vacant vesicle-containing solution obtained as above was measured by the dynamic light scattering method to determine pore size distribution, mean particle size, polydispersity index (PDI), and zeta potential. At a mean particle size of 104 nm, the formation of monodispersion particles was noted. The PDI was 0.045 and the zeta potential was −9.8 mV.

To the vacant vesicle-containing solution obtained as above, a solution of the encapsulation-target substance was added to prepare a solution (a subject solution to be mixed) with a total polymer concentration of 1.0 mg/ml and an encapsulation-target substance concentration of $2.3 \times 10^{15}$/ml. This subject solution to be mixed was agitated and mixed with a vortex mixer at about 3300 rpm for 2 minutes, and then allowed to stand for over 3 minutes. The solution obtained after mixing was transparent.

Figure 13:
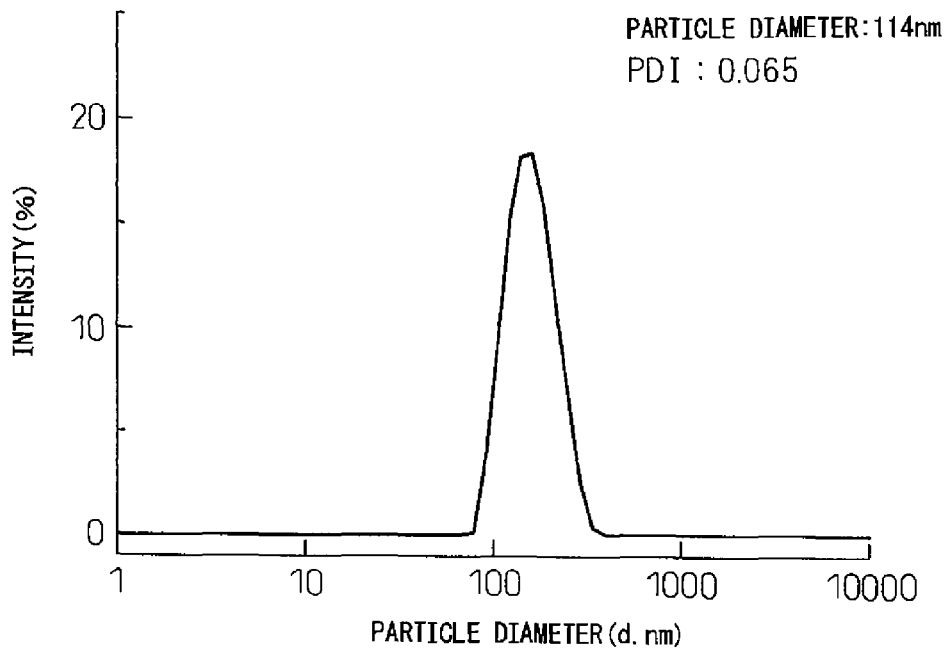
FIG. 13 is a graph showing the particle distribution of the substance-encapsulating vesicle of Example V-1.

The solution after mixing was added to a solution (in a 10 mM phosphate buffer (0 mM NaCl), pH 7.4) containing 10 equivalents of EDC (purchased from PEPTIDE INSTITUTE, INC.) relative to the carboxyl group contained in PEG-P(Asp), and then allowed to stand at room temperature for 12 hours to crosslink the polymer. QD remaining in the free state in the solution without being encapsulated was removed by centrifugal ultrafiltration (VIVASPIN 20 manufactured by Sartorius Sterium Biotech, a molecular weight cutoff of 300,000 was used; 300 rpm, 4° C.) to purify the solution, which was then measured by the dynamic light scattering method to determine particle size distribution, mean particle size, and polydispersity index (PDI). The graph of particle size distribution is shown in FIG. 13. At a mean particle size of 114 nm, the formation of monodispersion particles was noted. The PDI was 0.065.

Subsequently, a fluorescence correlation spectroscopy (FCS) measurement was conducted at room temperature using a confocal fluorescent microscope (LSM510) manufactured by Carl Zeiss. The fluorescent dextran was excited by an argon laser (488 nm), the object lens used was a water immersion lens with a 40-fold magnification, and analysis was performed by the Confocor 3 software to determine an autocorrelation function $G(\tau)$. The QD solution ($2.3 \times 10^{15}$/ml), which is an encapsulation-target substance, was also subjected to MCS measurement to determine an autocorrelation function $G(\tau)$. The temporal attenuation curve of the autocorrelation function $G(\tau)$ obtained is shown in FIG. 14.

The autocorrelation function $G(\tau)$ is a function for evaluating the fluctuation of fluorescent intensity after time $\tau$, and attenuates with time and converges after a sufficient time. The longer the time (slow attenuation) until convergence, the more gradual the fluctuation is, i.e. indicates that the movement of the fluorescent object which is the subject of measurement is slow. Thus, the more the attenuation curve of the autocorrelation function G(τ) is shifted to the right, the greater the size of the fluorescent object which is the subject of measurement has become.

Figure 14:
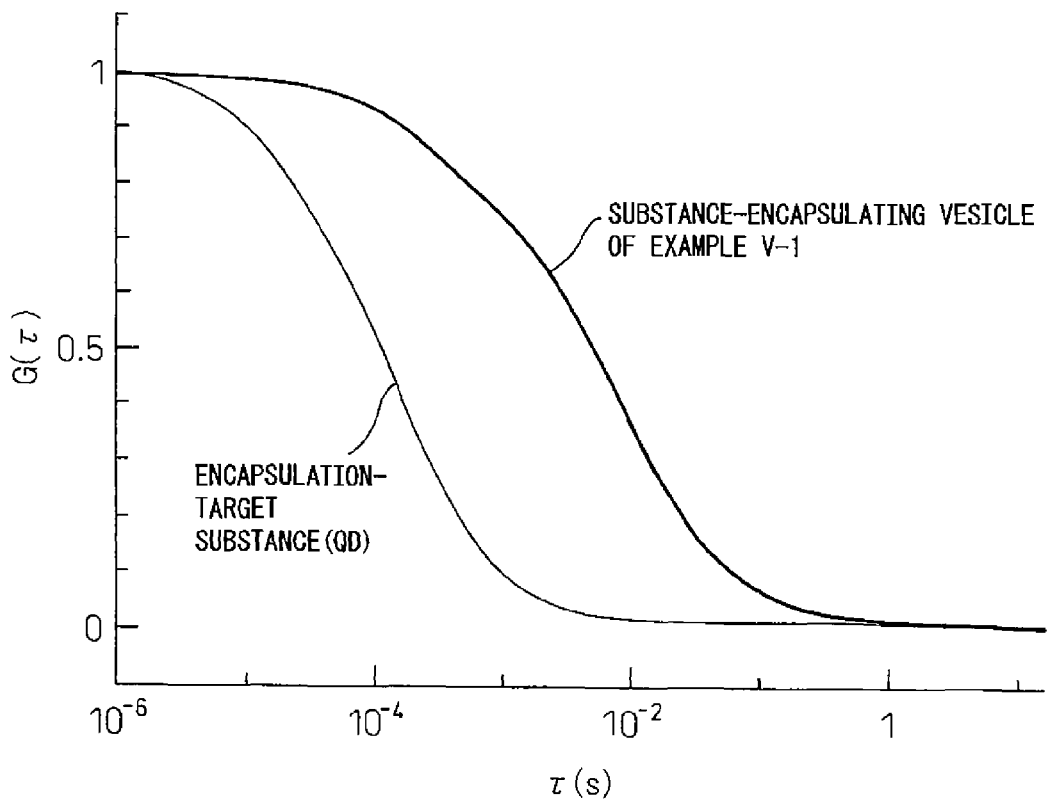
FIG. 14 is a graph showing the attenuation curve of the substance-encapsulating vesicle of Example V-1 measured by FCS.

As shown in FIG. 14, the attenuation curve of the solution after mixing of Example V-1 ("substance-encapsulating vesicle of Example 1" in the graph) is shifted more to the right compared to the attenuation curve of the QD solution ("encapsulation-target substance (QD)" in the graph) which is a encapsulation-target substance, indicating that the attenuation has become slow. Also, comparison with the FCS data described in Non-patent document 2 reveals that the attenuation curve of the solution after mixing of Example V-1 indicates attenuation similar to the vesicle with a particle size of about 100 nm.

From the above results, it can be seen that in the solution after mixing of Example V-1, substance-encapsulating vesicles wherein QD is encapsulated in the vacant vesicles have been formed.

Comparative Example V-1

Simultaneous Mixing of a Polymer and QD

Each of the first polymer and the second polymer similar to Example V-1 was dissolved in a 10 mM phosphate buffer (pH 7.4) (an aqueous medium) to a polymer concentration of 2.0 mg/ml. To the first polymer solution obtained, QD similar to that of Example V-1 was added as an encapsulation-target substance to a concentration of $2.3 \times 10^{15}$/ml, and then the second polymer solution was placed in an Eppendorf tube so that the charge ratio becomes equal (i.e. the C/A ratio=1.0), then agitated and mixed with a vortex mixer at 3300 rpm for 2 minutes, and then allowed to stand for over 3 minutes. The solution obtained (solution after mixing) was not transparent but cloudy unlike the solution after mixing of Example V-1.

Figure 15:
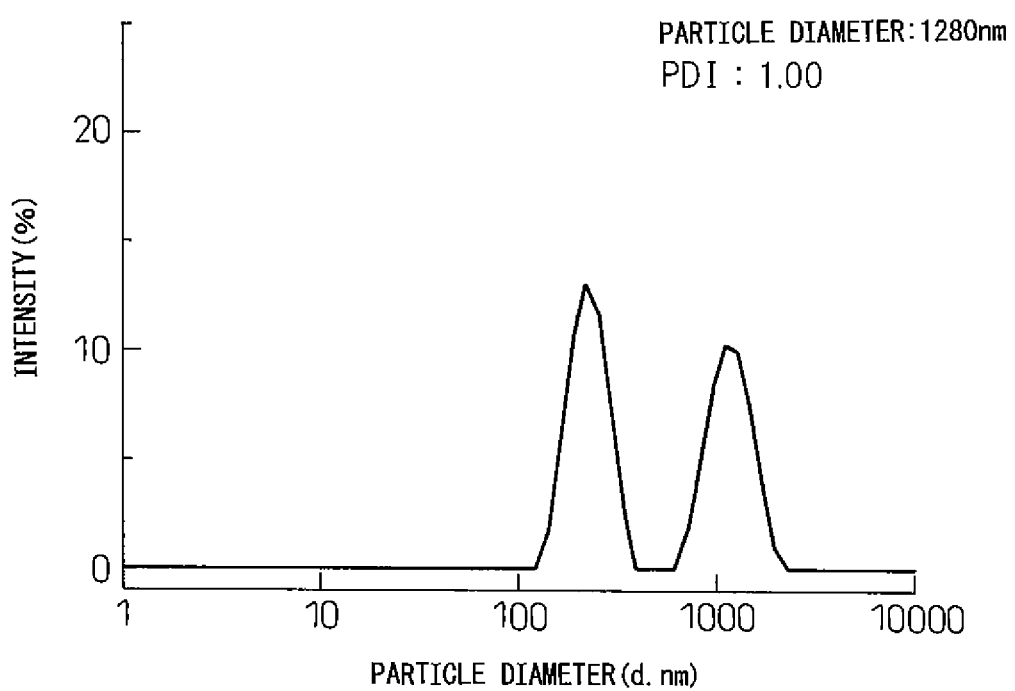
FIG. 15 is a graph showing the particle distribution of the substance-encapsulating vesicle of Comparative Example V-1.

The solution after mixing was measured by the dynamic light scattering method to determine particle size distribution. The graph of particle size distribution is shown in FIG. 15. As can be seen from FIG. 15, two particle size peaks were noted in stead of one particle size peak.

From the above results, it can be seen that in the solution after mixing (the solution obtained by simultaneously mixing the first polymer and the second polymer together with QD) obtained in Comparative Example V-1, the polymers do not form uniform vesicles unlike Example V-1 and QD-encapsulating vesicles have not been obtained as a uniform product, either.

Example V-2

In Vivo Evaluation of a QD-encapsulating Vesicle

Tumor model mice obtained by subcutaneously tranplanting Colon26 ($1.0 \times 10^6$/50 μl) to a hind limb of Balb/c nude mice were used on day 13 after transplantation. 31.4 μl of a QD-encapsulating vesicle solution obtained in a procedure similar to Example V-1 was diluted in PBS to a total volume of 200 μl (QD concentration: 36 μg/μl), and intravenously administered to the tumor model mice. 1, 12, 24 and 96 hours after the administration, fluorescent images were photographed using the IVIS (trademark) Fluorescence Imaging System (manufactured by Caliper).

For comparison, a PBS solution of QD alone supporting no vesicles (QD concentration: 36 μg/μl, total volume: 200 μl) was intravenously injected to tumor model mice similarly to the above, and fluorescent images were similarly photographed. For tumor model mice that did not receive QD, fluorescent images were similarly photographed.

Figure 16:
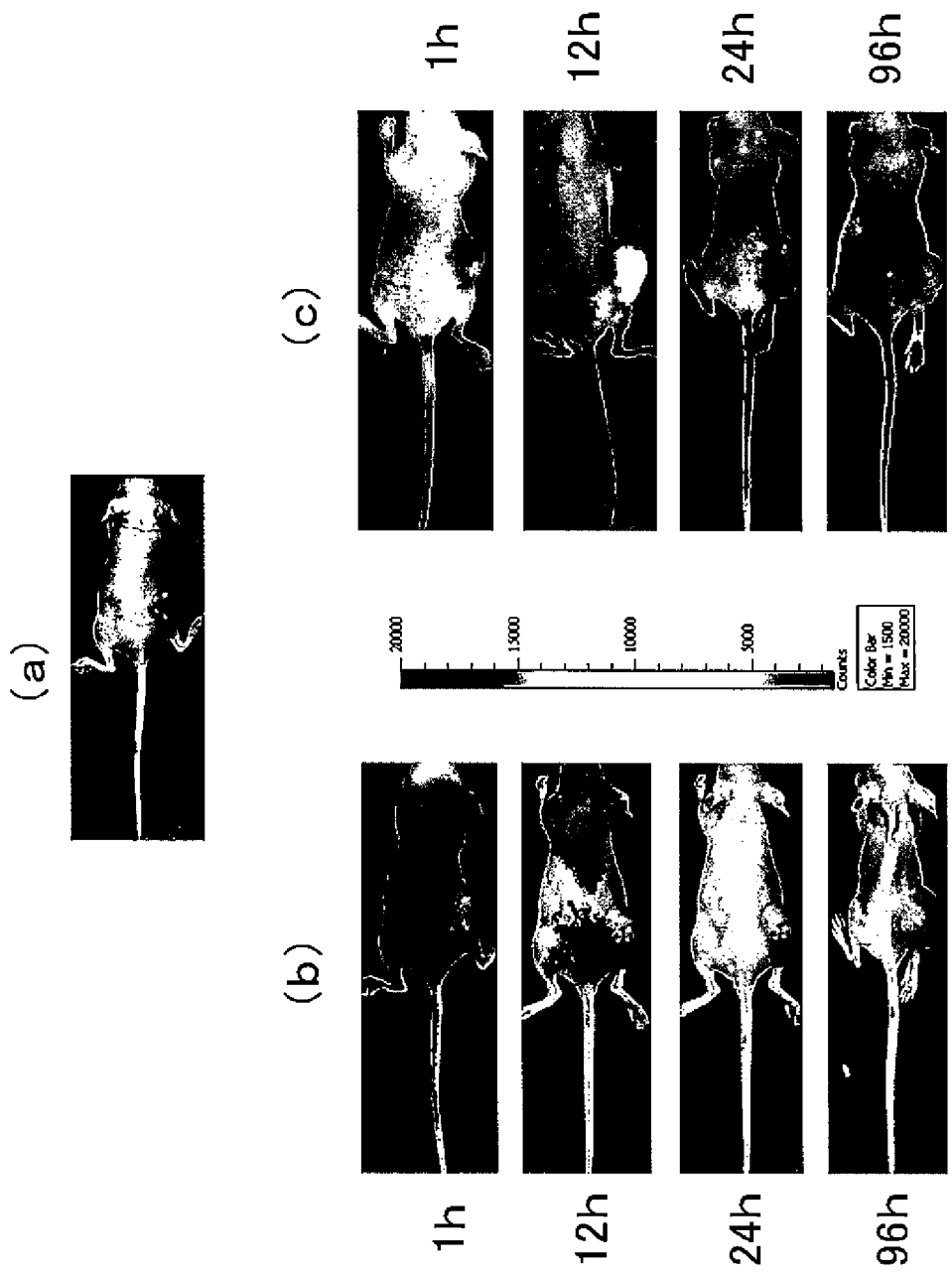
FIGS. 16(a) to (c) are photofluorograms showing the result of evaluating the in vitro activity of the substance-encapsulating vesicle of Example VI-1.

FIG. 16(*a*) is a fluorescent image of tumor model mice that did not receive QD, FIG. 16(*b*) is a fluorescent image (from the top to the bottom, 1, 12, 24, and 96 hours after administration) of tumor model mice that received QD alone, FIG. 16(*c*) is a fluorescent image of tumor model mice that the received QD-encapsulating vesicles (from the top to the bottom, 1, 12, 24, and 96 hours after administration). In the tumor model mice that received QD alone (see FIG. 16(*b*)), the blood level of QD has already decreased at 12 hours after the administration, and has been virtually eliminated at 24 hours after the administration, whereas in the tumor model mice that received the QD-encapsulating vesicles (see FIG. 16(*c*)), QD remains throughout the body even at 96 hours after the administration, and specifically accumulated at high concentration in the vicinity of the tumor. From this, it can be seen that the QD-encapsulating vesicle obtained in Example V-1 is highly excellent in retention in the blood and accumulation in the tumor. Based on this experiment, it is obvious that the substance-encapsulating vesicle of the present invention can be used very effectively as a DDS for drugs, etc.

Example Group VI

Production and Evaluation of a Positively Charged Substance-encapsulating Vesicle Example VI-1

Production of a Lysozyme (Positively Charged Substance)-encapsulating Vesicle

A procedure similar to that of Example V-1 was followed, except that QD was replaced with lysozyme (lysozyme from chicken egg white, manufactured by Sigma, mean particle size 3 nm, molecular weight 14,000, isoelectric point (pI)= about 11) as an encapsulation-target substance and the encapsulation-target substance in the subject solution to be mixed was added to a concentration of 1 mg/ml. The solution obtained after mixing was transparent.

Figure 17:
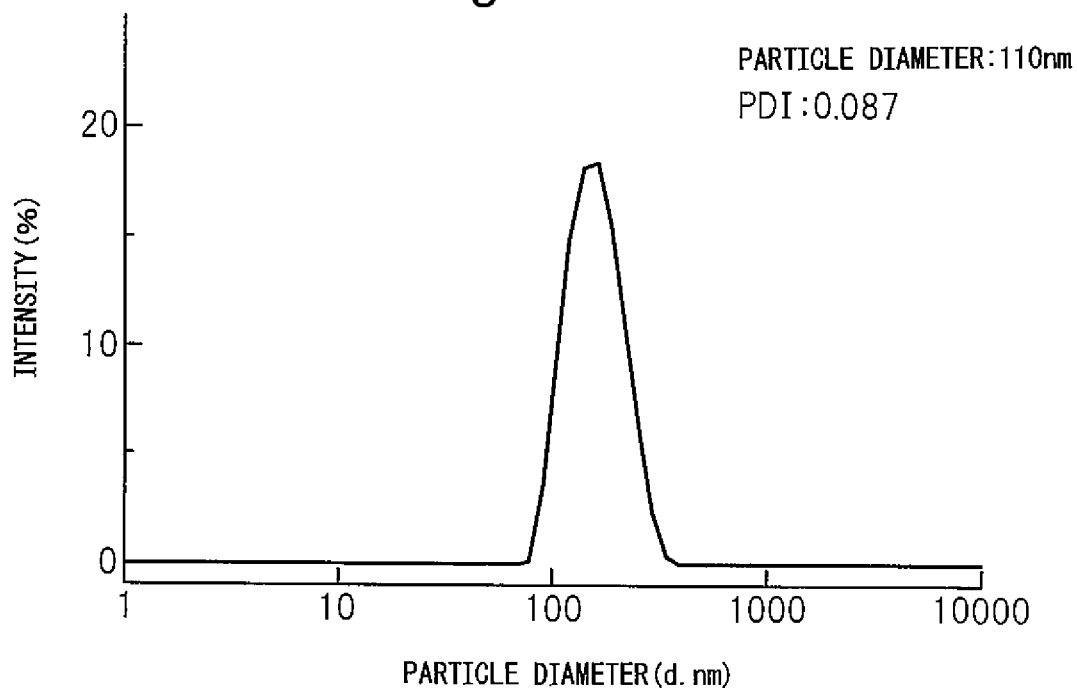
FIG. 17 is a graph showing the particle distribution of the substance-encapsulating vesicle of Example VI-1.

The solution after mixing was added to a solution (in a 10 mM phosphate buffer (0 mM NaCl), pH 7.4) containing 10 equivalents of EDC relative to the carboxyl group contained in PEG-P(Asp) in the vesicle, and then allowed to stand at room temperature for 12 hours to crosslink the polymer. Lysozyme remaining in the free state in the solution without being encapsulated was removed by centrifugal ultrafiltration (VIVASPIN 20 manufactured by Sartorius Sterium Biotech, a molecular weight cutoff of 300,000 was used; 300 rpm, 4° C.) to purify the solution, which was then measured by the dynamic light scattering method to determine particle size distribution, mean particle size, and polydispersity index (PDI). The graph of particle size distribution is shown in FIG. 17. At a mean particle size of 110 nm, the formation of monodispersion particles was noted. The PDI was 0.087.

Figure 18:
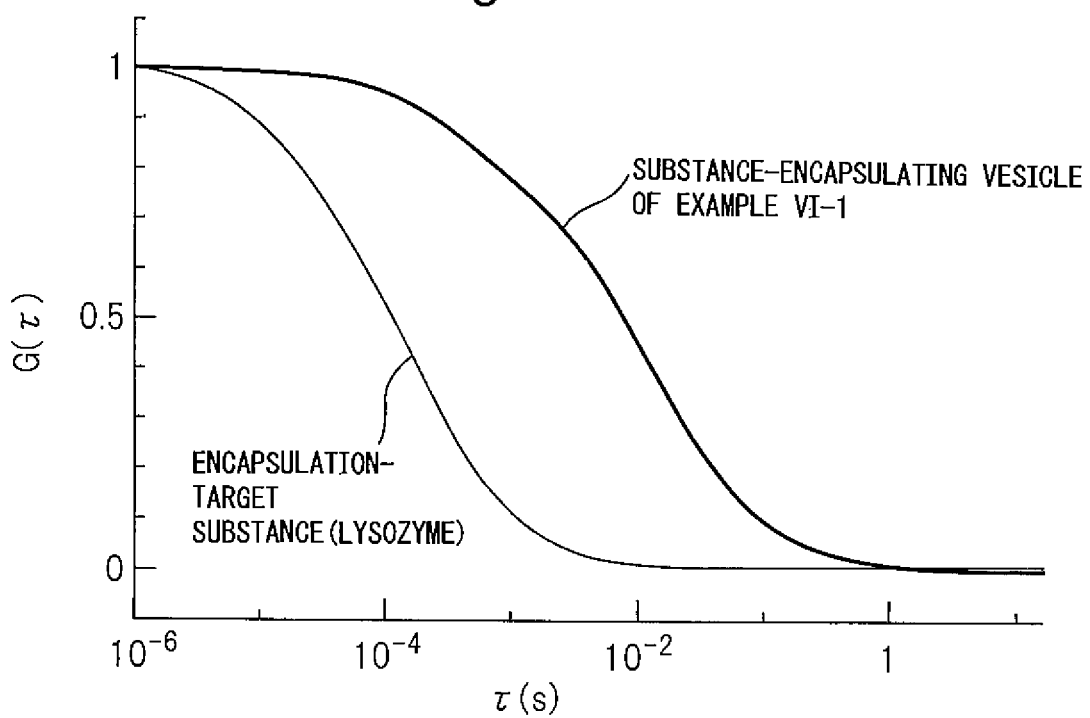
FIG. 18 is a graph showing the attenuation curve of the substance-encapsulating vesicle of Example VI-1 measured by FCS.

Subsequently, the solution after purification was measured by the fluorescence correlation spectroscopy (FCS) method to determine an autocorrelation function G(τ). For the solution of lysozyme (1 mg/ml) which is an encapsulation-target substance as well, measurement by FCS was conducted to determine an autocorrelation function G(τ). The temporal attenuation curve of the autocorrelation function G(τ) obtained is shown in FIG. 18. As shown in FIG. 18, the attenuation curve of the solution after mixing of Example 2 ("the substance-encapsulating vesicle of Example VI-1" in the graph) is shifted more to the right compared to the attenuation curve of lysozyme ("encapsulation-target substance (lysozyme)" in the graph) which is an encapsulation-target substance, indicating that the attenuation has become slow. Also, comparison with the FCS data described in Non-patent document 2 reveals that the attenuation curve of the solution after mixing of Example VI-1 is showing attenuation similar to the vesicle with a particle size of about 100 nm.

From the above results, it can be seen that in the solution after mixing of Example VI-1, substance-encapsulating vesicles wherein lysozyme is encapsulated in the vacant vesicles have been formed.

Comparative Example VI-1

Simultaneous Mixing of a Polymer and Lysozyme

Each of the first polymer and the second polymer similar to Example VI-1 was dissolved in a 10 mM phosphate buffer (pH 7.4) (an aqueous medium) to a polymer concentration of 2.0 mg/ml. To the first polymer solution obtained, lysozyme similar to that of Example VI-1 was added as an encapsulation-target substance to a concentration of 1.0 mg/ml, and then the second polymer solution was placed in an Eppendorf tube so that the charge ratio becomes equal (i.e. the C/A ratio=1.0), then agitated and mixed with a vortex mixer at 3300 rpm for 2 minutes, and then allowed to stand for over 3 minutes. The solution obtained (solution after mixing) was not transparent but cloudy unlike the solution after mixing of Example V-I1.

Figure 19:
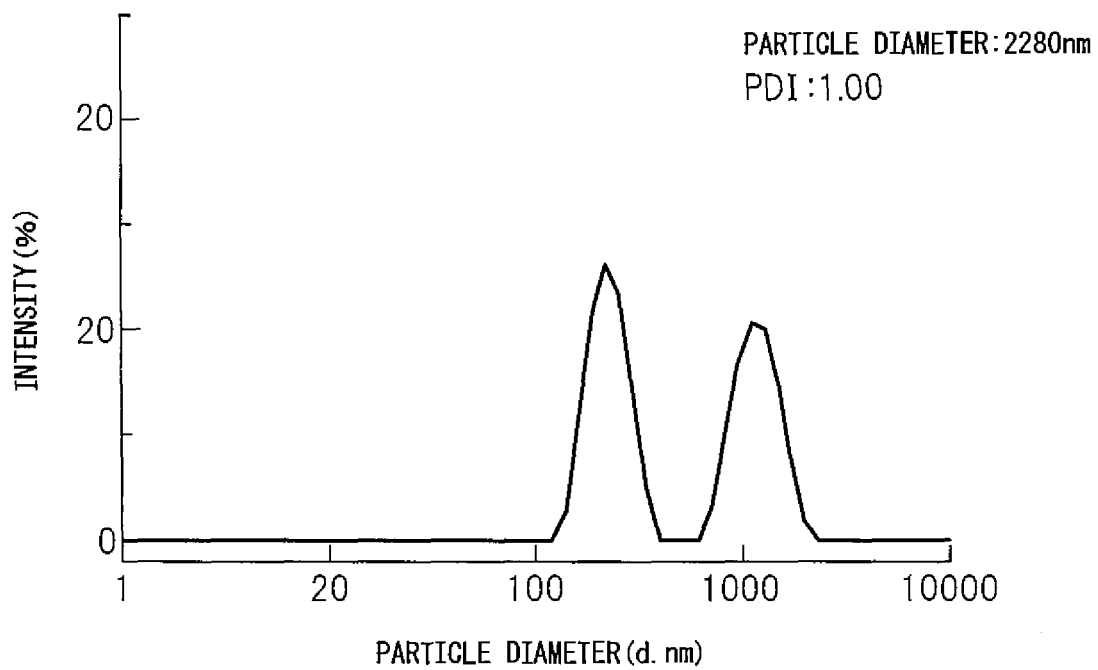
FIG. 19 is a graph showing the particle distribution of the substance-encapsulating vesicle of Comparative Example VI-1.

The solution after mixing was measured by the dynamic light scattering method to determine particle size distribution. The graph of particle size distribution is shown in FIG. 19. As can be seen from FIG. 19, two particle size peaks were noted in stead of one particle size peak.

From the above results, it can be seen that in the solution after mixing (the solution obtained by simultaneously mixing the first polymer and the second polymer together with lysozyme) obtained in Comparative Example VI-1, the polymers do not form uniform vesicles unlike Example VI-1, and lysozyme-encapsulating vesicles have not been obtained as a uniform product, either.

Example VII

Production of a Macromolecule (Cy3-labelled PIC Micelle)-encapsulating Vesicle

A procedure similar to Example V-1 was followed except that a crosslinked fluorescence-labeled micelle (Cy3-labelled PIC micelle, Cy3-labelled PEG-P(Asp) and PEG-P(Asp-AP) (for all of them, the molecular weight of PEG is 2,000, the degree of polymerization of ion chain is 75) were mixed and prepared so as to balance the electric charge, and then crosslinked with 10 equivalents of EDC, and similarly purified with a molecular weight cutoff of 100,000; mean particle size 38.0 nm, PDI 0.032) was used in stead of QD as an encapsulation-target substance, and added to a concentration of the encapsulation-target substance in the subject solution to be mixed of 1 mg/ml. The solution obtained after mixing was transparent.

The solution after mixing was added to a solution (in a 10 mM phosphate buffer (0 mM NaCl), pH 7.4) containing 10 equivalents of EDC relative to the carboxyl group contained in PEG-P(Asp) in the vesicle, and then allowed to stand at room temperature for 12 hours. The crosslinked micelle remaining in the free state in the solution without being encapsulated in the vesicle was removed by centrifugal ultrafiltration (VIVASPIN 20 manufactured by Sartorius Sterium Biotech, a molecular weight cutoff of 300,000 was used; 300 rpm, 4° C.) to purify the solution, which was then measured by the dynamic light scattering method to determine particle size distribution, mean particle size, and polydispersity index (PDI). At a mean particle size of 113 nm, the formation of monodispersion particles was noted. The PDI was 0.063.

Figure 20:
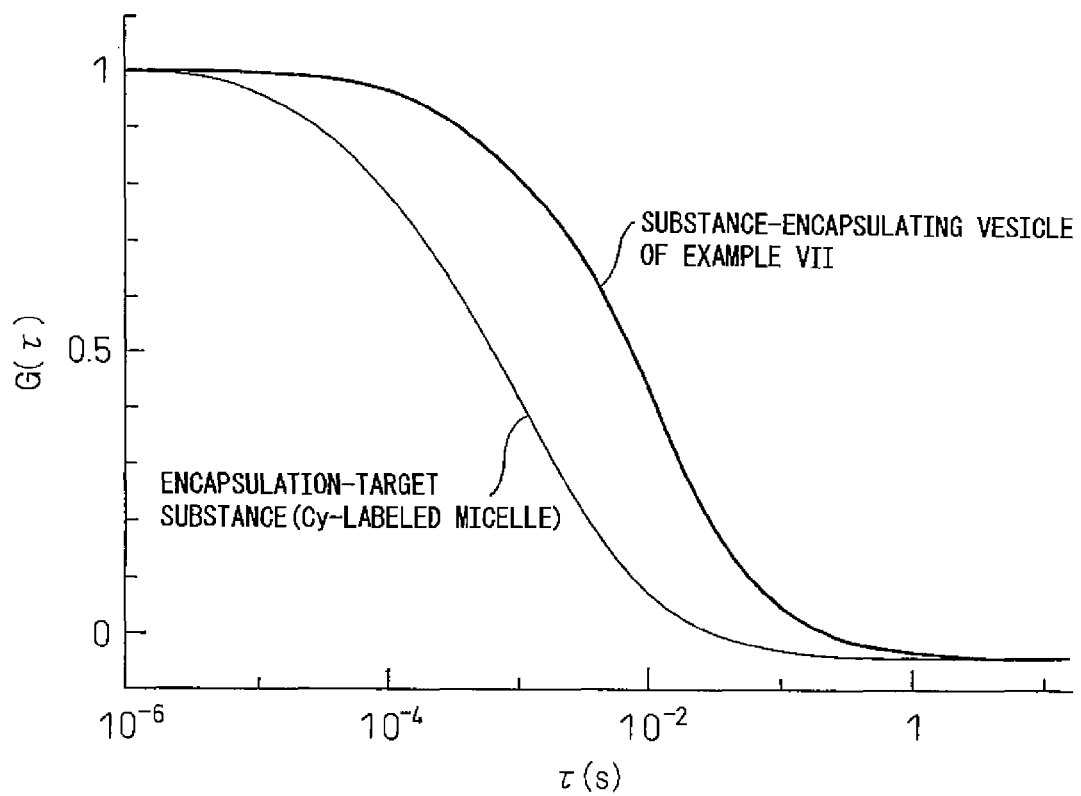
FIG. 20 is a graph showing the attenuation curve of the substance-encapsulating vesicle of Example VII measured by FCS.

Also, the solution after purification was measured by the fluorescence correlation spectroscopy (FCS) method to determine an autocorrelation function G(τ). For the solution of fluorescence-labeled micelle (1 mg/ml) which is an encapsulation-target substance as well, measurement by FCS was conducted to determine an autocorrelation function G(τ). The temporal attenuation curve of the autocorrelation function G(τ) obtained is shown in FIG. 20. As shown in FIG. 20, the attenuation curve of the solution after mixing of Example VII ("the substance-encapsulating vesicle of Example 2" in the graph) is shifted more to the right compared to the attenuation curve of the fluorescence-labeled micelle ("the encapsulation-target substance (Cy3-labelled PIC micelle)" in the graph) which is an encapsulation-target substance, indicating that the attenuation has become slow. Also, comparison with the FCS data described in Non-patent document 2 reveals that the attenuation curve of the solution after mixing of Example VII is showing attenuation similar to the vesicle with a particle size of about 100 nm.

Also, the solution after mixing was examined by a phase-contrast cryo-transmission electron microscope. A sample solution was developed onto a microgrid, excess water was blotted off with a filter paper, and then was quick-frozen in a liquified ethane using EM CPC cryo-station (manufactured by Leica Microsystems) to prepare a specimen for examination. Images were photographed at −170° C. using a transmission electron microscope JEM2011 (manufactured by JEOL Ltd.) equipped with a Zernike phase plate. The electron micrographs obtained are shown in FIGS. 21(a) and (b). As can be seen from FIGS. 21(a) and (b), spherical vesicle particles with a membrane thickness of about 10 nm were observed, confirming that they had a structure similar to the vacant vesicle.

The above results reveal that in the solution after mixing of Example VII, the substance-encapsulating vesicles encapsulating fluorescence-labeled micelle in the vacant vesicles have been formed.

Example VIII

Production and Evaluation of an Enzyme (β-glucosidase)-encapsulating Vesicle

A procedure similar to Example V-1 was followed except that QD was replaced with β-glucosidase (derived from almond, manufactured by Sigma, molecular weight 10,000, isoelectric point (pI)=about 43) and the encapsulation-target substance in the subject solution to be mixed was added to a concentration of 1 mg/ml. The solution obtained after mixing was transparent.

The solution after mixing was added to a solution (in a 10 mM phosphate buffer (0 mM NaCl), pH 7.4) containing 10 equivalents of EDC relative to the carboxyl group contained in PEG-P(Asp) in the vesicle, and then allowed to stand at room temperature for 12 hours to crosslink the polymer. β-glucosidase remaining in the free state in the solution without being encapsulated in the vesicle was removed by centrifugal ultrafiltration (VIVASPIN 20 manufactured by Sartorius Sterium Biotech, a molecular weight cutoff of 300,000 was used; 300 rpm, 4° C.) to purify the solution, which was substituted to PBS to obtain a β-glucosidase-encapsulating vesicle solution.

100 µl of the β-glucosidase-encapsulating vesicle solution obtained was incubated at 37° C. for 15 minutes. Subsequently, to this solution, 100 µl of 30.1 mg/ml solution of o-nitrophenyl-β-D-glucopyranoside in PBS (the abbreviated name ONPGlc, molecular weight 301) was added, and further incubated at 37° C. for 15 minutes. Then 50 µl of 1 mg/ml $Na_2CO_3$ solution at a concentration of 22.1 mg/ml was added, and absorbance at around 420 nm was determined.

ONPGlc with a molecular weight of 301 can penetrate and enter into the EDC-crosslinked vesicle. ONPGlc is a substrate for β-glucosidase, and can produce o-nitrophenol when hydrolyzed by β-glucosidase. Since o-nitrophenol has a UV absorption peak at around 420 nm in which ONPGlc has no such peak, the enzyme activity of β-glucosidase can be determined by observing this peak.

Figure 22:
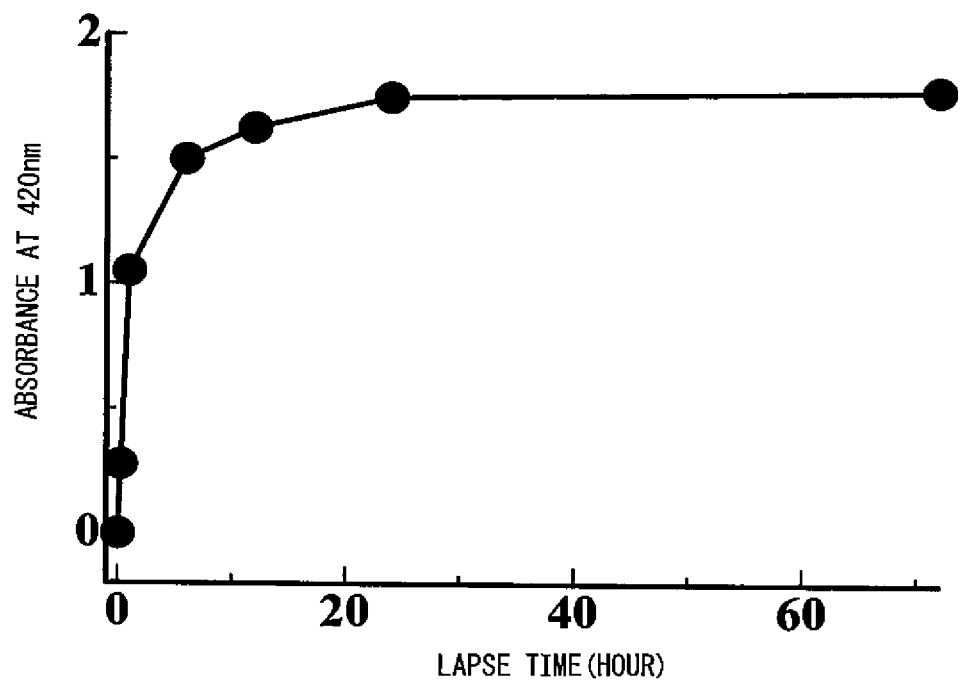
FIG. 22 is a photofluorogram showing the result of evaluating the in vitro activity of the substance-encapsulating vesicle of Example VIII.

Changes with time of absorbance obtained are shown in FIG. 22. It can be seen from FIG. 22 that though the vesicle was crosslinked with EDC, β-glucosidase in the vesicle exhibited the enzyme activity without being inactivated. It is clear from this experiment that the substance-encapsulating vesicle of the present invention can be used highly effectively as an enzyme carrier, too.

Reference Experiment

Disturbance of Vacant Vesicle Structure by Mixing

The vacant vesicle solution obtained by a procedure similar to Example V-1 was added to a solution (in a 10 mM phosphate buffer (0 mM NaCl), pH 7.4) containing 10 equivalents of EDC relative to the carboxyl group contained in PEG-P(Asp) in the vesicle, and then allowed to stand at room temperature for 12 hours to crosslink the polymer. After crosslinking, molecular weight distribution was determined by gel permeation chromatography (GPC). For GPC, the eluent used was 10 mM PB (pH 7.4, 150 mM NaCl) and the column used was Superose 6™ 10/300 GL (manufactured by GE Healthcare), and the eluent was passed through the column at a flow rate of 0.5 ml/min and detected by a UV detector (220 nm) and a fluorescence detector (Ex/Em=520/550 nm).

To the vacant vesicle solution obtained by a procedure similar to Example V-1, a solution (in a 10 mM phosphate buffer (0 mM NaCl), pH 7.4) containing 10 equivalents of EDC relative to the carboxyl group contained in PEG-P (Asp) in the vesicle was added while agitating and mixing with a vortex mixer at about 2000 rpm to conduct crosslinking. After crosslinking, molecular weight distribution was determined GPC.

Figure 23:
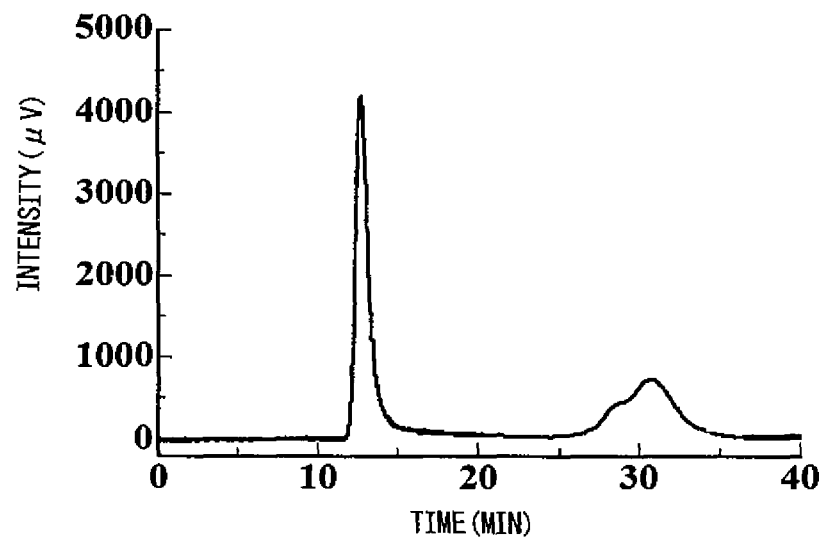
FIG. 23 is a graph showing changes in the structure of a vacant vesicle by mixing.
Figure 23:
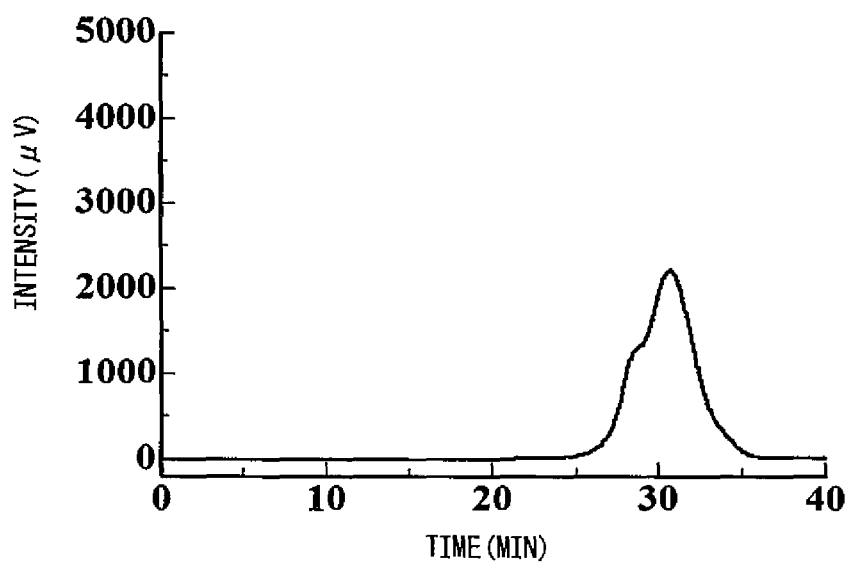

GPC profiles obtained for the crosslinked solution before mixing and the crosslinked solution after mixing are shown FIGS. 23(a) and (b), respectively. In the GPC profile (see FIG. 23(a)) of the crosslinked solution before mixing, a peak appearing at about 12-13 minutes indicates the vesicle of a large molecular weight, and a peak appearing at about 30 minutes indicates a non-aggregate (an assembly of polymers not forming vesicles) of a smaller molecular weight. On the other hand, in the GPC profile (see FIG. 23(a)) of the crosslinked solution after mixing, the peak of the vesicle disappeared and the peak of the non-aggregate is enhanced. The result shows that mixing disturbed the structure of the vacant vesicle and broke down to small aggregates.

INDUSTRIAL APPLICABILITY

In accordance with the present invention, a vesicle (substance-encapsulating vesicle) containing/supporting a substance in a cavity of a vacant vesicle obtained by polymer self-assembly in water can be simply and effectively produced using the reproducing ability of the vesicle, and thus has a very high usefulness in the fields of DDS for delivering drugs, biomaterials/function materials and the like. Specifically, the present invention has a great significance in that it developed a method for encapsulating a substance whose direct encapsulation into the electrostatically interacting vesicle (PICsome) is difficult, thereby expanding the application range of the encapsulation-target substance. In fact, it is remarkably useful in that it expanded the application range of PICsome with a mean particle size of 100-200 nm that exhibits excellent blood retention and tumor accumulation.

Also, in accordance with the present invention, a vesicle retaining nucleic acid in the membrane thereof is also provided, and the intra-membrane nucleic acid-containing vesicle is useful as a DDS for delivering such nucleic acid and as biomaterials/functionally materials comprising nucleic acid as an active ingredient. The present invention also permits the encapsulation of another drug in a cavity of the vesicle, and therefore is also useful as a DDS that delivers nucleic acid in combination with another drug.

The invention claimed is:

1. A vesicle comprising:
a membrane containing a first polymer, which is a block copolymer having an uncharged hydrophilic segment and a first charged segment, and a second polymer, which has a second charged segment charged oppositely to the first charged segment, said membrane defining a cavity surrounded thereby and having a first charged segment to second charged segment ratio of 0.3 to less than 3.00; and
a charged substance encapsulated in the cavity.

2. A vesicle according to claim 1, wherein the membrane has a trilaminar structure comprising an outer layer, an intermediate layer, and an inner layer.

3. A vesicle according to claim 1, wherein the charged substance is selected from the group consisting of biomolecules, organic compounds and inorganic substances.

4. A vesicle according to claim 1, wherein the first polymer is a block copolymer containing an uncharged hydrophilic segment and an anionic segment, and the second polymer is a block copolymer containing an uncharged hydrophilic segment and a cationic segment and/or a polymer containing a cationic segment but no uncharged hydrophilic segment.

5. A vesicle according to claim 1, wherein the first polymer is a block copolymer containing an uncharged hydrophilic segment and a cationic segment, and the second polymer is a block copolymer containing an uncharged hydrophilic segment and an anionic segment and/or a polymer containing an anionic segment but no uncharged hydrophilic segment.

6. A vesicle according to claim 4 or 5, wherein the anionic segment is nucleic acid.

7. A vesicle according to claim 4 or 5, wherein the cationic segment is polyamine.

8. A vesicle according to claim 4 or 5, wherein the uncharged hydrophilic segment is polyalkylene glycol.

* * * * *